US012694716B2

(12) United States Patent
Kumar et al.

(10) Patent No.: US 12,694,716 B2
(45) Date of Patent: Jul. 28, 2026

(54) ACTION DETECTION USING MACHINE LEARNING MODELS

(71) Applicant: The Jackson Laboratory, Bar Harbor, ME (US)

(72) Inventors: Vivek Kumar, Bar Harbor, ME (US); Brian Q. Geuther, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 320 days.

(21) Appl. No.: 18/245,651

(22) PCT Filed: Sep. 16, 2021

(86) PCT No.: PCT/US2021/050572
§ 371 (c)(1),
(2) Date: Mar. 16, 2023

(87) PCT Pub. No.: WO2022/060919
PCT Pub. Date: Mar. 24, 2022

(65) Prior Publication Data
US 2023/0360441 A1 Nov. 9, 2023

Related U.S. Application Data

(60) Provisional application No. 63/078,952, filed on Sep. 16, 2020.

(51) Int. Cl.
*G06V 40/20* (2022.01)
*A61B 5/00* (2006.01)
*G06V 20/40* (2022.01)

(52) U.S. Cl.
CPC ............ *G06V 40/20* (2022.01); *A61B 5/4082* (2013.01); *A61B 5/4088* (2013.01); *G06V 20/46* (2022.01)

(58) Field of Classification Search
CPC ........ G06V 40/20; G06V 20/46; G06V 20/41; G06V 20/52; G06V 40/23; G06V 10/242;
(Continued)

(56) References Cited

U.S. PATENT DOCUMENTS 8,391,645 B2 3/2013 Steinberg
2010/0136533 A1* 6/2010 Hwang .............. G01N 33/6872
435/7.1
(Continued)

FOREIGN PATENT DOCUMENTS

CN 110796029 A * 2/2020 ........... G06F 18/241
CN 111611392 A 9/2020

OTHER PUBLICATIONS

Salim et al., ("Classifier combination and score level fusion: concepts and practical aspects", International Journal of image and Data fusion vol. I, No., 2, Jun. 2010, pp. 113-135) (Year: 2010).*
(Continued)

Primary Examiner — Amara Abdi
(74) Attorney, Agent, or Firm — McDonnell Boehnen Hulbert & Berghoff LLP

(57) ABSTRACT

Systems and methods described herein provide techniques for detecting subject behavior by processing video data using one or more trained models configured to detect subject behavior. The described system processes sets of frames from the video data using different trained models. The system further processes different orientations of the sets of frames. The various outputs from the different trained models and from processing the different orientations of the sets of frames may be combined to then make a final determination as to whether the subject is exhibiting a particular behavior during a particular frame.

18 Claims, 63 Drawing Sheets

(58) Field of Classification Search

CPC ...... G06V 20/49; G06V 20/70; A61B 5/4082; A61B 5/4088; G06F 18/254; G06F 18/256; G06N 20/00

See application file for complete search history.

(56) References Cited

U.S. PATENT DOCUMENTS

| | | | |
|---|---|---|---|
| 2013/0129308 A1* | 5/2013 | Karn | H04N 21/47217 |
| | | | 386/230 |
| 2014/0207433 A1* | 7/2014 | Chen | A01K 1/031 |
| | | | 703/2 |
| 2018/0225516 A1* | 8/2018 | Serre | G06N 3/084 |
| 2019/0087965 A1* | 3/2019 | Datta | G06T 7/215 |
| 2022/0032199 A1* | 2/2022 | Rudi | G06N 20/00 |

OTHER PUBLICATIONS

Swetha et al., (Scale and Rotation Corrected CNNs (SRC-CNNs) for Scale and Rotation Invariant Character Recognition SRC-CNN for Scale and Rotation Invariant Character Recognition, Indian Conference on Compute, Dec. 18, 2018 (Year: 2018).*

Giddwani Bharat et al: ""Eigen Vectors based Rotation Invariant Multi-Object Deep Detector"", 2020 7th International Conference onsignal Processing and Integrated Networks(Spin) , IEEE, Feb. 27, 2020 (Feb. 27, 2020), pp. 246-251, XP033759301, DOI: 10.1109/ SPIN48934.2020.9070989 figure 2.

Hueihan Jhuang et al: ""Automated home-cage behavioural phenotyping of mice"", Nature Communications, vol. 1, No. 6,Sep. 1, 2010 (Sep. 1, 2010), pp. 1-9, XP055305004, ISSN: 2041-1723, DOI: 10.1038/ncomms1064p.8, first paragraph.

Salim Chitroub: ""Classifier combinationand score level fusion: concepts andpractical aspects"", International Journal of Image and Datafusion, vol. 1, No. 2, Jun. 1, 2010 (Jun. 1, 2010), pp. 113-135, XP055409269, ISSN: 1947-9832, DOI:10.1080/19479830903561944 figures 2, 6.

Geuther Brian Q et al: ""Action detection using a neural network elucidates the genetics of mouse grooming behavior : eLife"", Mar. 17, 2021 (Mar. 17, 2021), pp. 1-41, XP055872729, DOI: 10.7554/ eLife.63207 Retrieved from the Internet:URL:https://elifesciences. org/articles/63207 [retrieved on Dec. 14, 2021] entire document, particularly fig.3.

Swetha V C et al, Scale and Rotation Corrected CNNs (SRC-CNNs) for Scale and Rotation Invariant Character Recognition SRC-CNN for Scale and Rotation Invariant Character Recognition, Indian Conference on Compute, Dec. 18, 2018.

Rutten K et al, Automated scoring of novel object recognition in rats. J Neurosci Methods. Jun. 15, 2008;171(1):72-7. doi: 10.1016/ j.jneumeth.2008.02.006. Epub Feb. 17, 2008. PMID: 18372047.

* cited by examiner

Figure 4:
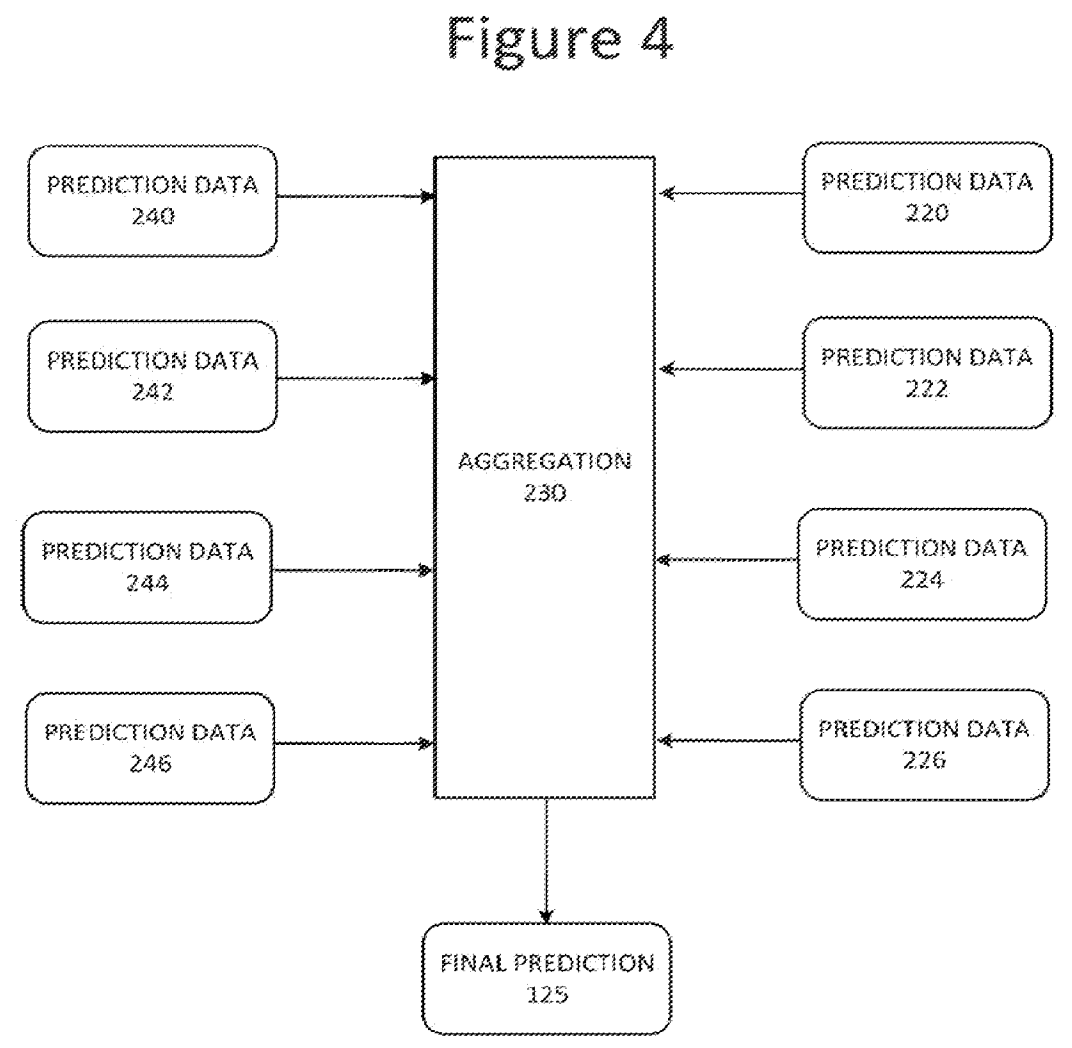

PREDICTION DATA 220

PREDICTION DATA 222

PREDICTION DATA 224

PREDICTION DATA 226

PREDICTION DATA 240

PREDICTION DATA 242

PREDICTION DATA 244

PREDICTION DATA 246

AGGREGATION 230

FINAL PREDICTION 125

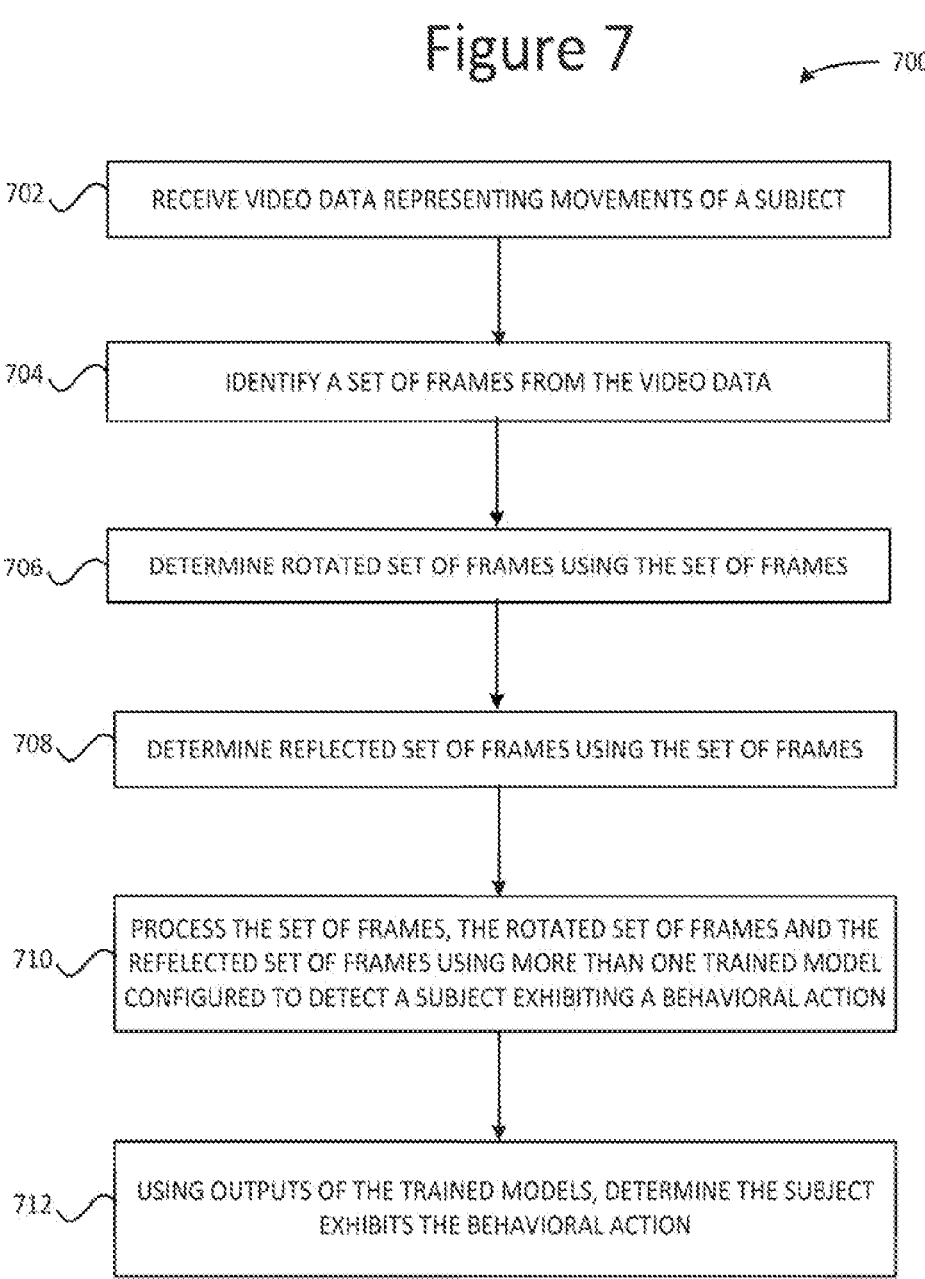

702 — RECEIVE VIDEO DATA REPRESENTING MOVEMENTS OF A SUBJECT

704 — IDENTIFY A SET OF FRAMES FROM THE VIDEO DATA

706 — DETERMINE ROTATED SET OF FRAMES USING THE SET OF FRAMES

708 — DETERMINE REFLECTED SET OF FRAMES USING THE SET OF FRAMES

710 — PROCESS THE SET OF FRAMES, THE ROTATED SET OF FRAMES AND THE REFLECTED SET OF FRAMES USING MORE THAN ONE TRAINED MODEL CONFIGURED TO DETECT A SUBJECT EXHIBITING A BEHAVIORAL ACTION

712 — USING OUTPUTS OF THE TRAINED MODELS, DETERMINE THE SUBJECT EXHIBITS THE BEHAVIORAL ACTION

Fig. 9A

Outer: Training
Inner: Validation

Grooming Predictions

Fig. 10C

Fig. 13A                    Both Near Perfect
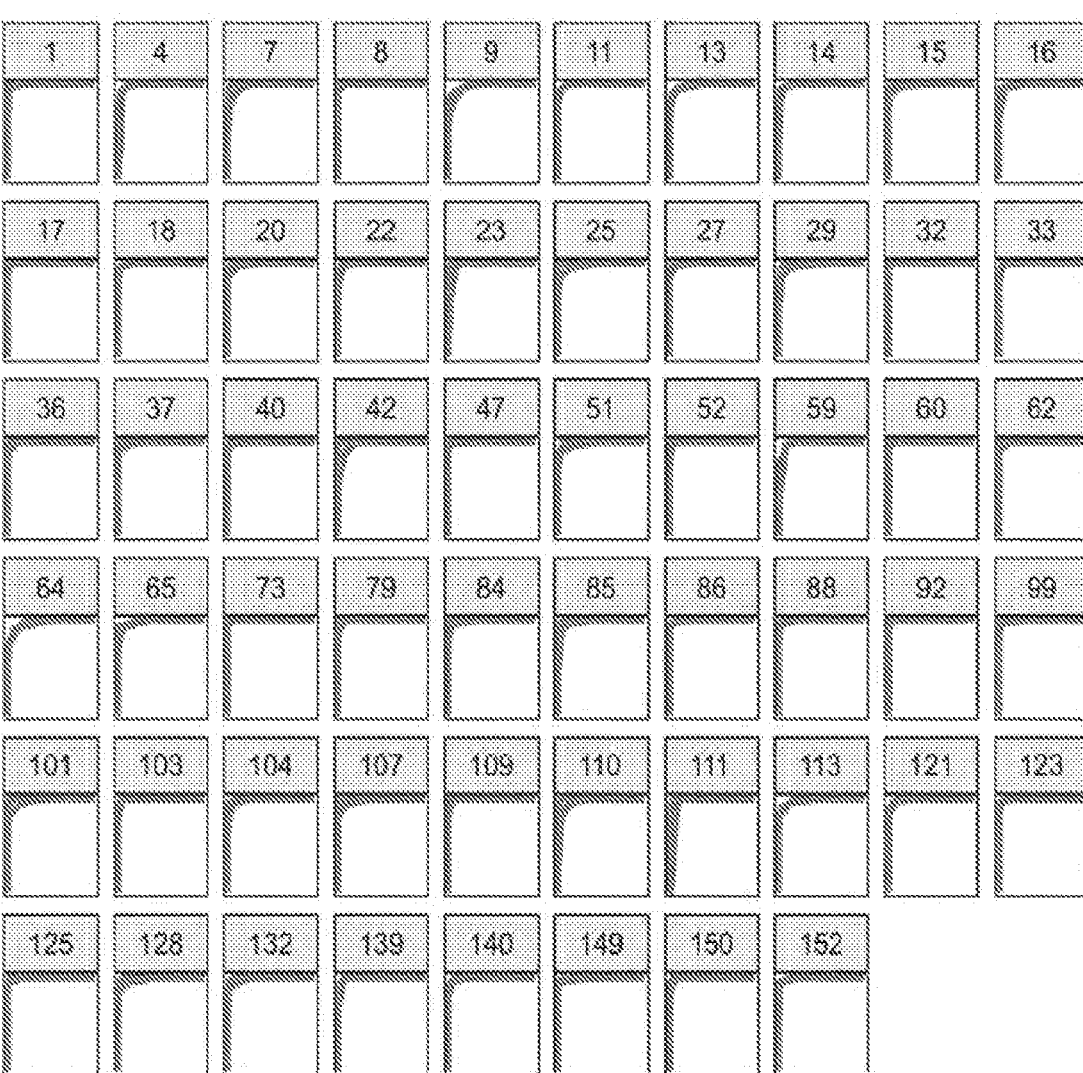
Fig. 13B                    Both Acceptable
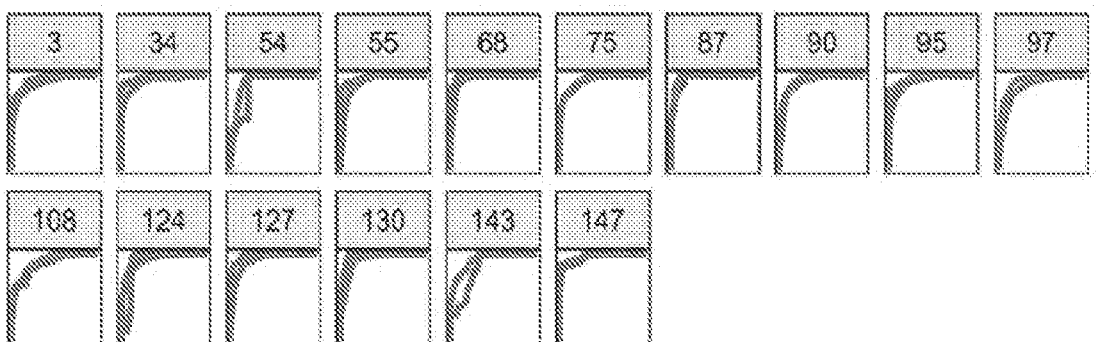

Fig. 13C     NN Near Perfect, JAABA Acceptable

Fig. 13D                              Fig. 13E

Both Poor                            NN >> JAABA

Fig. 15C

| Category | PhenoName | PhenoDescription | Units |
|---|---|---|---|
| Grooming Quantity | GrTime5m | Sum of grooming duration, first 5 minutes | seconds |
| Grooming Quantity | GrTime20m | Sum of grooming duration, first 20 minutes | seconds |
| Grooming Quantity | GrTime55m | Sum of grooming duration, first 55 minutes | seconds |
| Grooming Pattern | GrTimeSlope55m | Linear fit for grooming duration in the first 55 minute-level bins | - |
| Grooming Quantity | GrBoutNum5m | Count of grooming bouts, first 5 minutes | integer |
| Grooming Quantity | GrBoutNum20m | Count of grooming bouts, first 20 minutes | integer |
| Grooming Quantity | GrBoutNum55m | Count of grooming bouts, first 55 minutes | integer |
| Grooming Quantity | GrBoutNumSlope55m | Linear fit for bout count in the first 55 minute-level bins | - |
| Grooming Pattern | GrBoutLength5m | Time spent grooming divided by number of bouts, first 5 minutes | seconds |
| Grooming Pattern | GrBoutLength20m | Time spent grooming divided by number of bouts, first 20 minutes | seconds |
| Grooming Pattern | GrBoutLength55m | Time spent grooming divided by number of bouts, first 55 minutes | seconds |
| Grooming Pattern | GrBoutLengthSlope55m | Linear fit for average bout length in the first 55 minute-level bins | - |
| Open Field Anxiety | OFCornerTime5m | Time spent in any corner, first 5 minutes | seconds |
| Open Field Anxiety | OFCornerTime20m | Time spent in any corner, first 20 minutes | seconds |
| Open Field Anxiety | OFCornerTime55m | Time spent in any corner, first 55 minutes | seconds |
| Open Field Activity | OFDistTraveled5m | Locomotor activity, first 5 minutes | cm |
| Open Field Activity | OFDistTraveled20m | Locomotor activity, first 20 minutes | cm |
| Open Field Activity | OFDistTraveled55m | Locomotor activity, first 55 minutes | cm |
| Open Field Anxiety | OFPeripheryTime5m | Time spent along any wall, first 5 minutes | seconds |
| Open Field Anxiety | OFPeripheryTime20m | Time spent along any wall, first 20 minutes | seconds |
| Open Field Anxiety | OFPeripheryTime55m | Time spent along any wall, first 55 minutes | seconds |
| Grooming Pattern | GrPeakMidBin | Center of the 5-minute time bin when the most grooming occurred | minutes |
| Grooming Quantity | GrPeakVal | Value of the time bin when the most grooming occurred | seconds |
| Grooming Pattern | GrPeakSlope | PeakVal divided by PeakMidBin | - |

Avg. Bout Length

Total Grooming

Fig. 19B

-log(P-value)

2   4   6   8

A: Gr len & time
B: Gr pattern
C: Gr len, num & time
D: OFA activity & anxiety
E: Gr pattern and OFA activity
F: Gr num
G: overall grooming

Fig. 24A

MGI:101924,MGI:103078,MGI:103285,MGI:104554,MGI:104565,MGI:104684,MGI:104719,MGI:106011,MGI:1062
17,MGI:106651,MGI:106925,MGI:107582,MGI:107585,MGI:107717,MGI:107745,MGI:107935,MGI:108005,MGI:10
8029,MGI:108408,MGI:108511,MGI:109246,MGI:109483,MGI:109585,MGI:109632,MGI:1097152,MGI:1098266,M
GI:1098567,MGI:1098783,MGI:1098827,MGI:1099446,MGI:1100508,MGI:1101759,MGI:1195256,MGI:1196356,M
GI:1201683,MGI:1202392,MGI:1202876,MGI:1203524,MGI:1276116,MGI:1277961,MGI:1298218,MGI:1315197,M
GI:1316660,MGI:1321386,MGI:1328323,MGI:1329003,MGI:1329037,MGI:1333753,MGI:1333815,MGI:1339758,M
GI:1339963,MGI:1345149,MGI:1345153,MGI:1345180,MGI:1346018,MGI:1347465,MGI:1349410,MGI:1350935,M
GI:1351502,MGI:1351660,MGI:1352466,MGI:1352630,MGI:1352747,MGI:1354178,MGI:1858223,MGI:1859152,M
GI:1859665,MGI:1861676,MGI:1888971,MGI:1890616,MGI:1914229,MGI:1914292,MGI:1914345,MGI:1914792,M
GI:1915416,MGI:1916264,MGI:1916320,MGI:1916847,MGI:1917087,MGI:1917777,MGI:1918177,MGI:1919003,M
GI:1919277,MGI:1919282,MGI:1919663,MGI:1919999,MGI:1920081,MGI:1921499,MGI:1921622,MGI:1921991,M
GI:1922250,MGI:1923203,MGI:1923707,MGI:1923760,MGI:1925144,MGI:1926134,MGI:1926143,MGI:1928676,M
GI:1929059,MGI:1929468,MGI:1929501,MGI:1930146,MGI:1933157,MGI:1933754,MGI:1933973,MGI:1934582,M
GI:1934860,MGI:2135610,MGI:2143340,MGI:2143424,MGI:2145950,MGI:2146012,MGI:2149728,MGI:2154238,M
GI:2159400,MGI:2179733,MGI:2180756,MGI:2388072,MGI:2389173,MGI:2389180,MGI:2441817,MGI:2443047,M
GI:2443220,MGI:2443695,MGI:2443731,MGI:2444155,MGI:2444169,MGI:2444417,MGI:2444465,MGI:2444563,M
GI:2445179,MGI:2446632,MGI:2448554,MGI:2676830,MGI:2681173,MGI:2685047,MGI:2685177,MGI:2685973,M
GI:3045256,MGI:3512628,MGI:3521816,MGI:3608416,MGI:3618709,MGI:3712326,MGI:87938,MGI:88067,MGI:88
151,MGI:88256,MGI:88275,MGI:88276,MGI:88297,MGI:88346,MGI:88563,MGI:892003,MGI:894645,MGI:95387,M
GI:95457,MGI:95481,MGI:95490,MGI:95606,MGI:95739,MGI:95821,MGI:96238,MGI:96680,MGI:96777,MGI:9679
5,MGI:96928,MGI:97524,MGI:97528,MGI:97531,MGI:97798,MGI:97800,MGI:97801,MGI:97821,MGI:97896,MGI:9
8090,MGI:98251,MGI:98358,MGI:98475,MGI:98488,MGI:98658,MGI:98663,MGI:98729,MGI:98823,MGI:98847,M
GI:99260,MGI:99914

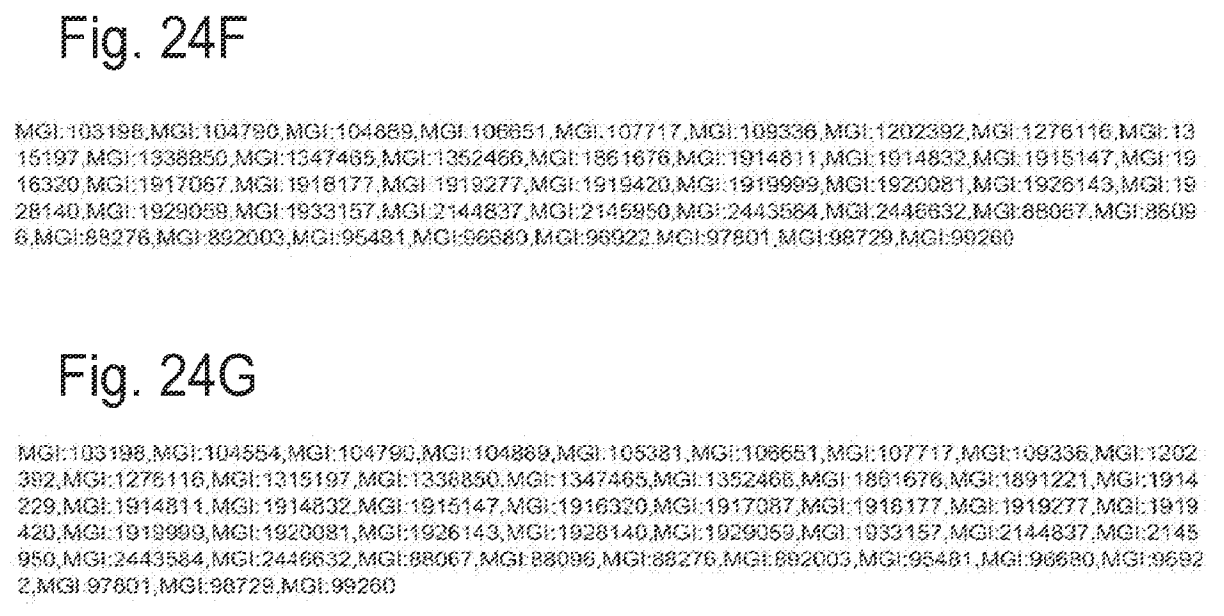

MGI:103198,MGI:104780,MGI:104689,MGI:106651,MGI:107717,MGI:109336,MGI:1202392,MGI:1276116,MGI:13
15197,MGI:1338850,MGI:1347465,MGI:1352466,MGI:1861676,MGI:1914811,MGI:1914833,MGI:1915147,MGI:19
16320,MGI:1917067,MGI:1918177,MGI:1919277,MGI:1919420,MGI:1919999,MGI:1920081,MGI:1926143,MGI:19
28140,MGI:1929059,MGI:1933157,MGI:2144837,MGI:2145960,MGI:2443584,MGI:2446652,MGI:97801,MGI:98260
6,MGI:98276,MGI:892003,MGI:95481,MGI:96680,MGI:98823,MGI:98729,MGI:99260

Fig. 24G

MGI:103198,MGI:104554,MGI:104790,MGI:104869,MGI:105481,MGI:106651,MGI:107717,MGI:109336,MGI:1202
392,MGI:1276116,MGI:1315197,MGI:1338850,MGI:1347465,MGI:1352466,MGI:1861676,MGI:1891221,MGI:1914
229,MGI:1914811,MGI:1914832,MGI:1915147,MGI:1916320,MGI:1917087,MGI:1918177,MGI:1919277,MGI:1919
420,MGI:1919999,MGI:1920081,MGI:1926143,MGI:1928140,MGI:1929059,MGI:1933157,MGI:2144837,MGI:2145
960,MGI:2443584,MGI:2446652,MGI:88067,MGI:88276,MGI:882003,MGI:95481,MGI:96680,MGI:97801,MGI:9859
2,MGI:97801,MGI:98729,MGI:99260

Figure 25 CONT.

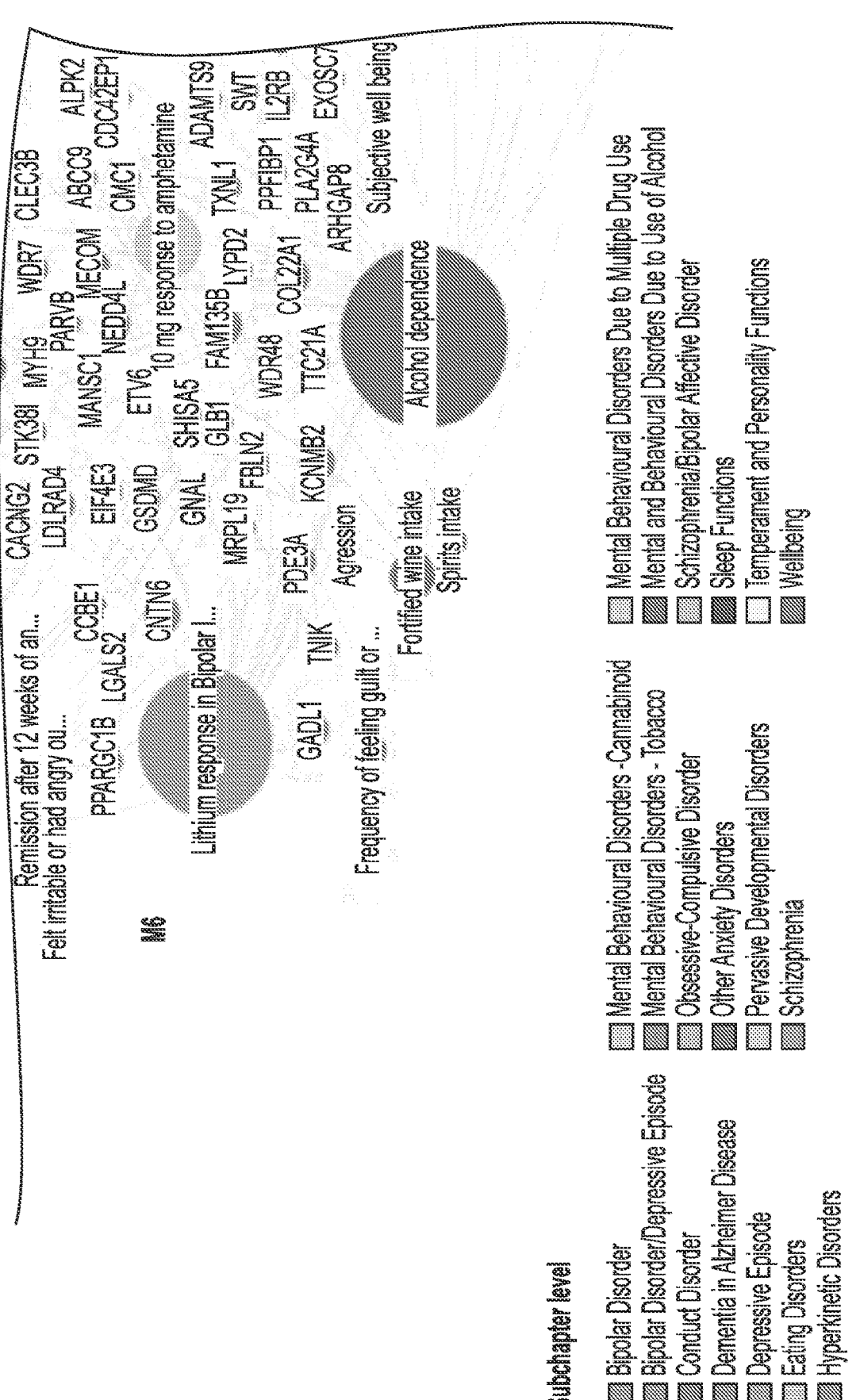

Subchapter level

- Bipolar Disorder
- Bipolar Disorder/Depressive Episode
- Conduct Disorder
- Dementia in Alzheimer Disease
- Depressive Episode
- Eating Disorders
- Hyperkinetic Disorders
- Mental Behavioural Disorders - Cannabinoid
- Mental Behavioural Disorders - Tobacco
- Obsessive-Compulsive Disorder
- Other Anxiety Disorders
- Pervasive Developmental Disorders
- Schizophrenia
- Mental Behavioural Disorders Due to Multiple Drug Use
- Mental and Behavioural Disorders Due to Use of Alcohol
- Schizophrenia/Bipolar Affective Disorder
- Sleep Functions
- Temperament and Personality Functions
- Wellbeing

Figure 25 CONT.

ACTION DETECTION USING MACHINE LEARNING MODELS

RELATED APPLICATIONS

This application is the U.S. national phase under 35 U.S.C. § 371 of International Application No. PCT/US2021/050572, filed Sep. 16, 2021, which claims benefit under 35 U.S.C. § 119(e) of U.S. Provisional application Ser. No. 63/078,952, filed Sep. 16, 2020, the disclosures of which are incorporated by reference herein in their entirety.

GOVERNMENT SUPPORT

This invention was made with government support under DA041668 and DA048634 awarded by the National Institutes of Health. The government has certain rights in the invention.

FIELD OF THE INVENTION

The invention, in some aspects, relates to use of neural networks to detect actions of subjects, in part for use in assessing genetic variation.

BACKGROUND

Behavior, the primary output of the nervous system, is complex, hierarchical, dynamic, and high dimensional (Gomez-Marin, et al., 2014 Nature Neuroscience 17(11): 1455-1462.) Modern approaches to dissect neuronal function require analysis of behavior at high temporal and spatial resolution. Achieving this is a time-consuming task and its automation remains a challenging problem in behavioral neuroscience. Although some efforts have been made to integrate methods in the field of computer vision and modern neural network approaches, few aspects of behavioral biological research leverages neural network approaches. This lack of application is often attributed to the high cost of organizing and annotating the datasets or the stringent performance requirements. Even so, behavior recognition within complex environments is still an open challenge in the machine learning community and translatability of proposed solutions to behavioral neuroscience remains unanswered.

Behavioral neuroscientists have traditionally utilized several methods to classify mouse behavior. Simple behaviors such as mouse rearing can be classified using physical measurement devices that detect when a mouse exceeds a certain height. For more complex psychiatric constructs such as motivation, operant behavioral paradigms have been used. Open source systems, like JAABA [Kabra et al., 2013 Nature methods. 2013; 10(1):64], have been used by researchers to train their own machine learning classifiers for complex behaviors using movement and other measurements [Van den Boom, et al., 2017 J. Neuroscience Methods 289:48-56]. These systems are inherently limited by the measurements available, and standard measurements available have only included center of mass tracking, which drastically limit the types of behaviors that can be classified reliably. For mice, more modern systems have integrated floor vibration measurements and depth imaging techniques to enhance behavior detection [Quinn et al., 2003 J. Neurosci. Methods; 130(1):83-92 and Hong et al., 2015 PNAS; 112(38):E5351-E5360]. Some efforts have been made to automate the annotation of grooming using a machine learning classifier, but prior techniques are not robust to animal coat color, lighting conditions, and location of the setup [Van den Boom, et al., 2017 J. Neuroscience Methods 289:48-56]. Recent advances in computer vision also provide general purpose solutions for marker-less tracking in lab animals [Mathis et al., 2018 Nature neuroscience. 2018; 21(9):1281; Pereira et al., 2019 Nature methods. 2019; 16(1):117-125], but examples such as human action detection leaderboards suggest that while the approach of pose estimation is powerful, it routinely underperforms end-to-end solutions that utilize raw video input for action classification [Feichtenhofer et al. 2019 Proceedings of the IEEE International Conference on Computer Vision; 2019. p. 6202-6211; Choutas et al., 2018 Proceedings of the IEEE Conference on Computer Vision and Pattern Recognition; 2018. p. 7024-7033].

Previous attempts to operate directly on visual data have been limited to unsupervised behavioral clustering approaches [Todd et al., 2017 Physical Biology 14(1): 015002]. Prior efforts contained limitations on environmental control that are critical towards the ability for the algorithm to function. Various prior systems rely heavily upon alignment of data from a top-down view, see [Berman et al., 2014 J. of The Royal Society Interface 11(99): 20140672; Wiltschko et al., 2015 Neuron 88(6):1121-1135]. Although these approaches can cluster similar video segments, labeling the behavior for generated clusters is still dictated by the user, and thereby is significantly limited.

SUMMARY OF THE INVENTION

According to an aspect of the invention, a computer-implemented method is provided, the method including: receiving video data representing a video capturing movements of a subject; identifying a first set of frames from the video data; determining a rotated set of frames by rotating the first set of frames; processing the first set of frames using a first trained model configured to identify a likelihood of the subject exhibiting a predetermined behavioral action; based on the processing of the first set of frames by the first trained model, determining a first probability of the subject exhibiting the predetermined behavioral action in a first frame of the first set of frames, the first frame corresponding to a time duration of the video data; processing the rotated set of frames using the first trained model; based on the processing of the rotated set of frames by the first trained model, determining a second probability of the subject exhibiting the predetermined behavioral action in a second frame of the rotated set of frames, the second frame corresponding to the time duration of the first frame; and using the first probability and the second probability, identifying a label for the first frame, the first label indicating that the subject exhibits the predetermined behavioral action. In some embodiments, the method also includes: processing the first set of frames using a second trained model configured to identify a likelihood of the subject exhibiting the predetermined behavioral action; based on the processing of the first set of frames by the second trained model, determining a third probability of the subject exhibiting the predetermined behavioral action in the first frame; processing the rotated set of frames using the second trained model; based on the processing of the rotated set of frames by the second trained model, determining a fourth probability of the subject exhibiting the predetermined behavioral action in the second frame; and identifying the first label using the first probability, the second probability, the third probability and the fourth probability. In certain embodiments, the method also includes: determining a reflected set of frames by reflecting the first set of frames;

processing the reflected set of frames using the first trained model; based on the processing of the reflected set of frames by the first trained model, determining a third probability of the subject exhibiting the predetermined behavioral action a third frame of the reflected set of frames, the third frame corresponding to the first frame; and identifying the first label using the first probability, the second probability, and the third probability. In some embodiments, the predetermined behavioral action includes a grooming behavior. In some embodiments the predetermined behavior action only includes one or more grooming behaviors. In certain embodiments, the subject is a mouse. In certain embodiments, the subject is a mammal, optionally is a rodent, and the predetermined behavior includes a grooming behavior including at least one of: paw licking, unilateral face wash, bilateral face wash, and flank licking. In some embodiments, the first set of frames represent a portion of the video data during a time period, and the first frame is a last temporal frame of the time period. In some embodiments, the method also includes: identifying a second set of frames from the video data; determining a second rotated set of frames by rotating the second set of frames; processing the second set of frames using the first trained model; based on the processing of the second set of frames by the first trained model, determining a third probability of the subject exhibiting the predetermined behavioral action in a third frame of the second set of frames; processing the second rotated set of frames using the first trained model; based on the processing of the second rotated set of frames by the first trained model, determining a fourth probability of the subject exhibiting the predetermined behavioral action in a fourth frame of the rotated set of frames, the fourth frame corresponding to the third frame; and using the third probability and the fourth probability, identifying a second label for the fourth frame, the first label indicating that the subject exhibits the predetermined behavioral action. In certain embodiments, the method also includes: using at least the first label and the second label, generating an ethogram representing the predetermined behavioral action of the subject during a time period. In certain embodiments, the first trained model is a machine learning classifier. In some embodiments, the method also includes, prior to receiving the video data, receiving training data including a first plurality of video frames and a second plurality of video frames, each of the first plurality of video frames associated with a positive label indicating that the subject is exhibiting the predetermined behavioral action and each of the second plurality of video frames associated with a negative label indicating that the subject is exhibiting a behavioral action that is not the predetermined behavior action; processing the training data using a first set of model parameters and first classifier model data to determine the first trained model. In some embodiments, the first plurality of frames and the second plurality of frames represent movements of a plurality of subjects, wherein a subject of the plurality of subjects includes one or more pre-identified physical characteristic(s). In certain embodiments, the pre-identified physical characteristic is one or more of: a body shape, a body size, a coat color, a gender, an age, and a phenotype of a disease or disorder. In some embodiments, the disease or disorder is a heritable disease, an injury, or a contagious disease. In some embodiments, the first plurality of frames and the second plurality of frames represent movements of a plurality of mice subjects, a mouse of the plurality of mice having a coat color, a gender, a body shape and a size. In certain embodiments, the subject is a mammal. In some embodiments, the subject is a genetically engineered subject, optionally a genetically engineered rodent. In some embodiments, the subject is a genetically engineered mouse.

According to another aspect of the invention, a computer-implemented method is provided, the method including: receiving video data representing a video capturing movements of a subject; identifying a first set of frames from the video data; processing the first set of frames using a first trained model configured to identify a likelihood of the subject exhibiting a predetermined behavioral action; based on the processing of the first set of frames by the first trained model, determining a first probability of the subject exhibiting the predetermined behavioral action in a first frame of the first set of frames; processing the first set of frames using a second trained model configured to identify a likelihood of the subject exhibiting the predetermined behavioral action; based on the processing of the first set of frames by the second trained model, determining a second probability of the subject exhibiting the predetermined behavioral action in the first frame; and using the first probability and the second probability, identifying a first label for the first frame, the first label indicating that the subject exhibits the predetermined behavioral action. In certain embodiments, the method also includes: determining a rotated set of frames by rotating the first set of frames; processing the rotated set of frames using the first trained; based on the processing of the rotated set of frames by the first trained model, determining a third probability of the subject exhibiting the predetermined behavioral action in the second frame of the rotated set of frames, the second frame corresponding to the first frame; processing the rotated set of frames using the second trained model; based on the processing of the rotated set of frames by the second trained model, determining a fourth probability of the subject exhibiting the predetermined behavioral action in the second frame; and identifying the first label using the first probability, the second probability, the third probability and the fourth probability. In certain embodiments, the method also includes: determining a reflected set of frames by reflecting the first set of frames; processing the reflected set of frames using the first trained; based on the processing of the reflected set of frames by the first trained model, determining a third probability of the subject exhibiting the predetermined behavioral action in the second frame of the reflected set of frames, the second frame corresponding to the first frame; processing the reflected set of frames using the second trained model; based on the processing of the reflected set of frames by the second trained model, determining a fourth probability of the subject exhibiting the predetermined behavioral action in the second frame; and identifying the first label using the first probability, the second probability, the third probability and the fourth probability. In some embodiments, the first model and the second model are neural network models, the first model is initialized using a first set of parameters, and the second trained model is initialized using a second set of parameters different than the first set of parameters. In some embodiments, the method also includes: processing the first set of frames using a third trained model configured to identify a likelihood of the subject exhibiting a predetermined behavioral action; based on the processing of the first set of frames by the third trained model, determining a third probability of the subject exhibiting the predetermined behavioral action in the first frame; processing the first set of frames using a fourth trained model configured to identify a likelihood of the subject exhibiting the predetermined behavioral action; based on the processing of the first set of frames by the fourth trained model, determining a fourth probability of the subject exhibiting the predetermined behavioral action in the first frame; and identifying the first label using the first probability, the second probability, the third probability, and the fourth probability. In some embodiments, the subject is a mammal. In certain embodiments, the predetermined behavioral action includes a grooming behavior. In some embodiments, the predetermined behavioral action includes other than a grooming behavior. In certain embodiments, the subject is a mammal, the pre-determined behavioral action includes a grooming behavior, and the grooming behavior is at least one of: paw licking, unilateral face wash, bilateral face wash, and flank licking. In some embodiments, the subject is a rodent, the pre-determined behavioral action includes a grooming behavior, and the grooming behavior is at least one of: paw licking, unilateral face wash, bilateral face wash, and flank licking. In some embodiments, the first set of frames represent a portion of the video data during a time period, and the first frame is a last temporal frame of the time period. In certain embodiments, the method also includes: identifying a second set of frames from the video data; processing the second set of frames using the first trained model; based on the processing of the second set of frames by the first trained model, determining a third probability of the subject exhibiting the predetermined behavioral action in a third frame of the second set of frames; processing the second set of frames using the second trained model; based on the processing of the second set of frames by the second trained model, determining a fourth probability of the subject exhibiting the predetermined behavioral action in the third frame; and using the third probability and the fourth probability, identifying a second label for the third frame, the second label indicating that the subject exhibits the predetermined behavioral action. In some embodiments, the method also includes: using at least the first label and the second label, generating an ethogram representing the predetermined behavioral action of the subject during a time period. In some embodiments, the first trained model and the second trained model are machine learning classifiers. In certain embodiments, the method also includes, prior to receiving the video data, receiving training data including a first plurality of video frames and a second plurality of video frames, each of the first plurality of video frames associated with a positive label indicating that the subject is exhibiting the predetermined behavioral action, and each of the second plurality of video frames associated with a negative label indicating that the subject is exhibiting a behavioral action that is not the predetermined behavior; processing the training data using a first set of model parameters and first classifier model data to determine the first trained model; and processing the training data using a second set of model parameters and second classifier model data to determine the second trained model. In certain embodiments, the first plurality of frames and the second plurality of frames represent movements of a plurality of subjects, wherein a subject of the plurality of subjects includes one or more pre-identified physical characteristic(s). In some embodiments, the pre-identified physical characteristic is one or more of: a body shape, a body size, a coat color, a gender, an age, and a phenotype of a disease or disorder. In some embodiments, the disease or disorder is a heritable disease, an injury, or a contagious disease. In certain embodiments, the first plurality of frames and the second plurality of frames represent movements of a plurality of mice subjects, a mouse of the plurality of mice having a coat color, a gender, a body shape and a size. In some embodiments, the subject is a rodent, and optionally is a mouse. In certain embodiments, the subject is a genetically engineered subject.

According to another aspect of the invention, a method of assessing a predetermined behavioral action in a subject is provided, wherein the pre-determined behavioral action includes a grooming behavior comprising at least one of: paw licking, unilateral face wash, bilateral face wash, and flank licking, and wherein a means of the assessing includes any embodiment of an aforementioned computer-implemented method. In some embodiments, the subject has a predetermined-behavior-associated disease or disorder and optionally is an animal model of the predetermined-behavior-associated disease or disorder. In certain embodiments, the subject is a genetically engineered subject. In some embodiments, the subject is a rodent, and optionally is a mouse. In some embodiments, the mouse is a genetically engineered mouse. In certain embodiments, the method also includes administering a candidate therapeutic agent to the subject, assessing the predetermined behavior in the subject after the administration of the candidate therapeutic agent, comparing the after-administration assessment to a control assessment of the predetermined behavior, wherein a change in the post-administration predetermined behavior compared to the control predetermined behavior identifies an effect of the administered candidate therapeutic agent on the predetermined behavior. In some embodiments, the change includes one or more of: an onset, an increase, a cessation, and a decrease of the predetermined behavior in the subject. In certain embodiments, the candidate therapeutic agent is administered to the subject prior to assessing the predetermined behavior. In some embodiments, the candidate therapeutic agent is administered to the subject simultaneous to assessing the predetermined behavior. In some embodiments, the control assessment of the predetermined behavior is assessment of the predetermined behavior in a control subject monitored with the computer-implemented method. In some embodiments, the control subject is an animal model of the predetermined-behavior-associated disease or disorder. In certain embodiments, the predetermined-behavior-associated disease or disorder is a heritable disease, an injury, or a contagious disease. In some embodiments, the predetermined-behavior-associated disease or disorder is bipolar disorder, dementia, depression, a hyperkinetic disorder, an anxiety disorder, a developmental disorder, a sleep disorder, Alzheimer's disease, Parkinson's disease, or a physical injury. In some embodiments, the control subject is not administered the candidate therapeutic agent. In certain embodiments, the control subject is administered a dose of the candidate therapeutic agent that is different than the dose of the candidate therapeutic agent administered to the subject. In some embodiments, the control result is a result from a previous monitoring of the subject with the computer-implemented method, optionally wherein the previous monitoring of the subject occurs prior to administration of the candidate therapeutic agent. In some embodiments, the monitoring of the subject identifies the predetermined-behavior-associated disease or disorder in the subject. In some embodiments, the monitoring of the subject identifies efficacy of a candidate therapeutic agent to treat the predetermined-behavior-associated disease or disorder.

According to another aspect of the invention, a method of identifying efficacy of a candidate therapeutic agent to treat a predetermined behavior-associated disease or disorder in a subject is provided, the method including: administering to a subject the candidate therapeutic agent and monitoring one or more predetermined behavior actions in the subject, wherein a means of the monitoring includes a computer-implemented method of any embodiment of an aforementioned method, and wherein the pre-determined behavioral action includes a grooming behavior comprising at least one of: paw licking, unilateral face wash, bilateral face wash, and flank licking, and wherein results of the monitoring indicating a change in the predetermined behavior in the subject identifies an efficacy of the candidate therapeutic agent to treat the predetermined behavior-associated disease or disorder. In certain embodiments, the subject has a predetermined-behavior-associated disease or disorder and optionally is an animal model of the predetermined-behavior-associated disease or disorder. In some embodiments, the subject is an animal model of the predetermined behavior-associated disease or disorder. In certain embodiments, the behavior-associated disease or disorder is a heritable disease, an injury, or a contagious disease. In some embodiments, the behavior-associated disease or disorder is bipolar disorder, dementia, depression, a hyperkinetic disorder, an anxiety disorder, a developmental disorder, a sleep disorder, Alzheimer's disease, Parkinson's disease, or a physical injury. In some embodiments, the subject is a genetically engineered subject. In some embodiments, the subject is a rodent, and optionally is a mouse. In certain embodiments, the mouse is a genetically engineered mouse. In some embodiments, the candidate therapeutic agent is administered to the subject prior to monitoring the predetermined behavior. In some embodiments, the candidate therapeutic agent is administered to the subject simultaneous to monitoring the predetermined behavior. In certain embodiments, the monitored predetermined behavior in the subject is compared to a control monitoring of the predetermined behavior, wherein the control monitoring includes monitoring the predetermined behavior in a control subject with the computer-implemented method. In certain embodiments, the control subject is an animal model of the disease or disorder. In some embodiments, the control subject is not administered the candidate therapeutic agent. In some embodiments, the control subject is administered a dose of the candidate therapeutic agent that is different than the dose of the candidate therapeutic agent administered to the subject. In certain embodiments, the control monitoring is monitoring of the predetermined behavior in the subject with the computer-implemented method at a time prior to administration of the candidate therapeutic agent. In some embodiments, the monitoring of the subject identifies efficacy of the candidate therapeutic agent to treat a predetermined-behavior-associated disease or disorder.

BRIEF DESCRIPTION OF THE DRAWINGS

For a more complete understanding of the present disclosure, reference is now made to the following description taken in conjunction with the accompanying drawings.

FIG. 3 is a conceptual diagram illustrating how the different set(s) of frames may be processed using another trained model; according to embodiments of the present disclosure FIG. 4 is a conceptual diagram illustrating how the different predictions may be processed to determine a final prediction regarding the subject exhibiting the behavior.

FIG. 6 is a conceptual diagram illustrating components for training/configuring a machine learning (ML) model to determine if the subject is exhibiting the behavior during a frame(s) of the video data.

FIG. 7 is a conceptual diagram of a process for analyzing video data 104 of a subject(s) to detect subject behavior, according to embodiments of the present disclosure.

FIG. 8A illustrates that mouse grooming contains a wide variety of postures. Paw licking, face-washing, flank linking, as well as other syntaxes all contribute to this visually diverse behavior. FIG. 8B is an image of grooming ethograms for 6 videos by 5 different trained annotators (Observers 1-5, shown sequentially top to bottom for each ethogram for each video). Overall, there was very high agreement between annotators. FIG. 8C-D show results that quantify the agreement overlap between individual annotators. The average agreement between all annotators was 89.13%.

FIG. 9A-C shows schematics providing additional details of annotator disagreements. FIG. 9A diagrams how types of annotation disagreement were classified into three classes of errors: missed bouts, misalignment, and skipped breaks. FIG. 9B-C shows quantification of the types of errors in FIG. 8A-D. FIG. 9B shows the sum of frames that fell into each error category. 37.5% of frames were missed bouts, 50% of were misalignment, and 12.4% were skipped breaks. The types of errors were not uniformly distributed across annotators as annotator 2 accounts for the most missed bout frame counts, annotator 4 accounts for the most misalignment frame counts, and annotator 1 accounts for the most skipped break frame counts. FIG. 9C shows results of counting the number of multi-frame occurrences of errors, from which a similar distribution was observed with 19.2% of call were missed bouts, 74.6% were misalignment, and 6.3% were skipped breaks.

FIG. 10A-C shows a pie chart and schematic diagrams illustrating embodiments of the invention. FIG. 10A shows a pie chart illustration distribution of mouse grooming dataset and performance of machine learning algorithms applied to this dataset. A total of 2,637,363 frames were annotated across 1,253 video clips were annotated by two different annotators to create this dataset. The outer ring represents the training dataset distribution while the inner ring represents the validation dataset distribution. In each ring, the gray shaded area with a triangle marker indicates annotator agreement for grooming, the gray shaded area with no marker indicates annotator agreement for not grooming, and the light gray shaded area indicates annotator disagreement. FIG. 10B provides a visual description of the classification approach that was implemented. To analyze an entire video, a sliding window of frames was passed into a neural network. Dark gray shading illustrates time spent grooming; medium gray shading with an asterisk marker illustrates time spent not grooming. FIG. 10C illustrates how the network takes video input and produces a grooming prediction for a single frame.

FIG. 11A illustrates agreement between the annotators while creating the dataset compared to the accuracy of the algorithms predicting on this dataset. Machine learning models were compared against only annotations where the annotators agree. FIG. 11B provides a receiver operating characteristic (ROC) curve for 3 machine learning techniques trained on the training set and applied to the validation set. The final neural network model approach achieved the highest area under curve (AUC) value of 0.9843402. No marker, final neural network approach; open circle, neural network 20% training set; open square, JAABA 20% training set. FIG. 11C provides a visual description of the proposed consensus solution. A 32× consensus approach was used in which 4 separate models were trained and 8 frame viewpoints given to each. To combine these predictions, all 32 predictions were averaged. Although one viewpoint from one model can be wrong, the mean prediction using this consensus improved accuracy. FIG. 11D-E provide images of example frames where the model was correctly predicting grooming and not-grooming behavior.

Figures 13C, 13D:
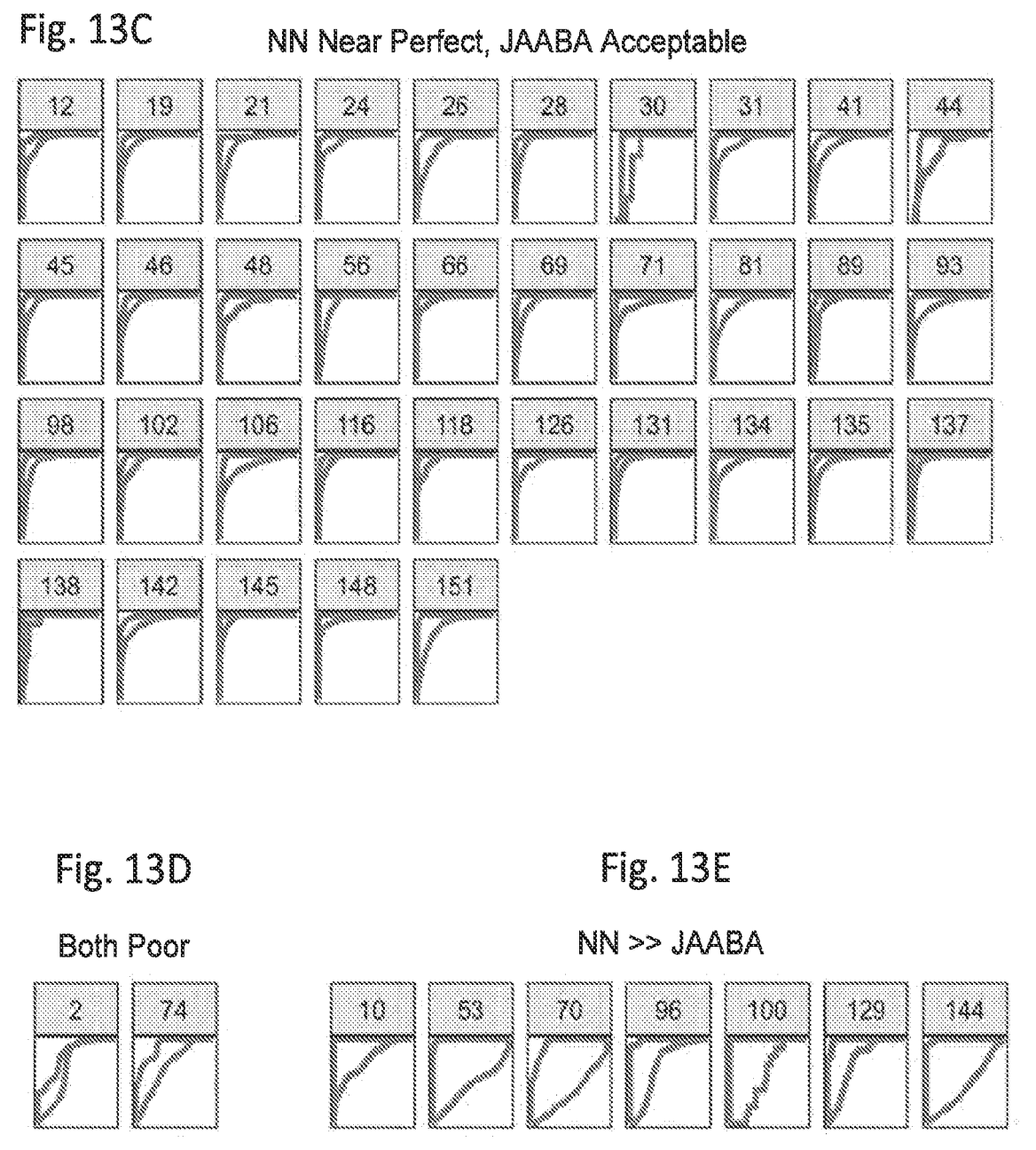

FIG. 13A-E provides graphs of results validating performance of algorithm split by video. The images show clusters of validation video ROC performance by machine learning approaches. FIG. 13A shows results in which the majority of validation videos have good performance. FIG. 13B shows results in which some validation videos suffer from slightly degraded performance. FIG. 13C shows results of validation videos where the JAABA approach performs slightly worse than a neural network approach of the invention. FIG. 13D provides results of two validation videos that showed poor performance using both machine learning approaches. Upon inspection of these videos, the annotated frames for grooming were visually difficult to classify. FIG. 13E provides results of 7 validation videos that showed good performance using the neural network but a clear drop in performance using JAABA. All videos that contained no positive grooming annotated frames did not have a ROC curve and are not shown. In most of the graphs traces of the 4 Model consensus neural network with temporal filter and the JAABA 20% training set are superimposed. In all graphs except graphs 54, 87, 90, 95, 108, 124, and 143, the top/leftmost trace in non-overlapping traces or non-overlapping regions of traces graph indicate the 4 Model consensus neural network with temporal filter and the bottom/rightmost trace indicates the JAABA 20% training set. In graphs 54, 87, 90, 95, 108, 124, and 143, the top/leftmost non-overlapping trace regions indicate the JAABA 20% training set and the bottom/ rightmost non-overlapping trace regions indicate the 4 Model consensus neural network with temporal filter.

FIG. 14A shows ROC performance using different consensus modalities. All consensus modalities provided approximately the same result. Graphed curves: open circle, final neural network approach; no marker, single model; asterisk, vote consensus; triangle marker, mean pre-softmax consensus; open square marker, max pre-softmax consensus; diamond marker, mean consensus; and "X", max consensus.

FIG. 14B shows results of temporal filter analysis. FIG. 15A-C provides a diagram, graph, and table relating to embodiments of the invention. FIG. 15A provides an example grooming ethogram for a single animal. Time is on the x-axis and a shaded bar signifies that the animal was performing grooming behavior during that time. Summaries were calculated at 5, 20, and 55 minute ranges. FIG. 15B provides a visual description of how grooming pattern phenotypes were defined. FIG. 15C provides a table summarizing the all the behavioral metrics analyzed. The phenotypes were grouped into 4 groups, including grooming quantity, grooming pattern, open field anxiety, and open field activity.

FIG. 16A shows results comparing male and female subjects. FIG. 16B shows results comparing testing season, for male and female subjects. FIG. 16C shows results comparing times of day of testing, for male and female subjects. FIG. 16D shows results comparing age at test, in weeks, for male and female subjects. FIG. 16E shows results comparing subjects housed in different rooms, Room of origin. For each room strains shown on graph from left to right are: C57BL/6J F, C57BL/6J M, C57BL/6NJ F, and C57BL/6NJ M. FIG. 16F shows results comparing subjects tested under different illumination levels, lux, for male and female subjects. FIG. 16G shows results comparing subjects tested by different testers, for male and female subjects. FIG. 16H shows results comparing subjects tested with and without white noise during testing, for male and female subjects.

FIG. 17A-F provides images or results of a strain survey of grooming phenotypes with representative ethograms. FIG. 17A shows strain survey results for total grooming time. Strains presented a smooth gradient of time spent grooming, with wild-derived strains showing enrichment on the high end. FIG. 17B provides representative ethograms showing strains with high and low total grooming time. FIG. 17C provides strain survey results for number of grooming bouts. FIG. 17D shows comparative ethograms for two strains with different number of bouts, but similar total time spent grooming. FIG. 17E provides strain survey results for average grooming bout duration. FIG. 17F provides comparative ethograms for two strains with different average bout length, but similar total time spent grooming FIG. 18A-B provided graphs illustrating total grooming and average bout length of different strains over time.

FIG. 19A-C provides plot diagrams of results showing relatedness of grooming phenotypes. FIG. 19A shows results of a strain survey that compared total grooming time and number of bouts. Wild-derived strains and the BTBR strain showed enrichment for having high grooming but low bout numbers. FIG. 19B provides results of a strain survey that compared total grooming time and average bout duration. Most strains that groom more also have a longer average bout length. FIG. 19C provides results of strain survey comparing number of bouts to average bout duration.

FIG. 22A provides heritability estimates of the computed phenotypes. Triangle, activity; filled square, anxiety; diamond, grooming pattern; and dot, grooming quantity. FIG. 22B is a graph showing LD blocks size: Average genotype correlations for single nucleotide polymorphisms (SNPs) in different genomic distances. FIG. 22C provides a Manhattan plot of all of the phenotypes combined, shading is according to peak SNPs clusters, all the SNPs in the same LD block are shaded according to the peak SNP. Minimal p-value over all of the phenotypes for each SNP. FIG. 22D is a heatmap of all the significant SNPs for all the phenotypes. Each row (SNP) is shaded according to the assigned cluster in the k-means clustering. The shading from k-means cluster is used in FIG. 22C.

Figures 24B, 24C:
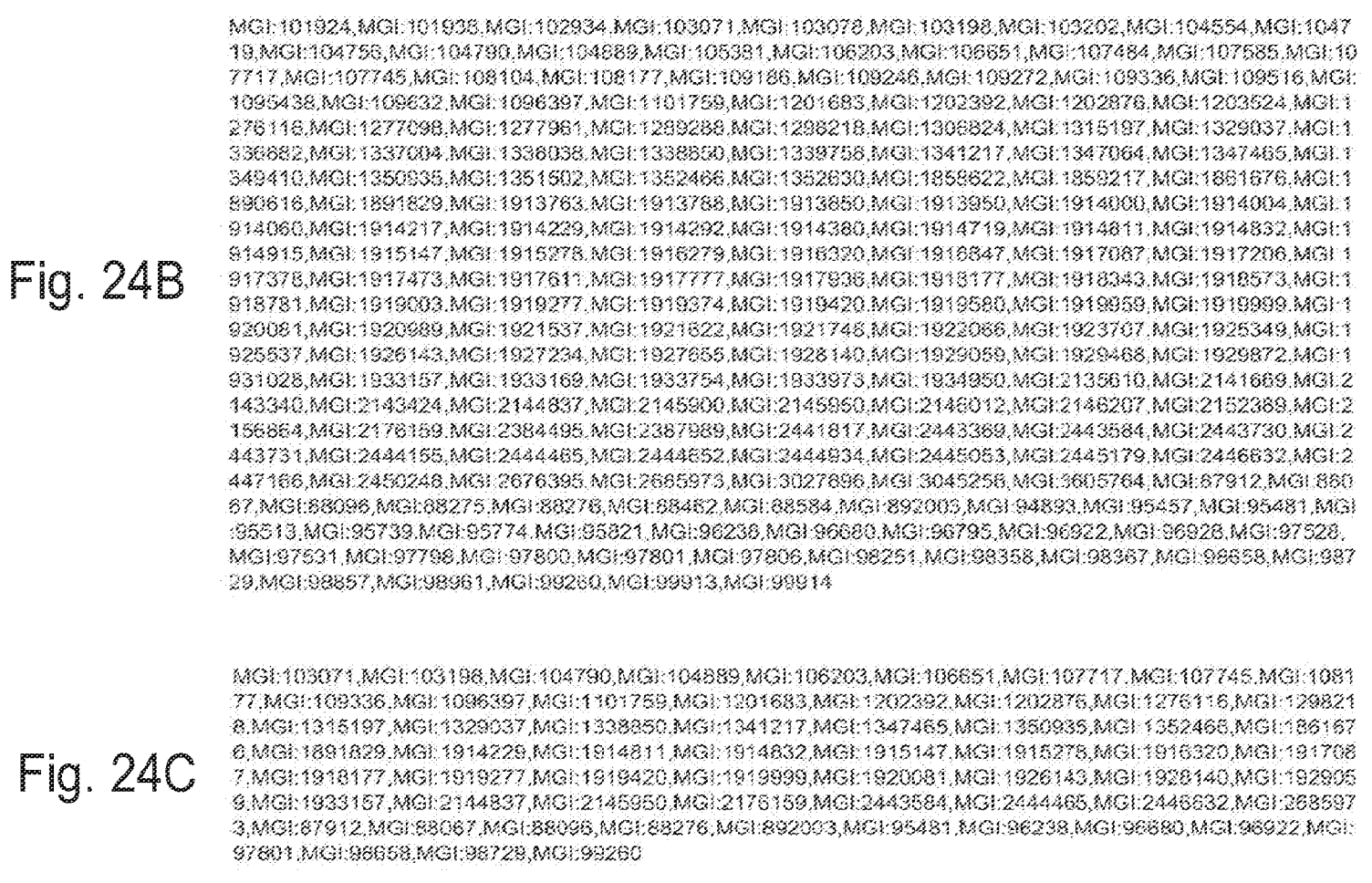

FIG. 24A-G provides data relating to mammalian phenotype ontology enrichment. FIG. 24A shows results for "nervous system phenotype", with $p=7.5\times10^{-4}$, MP:0003631, and 178 genes. FIG. 24B shows results for "preweaning lethality", with $p=3.5\times10^{-3}$, MP:0010770, and 189 genes. FIG. 24C shows results for "abnormal embryo development", with $p=5.5\times10^{-3}$, MP:0001672, and 62 genes. FIG. 24D shows results for "no abnormal phenotype detected", with $p=6.1\times10^{-3}$, MP:0002169, and 102 genes. FIG. 24E shows results for "normal phenotype", with $p=6.5\times10^{-3}$, MP:0002873, and number 102 genes. FIG. 24F shows results for "embryonic growth retardation", with $p=1.1\times10^{-2}$, MP:0003984, and 41 genes. FIG. 24G shows results for "prenatal growth retardation", with $p=1.4\times10^{-2}$, MP:0010865, and 54 genes.

DETAILED DESCRIPTION

Figure 1:
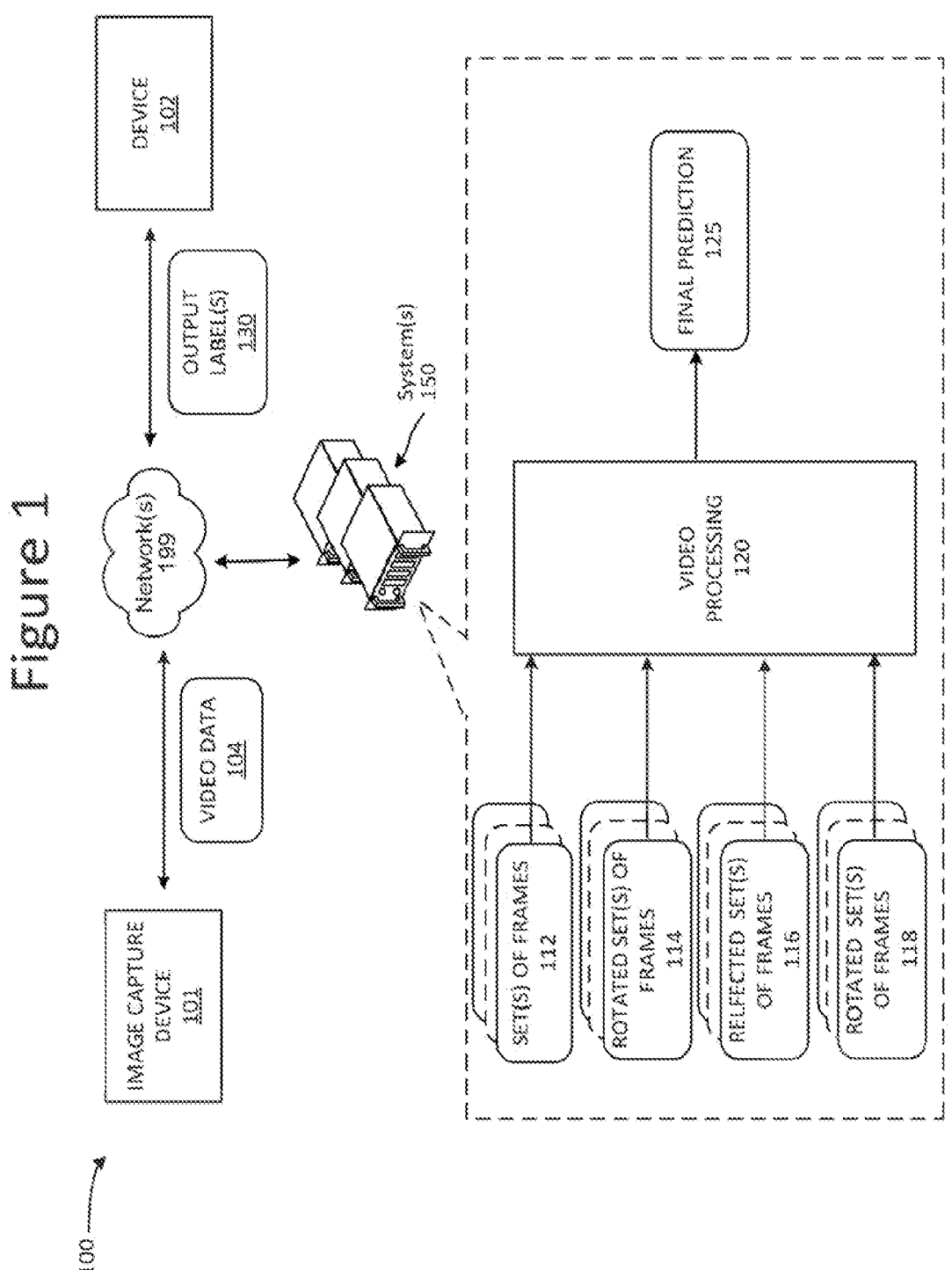
FIG. 1 is a conceptual diagram of a system for determining subject behavior, according to embodiments of the present disclosure.

The invention relates, in part, to methods and systems of using machine learning models (for example, neural networks) to classify behavioral activity, for example, mouse grooming behavior. Grooming represents a form of stereotyped or patterned behavior of considerable biological importance consisting of a range of actions that are very small to very large. Grooming is an innate behavior conserved across animal species, including mammals. In rodents, a significant amount of waking behavior, between 20%-50%, consists of grooming [Van deWeerd H. et al., 2001 Behavioural Processes 53(1-2):11-20; Spruijt B M. et al., 1992 Physiological Reviews 72(3):825-852; and Bolles R C. 1960 Journal of Comparative and Physiological Psychology 53(3):306]. Grooming serves many adaptive functions such as coat and body care, stress reduction, dearousal, social functions, thermoregulation, nociceptive functions, as well as other functions [Spruijt B M. et al., 1992 Physiological Reviews 72(3):825-852; Kalueff A V. et al., Neurobiology of grooming behavior. Cambridge University Press; 2010; and Fentress J C 1988 Annals of the New York Academy of Sciences 525(1):18-26.]. The neural circuitry that regulates grooming behavior has been studied, although much its function remains unknown. Patterned activities, including but not limited to grooming behavior are endophenotypes for many psychiatric illnesses. For instance, high level of stereotyped behavior is seen in autism spectrum disorder (ASD), whereas Parkinson's disease shows an inability to generate patterned behaviors [Kalueff A V. et al., Neurobiology of grooming behavior. Cambridge University Press; 2010]. Certain embodiments of the invention can be used for accurate and automated analysis of behaviors, for assessing diseases and conditions. The term "conditions" is used interchangeably herein with the term "disorders") associated with behavior pattern activities, and/or for identification and use of therapeutics to treat diseases and conditions associated with one or more predetermined behaviors, which are also referred to herein as behavior pattern activities.

The present disclosure describes techniques for detecting a subject's behavior by analyzing video data capturing the subject's behavior. A system may process video data using more than one machine learning (ML) model to generate multiple predictions regarding whether one or more frames in the video data represent the subject exhibiting a defined behavior. These ML models may be configured to detect a particular behavior using training data that includes video capturing movements of a subject(s), where the training data includes labels for each video frame identifying whether the subject is exhibiting the particular behavior or not. Such ML models may be configured using a large training dataset. Based on the configurations of the ML models, the system can be configured to detect different behaviors.

Each of the ML models that processes the video data may be configured using different initialization parameters or settings, so that the ML models may have variations in terms of certain model parameters (such as, learning rate, weights, batch size, etc.), therefore, resulting in different predictions (regarding the subject's behavior) when processing the same video frames.

The system may also process different representations of the video data capturing a subject movements. The system may determine different representations of the video data by modifying the orientation of the video. For example, one orientation may be determined by rotating the video by 90 degrees left, another orientation may be determined by rotating the video by 90 degrees right, and yet another orientation may be determined by reflecting the video along a horizontal or vertical axis. The system may process the video frames in the originally-captured orientation and the other different orientations. Based on processing different orientations, the system may determine different predictions (regarding the subject's behavior) during the same time period.

The different predictions determined as described above may be used to make a final determination regarding whether the subject is exhibiting the behavior in the video frame(s). Aspects of the present disclosure result in improved subject behavior detection. For example, use of different predictions from more than one ML model and from processing different orientations of the video data results in a robust prediction. The configuration of the system enables detecting of subject behavior in different subjects, even when they vary with respect to physical characteristics (such as, size, body shape, color, etc.). Furthermore, the techniques described herein can be used to detect different behaviors.

FIG. 1 conceptually illustrates a system 100 that may be used to detect subject behavior(s) using video data. The system 100 may include an image capture device 101, a device 102 and one or more systems 150 connected across one or more networks 199. The image capture device 101 may be part of, included in, or connected to another device (e.g., device 2600), and may be a camera, a high speed video camera, or other types of devices capable of capturing images and videos. The device 101, in addition to or instead of an image capture device, may include a motion detection sensor, infrared sensor, temperature sensor, atmospheric conditions detection sensor, and other sensors configured to detect various characteristics/environmental conditions. The device 102 may be a laptop, a desktop, a tablet, a smartphone, or other types of computing devices capable of outputting data, and may include one or more components described in connection with device 2600 below.

The image capture device 101 may capture video (or one or more images) of a subject, and may send video data 104 representing the video to the system(s) 150 for processing as described herein. The video may capture movements of the subject (including non-movements of the subject) over a period of time. The system(s) 150 may include one or more components shown in FIG. 1, and may be configured to process the video data 104 to determine behaviors of the subject(s) over time. The system(s) 150 may determine output label(s) 130 associated with one or more frames of the video data 104, where the output label may indicate whether the subject is exhibiting the behavior in the respective frame(s). Data representing the output label(s) 130 may be send to the device 102 for output to a user to observe the results of processing the video data 102.

Details of the components of the system(s) 150 are described below. The various components may be located on the same or different physical devices. Communication between the various components may occur directly or across a network(s) 199. Communication between the device 101, the system(s) 150 and the device 102 may occur directly or across a network(s) 199. One or more components shown as part of the system(s) 150 may be located at the device 102 or at a computing device (e.g., device 2600) connected to the image capture device 102.

The system(s) 150 may determine multiple sets of frames using the video data 104, where the different sets may represent a different orientation of the video data. The set(s) of frames 112 may be the original orientation of video data 104 captured by the image capture device 101. The rotated set(s) of frames 114 may be a rotated orientation of the video data 104, for example, the set(s) of frames 112 may be rotated 90 degrees left to generate the rotated set(s) of frames 114. The reflected set(s) of frames 116 may be a reflected orientation of the video data 104, for example, the set(s) of frames 112 may be reflected across a horizontal axis (or rotated by 180 degrees) to generate the reflected set of frames 116. The rotated set(s) of frames 118 may be another rotated orientation of the video data 104, for example, the set of frames 112 may be rotated 90 degrees right to generate the rotated set(s) of frames 118. In other embodiments, the set of frames 114, 116 and 118 may be generated by manipulating the (original) set(s) of frames 112 in other ways (e.g., reflecting across a vertical axis, rotated by another number of degrees, etc.). In other embodiments, more or fewer orientations of the video data may be processed.

A set of frames 112, 114, 116 and 118 may correspond to the same time period of the video data 104. For example, a first set of frames 112, a first rotated set of frames 114, a first reflected set of frames 116 and a first set of frames 118 may correspond to a first time period, a second set of frames 112, a second rotated set of frames 114, a second reflected set of frames 116 and a second set of frames 118 may correspond to a second time period, and so on.

The system(s) 150 may include a video processing component 120 that may be configured to process the set(s) of frames 112, 114, 116 and 118 to determine final prediction data 125. Details of how the video processing component 120 may process the video data 104 is described below in relation to FIGS. 2-6. The final prediction data 125 may indicate during which frames of the video data 104 the subject is exhibiting the behavior and during which frames the video data 104 the subject is not exhibiting the behavior. In some embodiments, the video processing component 120 may be configured to detect when the subject is exhibiting grooming behavior, which may include paw licking, unilateral face wash, bilateral face wash, and flank licking.

In some embodiments, the final prediction 125 may be used to determine the output label(s) 130, such that data associating an output label 130 with a video frame may be sent to the device 102 (or devices 102). In other embodiments, the final prediction 125 may be used to determine an ethogram representing the subject's behavior during the time period of the video data 104.

Figure 2:
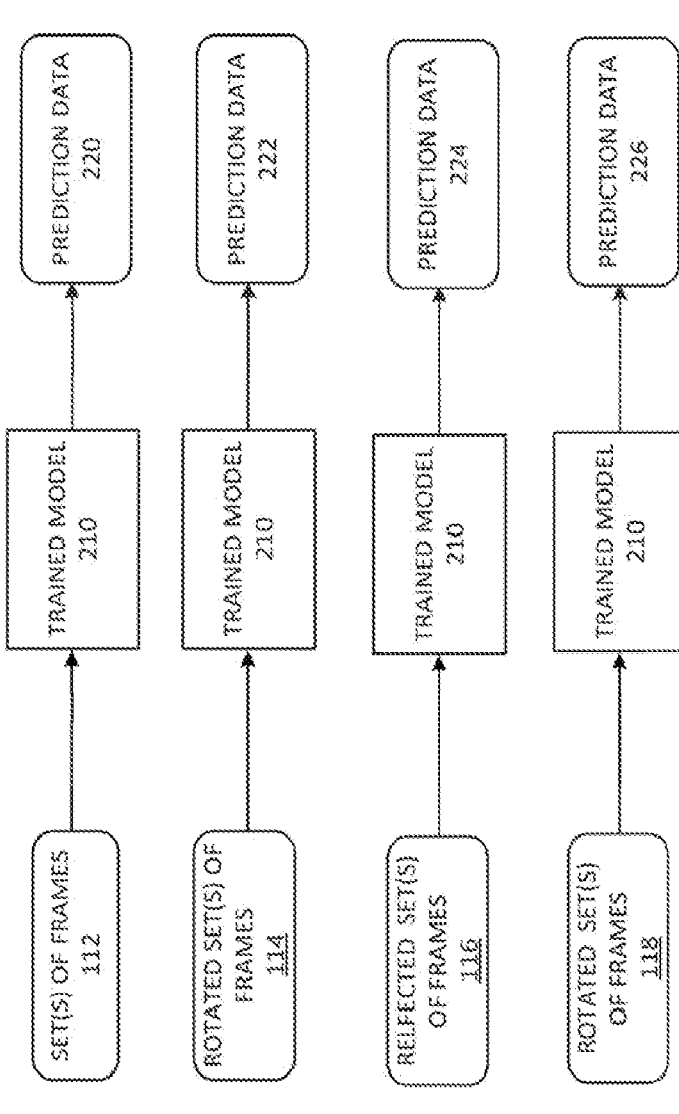
FIG. 2 is a conceptual diagram illustrating a process for analyzing video data of a subject(s) to determine subject behavior, according to embodiments of the present disclosure.

FIG. 2 is a conceptual diagram illustrating how the different set(s) of frames are processed using a trained model. The video processing component 120 may employ one or more trained models, such as, trained model 210. In some embodiments, the trained model 210 may process the set(s) of frames 112 to generate prediction data 220. The prediction data 220 may be a probability or likelihood of the subject exhibiting the behavior during the video represented in the set(s) of frames 112. The trained model 210 may process the rotated set(s) of frames 114 to generate prediction data 222, which may be probability or likelihood of the subject exhibiting the behavior during the video representing in the rotated set(s) of frames 114. The trained model 210 may process the rotated set(s) of frames 116 to generate prediction data 224, which may be probability or likelihood of the subject exhibiting the behavior during the video representing in the rotated set(s) of frames 116. The trained model 210 may process the rotated set(s) of frames 118 to generate prediction data 226, which may be probability or likelihood of the subject exhibiting the behavior during the video representing in the rotated set(s) of frames 118. In this manner, the same trained model 210 may process different orientations of the video data to generate different predictions for the same captured subject movements.

Figure 3:
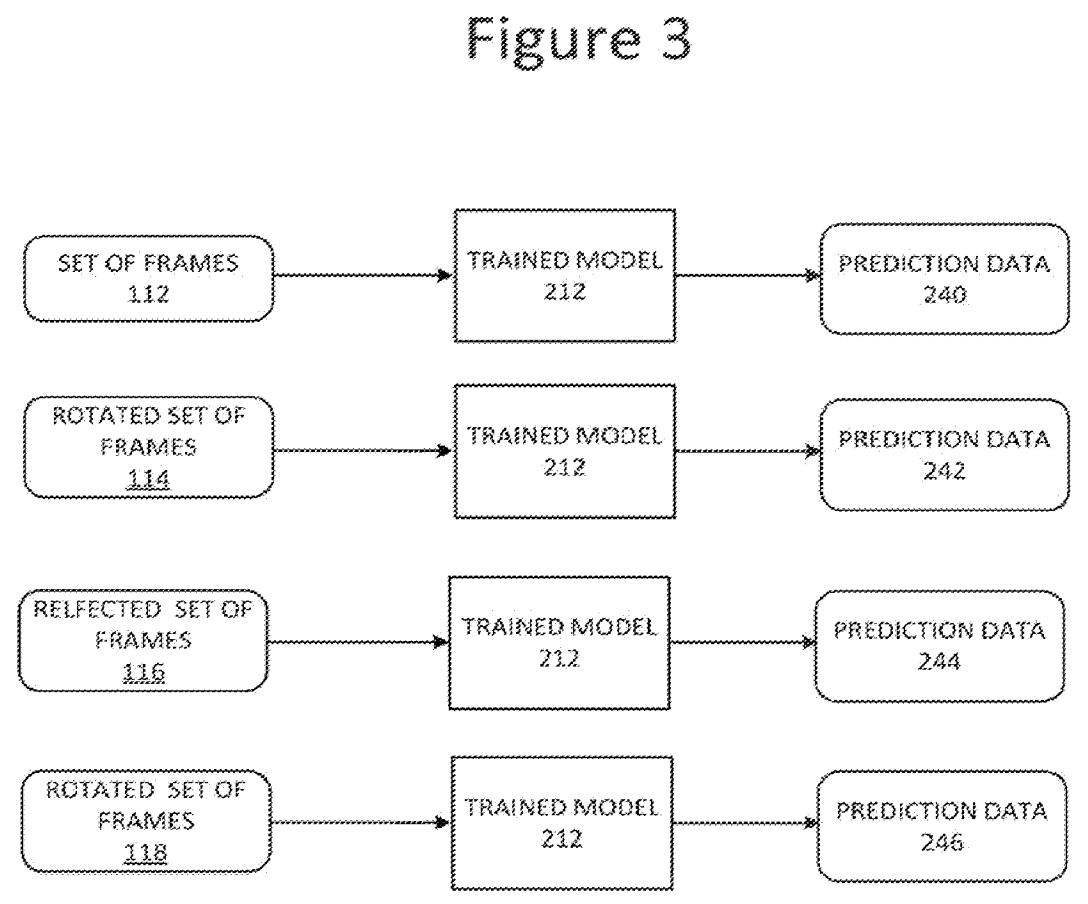

FIG. 3 is a conceptual diagram illustrating how the different set(s) of frames may be processed using another trained model. The video processing component 210 may employ another trained model 212. In some embodiments, the trained model 212 may process the set(s) of frames 112 to generate prediction data 240. The prediction data 240 may be a probability or likelihood of the subject exhibiting the behavior during the video represented in the set(s) of frames 112. The trained model 212 may process the rotated set(s) of frames 114 to generate prediction data 242, which may be probability or likelihood of the subject exhibiting the behavior during the video representing in the rotated set(s) of frames 114. The trained model 212 may process the rotated set(s) of frames 116 to generate prediction data 244, which may be probability or likelihood of the subject exhibiting the behavior during the video representing in the rotated set(s) of frames 116. The trained model 212 may process the rotated set(s) of frames 118 to generate prediction data 248, which may be probability or likelihood of the subject exhibiting the behavior during the video representing in the rotated set(s) of frames 118. In this manner, another trained model 212 may process different orientations of the video data to generate different additional predictions for the same captured subject movements. The probabilities may be a value in the range of 0.0 to 1.0, or a value in the range of 0 to 100, or another numerical range.

Each of the prediction data 220, 222, 224, 226, 240, 242, 244 and 246 may be a data vector including multiple probabilities (or scores), each probability corresponding to a frame of the set(s) 112, 114, 116, 118 respectively, where each probability indicates a likelihood of the subject exhibiting the behavior in the corresponding frame. For example, the prediction data may include a first probability corresponding to a first frame of the video data 104, a second probability corresponding to a second frame of the video data 104, and so on. Each of the prediction data 220, 222, 224, 226, 240, 242, 244 and 246 may be a different probability of the subject exhibiting the behavior during the video represented in the set(s) of frames 112.

In some embodiments, the set(s) of frames 112 may include a number of video frames (e.g., 16 frames), each frame being a duration of video for a time period (e.g., 30 milliseconds, 30 seconds, etc.). Each of the trained model(s) 210 and 212 may be configured to process the set of frames 112 to determine a probability of the subject exhibiting the behavior in the last frame of the set of frames. For example, if there are 16 frames in the set of frames, then the output of the trained model indicates whether or not the subject is exhibiting the behavior in the 16th frame of the set of frames. The trained models 210 and 212 may be configured to use context information from the other frames in the set of frames to make the prediction of the last frame. In other embodiments, the output of the trained models 210 and 212 may determine a probability of the subject exhibiting the behavior in another frame (e.g., middle frame; 8th frame; first frame; etc.) of the set of frames.

FIG. 4 is a conceptual diagram illustrating how the different predictions may be processed to determine a final prediction regarding the subject exhibiting the behavior. The video processing component 120 may include an aggregation component 230 to process the different predictions determined by the different trained models (e.g., 210 and 212) using the different sets of frames (e.g., 112, 114, 116 and 118) to determine the final prediction data 125. The aggregation component 230 may be configured to merge, aggregate or otherwise combine the different prediction data 220, 222, 224, 226, 240, 242, 244 and 246 to determine the final prediction data 125.

In some embodiments, the aggregation component 230 may average the probabilities for the respective frames represented in the prediction data 220, 222, 224, 226, 240, 242, 244 and 246, and the final prediction data 125 may be a data vector of averaged probabilities for each frame in the video data 104. In some embodiments, the video processing component 120 may determine an output label 130 for a frame based on the frame's corresponding averaged probability satisfying a condition (e.g., if the probability is above a threshold probability/value).

In other embodiments, the aggregation component 230 may sum the probabilities for the respective frames represented in the prediction data 220, 222, 224, 226, 240, 242, 244 and 246, and the final prediction data 125 may be a data vector of summed probabilities for each frame in the video data 104. In some embodiments, the video processing component 120 may determine an output label 130 for a frame based on the frame's corresponding summed probability satisfying a condition (e.g., if the probability is above a threshold probability/value).

In some embodiments, the aggregation component 230 may be configured to select the maximum value (e.g., the highest probability) from the prediction data 220, 222, 224, 226, 240, 242, 244 and 246 for the respective frame as the final prediction data 125 for the frame. In other embodiments, the aggregation component 230 may be configured to determine a median value from the prediction data 220, 222, 224, 226, 240, 242, 244 and 246 for the respective frame as the final prediction data 125 for the frame.

In some embodiments, the system(s) 150 may determine a binned value representation of the probabilities in the final prediction data 125. For example, probabilities that fall within a first range of values (e.g., 0-0.33) may be assigned a "low" value/label, probabilities that fall within a second range of values (e.g., 0.34-0.66) may be assigned a "medium" value/label, and probabilities that fall within a third range of values (e.g., 0.67-1.0) may be assigned a "high" value/label. In other embodiments, the binned value representations may be "low", "high-low", "medium", "low-high" and "high".

Figure 5:
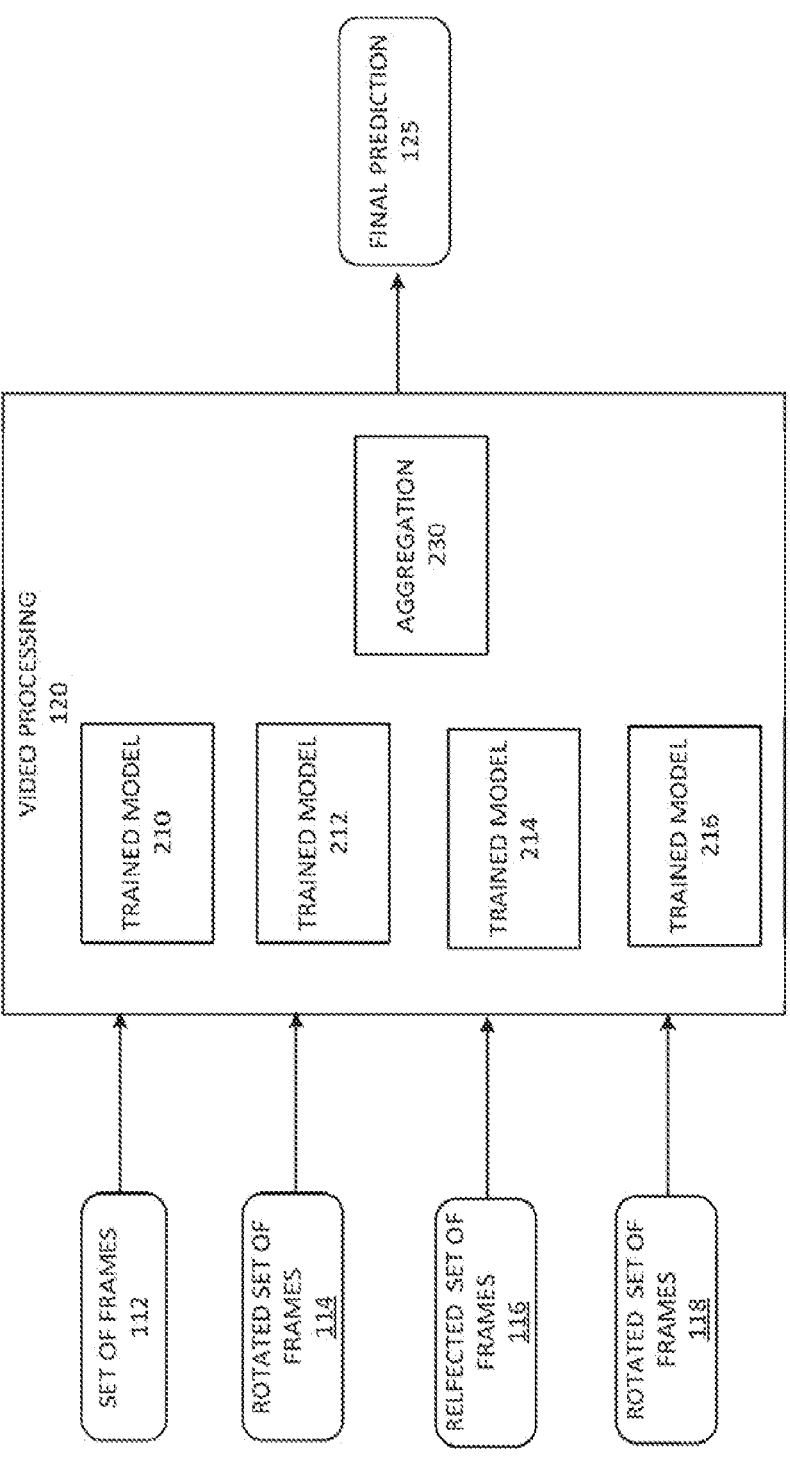
FIG. 5 is a conceptual diagram illustrating a system employing multiple trained models to process different sets of frames.

In some embodiments, the system(s) 150 may apply a temporal smoothing filter over a number of frames (e.g., 46 frames). The temporal smoothing filter may be applied after the system 150 has processed the video data 104 to identify the frames in which the subject is exhibiting the behavior. Temporal smoothing may be used to correct for isolated predictions that may be incorrect, such as, but not limited to: a single frame predicted as "not grooming" inside a grooming bout (where the subject is exhibiting grooming behavior during a period of time, and the frames for that period of time may be labeled as grooming, however, one or two frames may be labeled as not grooming). In some embodiments, temporal smoothing may be functionally a 46-frame rolling average that deters outlier predictions. Alternative temporal smoothing strategies may also be selected and used in combination with methods of the present disclosure. FIG. 5 is conceptual diagram illustrating a system employing multiple trained models to process different sets of frames. Although FIGS. 2 and 3 illustrate using two trained models 210 and 212, as shown in FIG. 5, the video processing component 120 may employ, in some embodiments, four trained models 210, 212, 214 and 216. In other embodiments, the video processing component 120 may employ fewer or more than four trained models.

Each of the trained models 210, 212, 214 and 216 may process each of the set(s) of frames 112, 114, 116 and 118, and may generate 32 different predictions corresponding to a frame and indicating if the subject is exhibiting the behavior in that frame. As described above, the aggregation component 220 may combine the 32 different predictions to determine the final prediction 125.

Figure 6:
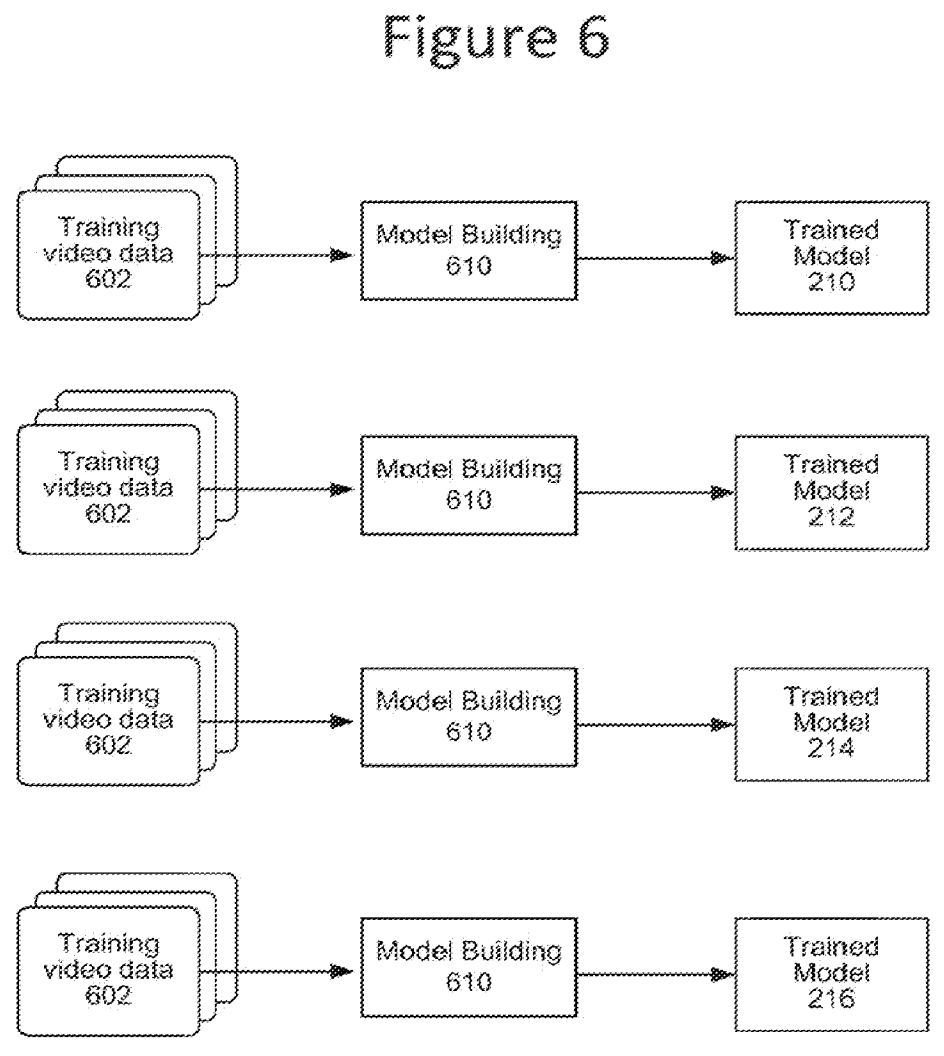

FIG. 6 conceptually illustrates components for training/ configuring a machine learning (ML) model to determine if the subject is exhibiting the behavior during a frame(s) of the video data. As described above, the system(s) 150 may employ multiple trained models (e.g., 210, 212, 214 and 216). Each of the trained models may be trained separately and using different initialization parameters, resulting in different trained models. Because of how the trained models 210, 212, 214 and 216 are trained, each of them may output a different prediction/probability for a frame.

A model building component 610 may train one or more ML models to determine if a user input will result in an error and when a user input should be rephrased. The model building component 610 may train the one or more ML models during offline operations to generate the one or more trained models. The model building component 610 may train the one or more ML models using a training dataset.

In some embodiments, the ML model is a neural network (e.g., convolutional neural network, recurrent neural network, deep learning networks, etc.). The model building component 610 may be provided different initialization parameters to determine the different trained models 210, 212, 214 and 216. The initialization parameters may relate to and define one or more of: initial weights corresponding to one or more layers of the neural network, biases for one or more layers of the neural network, learning rate for the ML model, etc. The model building component 610 may be provided different algorithms or data to determine the different trained models 210, 212, 214 and 216. Such algorithms or data may relate to and define one or more of: an optimization algorithm, a loss function, a batch size, training data, order in which the training data is processed, number of epochs, etc.

In some embodiments, the ML model is a classifier (which may be a neural network based classifier). The classifier may be configured to perform binary classification and determine whether a subject exhibits a behavior or not during a video frame. The classifier may be configured to perform multi-class or multinomial classification and determine whether a subject exhibits a behavior, during a video frame, from a class/category of two or more behaviors. The classifier may be configured to perform multi-label classification and determine whether a subject exhibits one or more behaviors during a video frame.

In some embodiments, the system(s) 150 may include one or more ML models, including but not limited to, one or more classifiers, one or more neural networks, one or more probabilistic graphs, one or more decision trees, and others. In other embodiments, the system(s) 150 may include a rules-based engine, one or more statistical-based algorithms, one or more mapping functions or other types of functions/ algorithms to detect subject behavior.

The training dataset 602 may be video data representing movements of multiple different subjects. In some embodiments, the subject may be a mouse, and the training dataset 602 may be video representing movements of different mice. The training dataset 602 may include video of mice of different body sizes, body shapes, coat color, etc. In this manner, the trained models 210, 212, 214, and 216 may be configured to detect behavior of a mouse subject regardless of the mouse's physical characteristics. The training dataset 602 may include hours of video data so that the ML models are sufficiently trained. The training dataset 602 may include labeled data identifying which frames in the video exhibit the behavior (which may also be referred to herein as a behavioral action, a behavioral activity, a predetermined behavioral activity, or a predetermined behavioral action). In some embodiments, the training dataset 602 includes labeled data identifying when a mouse subject exhibits grooming behavior. In other embodiments, the training dataset 602 may include labeled data identifying when a subject exhibits another predetermined behavioral action.

Methods of the present disclosure can be used to identify and assess grooming behavior and can also be used to detect other "active" behaviors, which may be behaviors that include motions. Non-limiting examples of other behaviors that may be detected and assessed using an embodiment of the present disclosure are: rearing behaviors, running behaviors, jumping behaviors, cognitive behaviors, consciousness behavior, consumption behavior, emission behavior, emotional behavior, impulsive behavior, kinesthetic behavior, motivation behavior, play behavior, reproductive behavior, social behavior, stress-related behavior, rhythmic behavior, and regulation of behavior.

Using the training dataset 602 and a first set of initialization parameters, data, and algorithms, the model building component 610 may configure the first trained model 210. Using the training dataset 602 and a second set of initialization parameters, data, and algorithms, the model building component 610 may configure the second trained model 212. Using the training dataset 602 and a third set of initialization parameters, data, and algorithms, the model building component 610 may configure the third trained model 214. Using the training dataset 602 and a fourth set of initialization parameters, data, and algorithms, the model building component 610 may configure the fourth trained model 216. Once configured, the trained models 210, 212, 214 and 216 may be stored for use during runtime operations, where the video data 104 is processed.

FIG. 7 is a flowchart illustrating a process 700 for analyzing video data 104 of a subject(s) to detect subject behavior, according to embodiments of the present disclosure. The steps of the process illustrated in FIG. 7 may be performed by the system(s) 150. In other embodiments, one or more steps of the process may be performed by the device 102 or a computing device associated with the image capture device 101.

The system(s) 150 receives (702) video data capturing movements of a subject. The system(s) 150 identifies (704) a set of frames from the video data for processing (e.g., 16 frames). The system(s) 150 determines (706) rotated set of frames using the set of frames. For example, the system(s) 150 may rotate the original set of frames by 90 degrees to determine corresponding rotated set of frames. The system(s) 150 determines (708) reflected set of frames using the set of frames. For example, the system(s) 150 may reflect the original set of frames across a horizontal axis to determine corresponding reflected set of frames. The system(s) 150 processes (710) the set of frames, the rotated set of frames and the reflected set of frames using one or more trained models that are configured to detect the subject exhibiting a predetermined behavioral action. The system(s) 150 determines (712), using the output of the one or more trained models, the subject exhibits the behavioral action.

Subjects

Some aspects of the invention include use of automated phenotyping methods with a subject. As used herein, a the term "subject" may refer to a human, non-human primate, cow, horse, pig, sheep, goat, dog, cat, pig, bird, rodent, or other suitable vertebrate or invertebrate organism. In certain embodiments of the invention, a subject is a mammal and in certain embodiments of the invention a subject is a human. In some embodiments a method of the invention may be used in a rodent, including but not limited to a: mouse, rat, gerbil, hamster, etc. In some embodiments of the invention, a subject is a normal, healthy subject and in some embodiments, a subject is known to have, at risk of having, or suspected of having a disease or condition. The terms "subject" and "test subject" may be used interchangeably herein.

As a non-limiting example, a subject assessed with a system and/or method of the invention may be a subject that is an animal model for a disease or condition such as a model for one or more of: bipolar disorder, dementia, depression, a hyperkinetic disorder, an anxiety disorder, a developmental disorder, a sleep disorder, Alzheimer's disease, Parkinson's disease, a physical injury, etc. Additional models of diseases and disorders that may be assessed using a method and/or system of the invention are known in the art, see for example: Barrot M. Neuroscience 2012; 211: 39-50; Graham, D. M., Lab Anim (NY) 2016; 45: 99-101; Sewell, R. D. E., Ann Transl Med 2018; 6: S42. 2019/01/08; and Jourdan, D., et al., Pharmacol Res 2001; 43: 103-110, the contents of which are incorporated herein by reference in their entirety.

In some embodiments a subject may be monitored using an activity determining method or system of the invention and the presence or absence of an activity disorder or condition can be detected. In certain embodiments of the invention, a test subject that is an animal model of an activity and/or movement condition may be used to assess the test subject's response to the condition. In addition, a test subject that is an animal model of a movement and/or activity condition may be administered a candidate therapeutic agent or method, monitored using an activity monitoring method and/or system of the invention and results can be used to determine an efficacy of the candidate therapeutic agent to treat the condition. The terms "activity" and "action" may be used interchangeably herein.

In some embodiments of a method of the invention, a subject is a wild-type subject. As used herein the term "wild-type" means to the phenotype and/or genotype of the typical form of a species as it occurs in nature. In certain embodiments of the invention a subject is a non-wild-type subject, for example, a subject with one or more genetic modifications compared to the wild-type genotype and/or phenotype of the subject's species. In some instances a genotypic/phenopic difference of a subject compared to wild-type results from a hereditary (germline) mutation or an acquired (somatic) mutation. Factors that may result in a subject exhibiting one or more somatic mutations include but are not limited to: environmental factors, toxins, ultraviolet radiation, a spontaneous error arising in cell division, a teratogenic event such as but not limited to radiation, maternal infection, chemicals, etc.

In certain embodiments of methods of the invention, a subject is a genetically modified organism, also referred to as a genetically engineered subject and/or an engineered subject. An engineered subject may include a pre-selected and/or intentional genetic modification and as such exhibits one or more genotypic and/or phenotypic traits that differ from the traits in a non-engineered subject. In some embodiments of the invention routine genetic engineering techniques can be used to produce an engineered subject that exhibits genotypic and/or phenotypic differences compared to a non-engineered subject of the species. As a non-limiting example, a genetically engineered mouse in which a functional gene product is missing or is present in the mouse at a reduced level and a method or system of the invention can be used to assess the genetically engineered mouse phenotype, and the results may be compared to results obtained from a control (control results).

As described elsewhere here, trained models of the invention may be configured to detect behavior of a subject, regardless of the subject's physical characteristics. In some embodiments of the invention, one or more physical characteristics of a subject may be pre-identified characteristics. For example, though not intended to be limiting, a pre-identified physical characteristic may be one or more of: a body shape, a body size, a coat color, a gender, an age, and a phenotype of a disease or disorder.

Diseases and Disorders

Methods and systems of the invention can be used to assess activity and/or behavior of a subject known to have, suspected of having, or at risk of having a disease or condition. In some embodiments, the disease and/or condition is one associated with an abnormal level of an activity or behavior. In a non-limiting example, a test subject that may be subject with anxiety or a subject that is an animal model of anxiety may have one or more activities or behaviors that are associated with anxiety that can be detected using an embodiment of a method of the invention. Results of assessing the test subject can be compared to control results of the assessment, for example of a control subject that does not have anxiety, a control subject that is not a subject that is an animal model of anxiety, a control standard obtained from a plurality of subjects without the condition, etc. Differences in the results of the test subject and the control can be compared. Some embodiments of methods of the invention can be used to identify subjects that have a disease or condition that is associated with abnormal activity and/or behavior. The terms "behavior" and "predetermined behavior" may be used interchangeably herein.

Methods and systems of the invention can be used to assess, determine, and/or monitor one or more predetermined behaviors in a subject. Results from such assessments can be used to assess and/or monitor a predetermined-behavior-associated disease or disorder. The term "predetermined-behavior-associated disease or disorder may be used interchangeably herein with the term "predetermined-behavioral-action-associated disease or condition". Methods and systems of the invention can be used to determine, assess, and/or monitor a behavior that reflect a physical characteristic of the predetermined-behavior-associated disease or disorder. As used herein, the term "predetermined-behavior-associated disease or disorder" means a disease, condition, or disorder that may be characterized by one or more predetermined behaviors that can be assessed using a method or system of the invention. In a non-limiting example, an embodiment of a method of the invention is used to assess a subject known to have or is suspected of having Parkinson's disease or to assess a subject that is an animal model of Parkinson's disease. One or more predetermined behaviors associated with Parkinson's disease are assessed in the subject and the results identify a status of Parkinson's disease in the subject. It will be understood that a result obtained by assessing the subject can be compared to a control assessment and thereby identify a status of the Parkinson's disease in the subject. An embodiment of a method of the invention can be used to determine a status of a predetermined behavior-associated disease or disorder in the subject as present or absent, and can also be used to determine and/or monitor onset, progression, and/or regression of a predetermined-behavior-associated disease or disorder in the subject.

Onset, progression, and/or regression of a disease or a condition associated with an abnormal activity and/or behavior can also be assessed and tracked using embodiments of methods of the invention. For example in certain embodiments of methods of the invention, 2, 3, 4, 7, or more assessments of an activity and/or behavior of a subject are carried out at different times. A comparison of two or more of the results of the assessments made at different times can show differences in the activity and/or behavior of the subject. An increase in a determined level or type of an activity may indicate onset and/or progression in the subject of a disease or condition associated with the assessed activity. A decease in a determined level or type of an activity may indicate regression in the subject of a disease or condition associated with the assessed activity. A determination that an activity has ceased in a subject may indicate the cessation in the subject of the disease or condition associated with the assessed activity.

Certain embodiments of methods of the invention can be used to assess efficacy of a therapy to treat a disease or condition associated with abnormal activity and/or behavior. For example, a test subject may be administered a candidate therapy and methods of the invention used to determine in the subject, a presence or absence of a change in activity associated with the disease or condition. A reduction in an abnormal activity following administration of a candidate therapy may indicate efficacy of the candidate therapy against the disease or condition.

Non-limiting examples of diseases and conditions that are associated with an activity or behavior that can be assessed using a method of the invention are: bipolar disorder, depression, anxiety, eating disorders, hyperkinetic disorders, drug addition, obsessive-compulsive disorders, schizophrenia, Alzheimer's disease, Parkinson's disease, sleep disorders, etc.

Controls and Candidate Compound Testing and Screening

Results obtained for a subject using an activity monitoring method or system of the invention can be compared to control results. Methods of the invention can also be used to assess a difference in a phenotype in a subject versus a control. Thus, some aspects of the invention provide methods of determining the presence or absence of a change in an activity in a subject compared to a control. Some embodiments of the invention include using an embodiment of a method of the invention to identify phenotypic characteristics of a disease or condition and in certain embodiments of the invention automated phenotyping is used to assess an effect of a candidate therapeutic compound on a subject.

Results obtained using a method and/or system of the invention can be advantageously compared to a control. In some embodiments of the invention one or more subjects can be assessed using a method of the invention followed by retesting the subjects following administration of a candidate therapeutic compound to the subject(s). The terms "subject" and "test subject" may be used herein in relation to a subject that is assessed using a method or system of the invention, and the terms "subject" and "test subject" are used interchangeably herein. In certain embodiments of the invention, a result obtained using a method to assess one or more activities in a test subject is compared to results obtained from the methods performed on other test subjects. In some embodiments of the invention a test subject's results are compared to results of the testing performed on the test subject at a different time. In some embodiments of the invention, a result obtained using a method of the invention to assess a test subject is compared to a control result.

As used herein a control result may be a predetermined value, which can take a variety of forms. It can be a single cut-off value, such as a median or mean. It can be established based upon comparative groups, such as subjects that have been assessed using a method and/or system of the invention under similar conditions as the test subject, wherein the test subject is administered a candidate therapeutic agent and the comparative group has not been administered the candidate therapeutic agent. Another example of comparative groups may include subjects known to have a disease or condition and a subject or group of subjects without the disease or condition. Another comparative group may be subjects with a family history of a disease or condition and subjects from a group without such a family history. A predetermined value can be arranged, for example, where a tested population is divided equally (or unequally) into groups based on results of testing. Those skilled in the art are able to select appropriate control groups and values for use in comparative methods of the invention.

A subject assessed using a method or system of the invention may be monitored for the presence or absence of a change that occurs in a test condition versus a control condition. As non-limiting examples, in a subject, a change that occurs may include, but is not limited to one of more of: a frequency of movement, a licking behavior, a response to an external stimulus, etc. Methods and systems of the invention can be used with test subjects to assess the effects of a disease or disorder of the test subject and can also be used to assess efficacy of candidate therapeutic agents.

In some embodiments, a method and/or system of the invention is used to assess a predetermined behavioral action in a subject, and used to assess efficacy and/or effect of a candidate therapeutic agent in the subject. In certain embodiments, the method includes administering a candidate therapeutic agent to the subject, assessing the predetermined behavior in the subject after the administration of the candidate therapeutic agent, comparing the after-administration assessment to a control assessment of the predetermined behavior, wherein a change in the post-administration predetermined behavior compared to the control predetermined behavior identifies an effect of the administered candidate therapeutic agent on the predetermined behavior. In some embodiments the subject has a predetermined-behavior-associated disease or disorder. In some embodiments, the subject is an animal model of the predetermined-behavior-associated disease or disorder.

As a non-limiting example of use of method of the invention to assess the presence or absence of a change in a test subject as a means to identify efficacy of a candidate therapeutic agent, a test subject known to have a behavior-related condition is assessed using a method of the invention. The test subject is then administered a candidate therapeutic agent and assessed again using the method. The presence or absence of a change in the test subject's results indicates a presence or absence, respectively, of an effect of the candidate therapeutic agent on the condition.

It will be understood that in some embodiments of the invention, a test subject may serve as its own control, for example by being assessed two or more times using a method of the invention and comparing the results obtained at two or more of the different assessments. Methods and systems of the invention can be used to assess progression or regression of a disease or condition in a subject, by identifying and comparing changes in phenotypic characteristics in a subject over time using two or more assessments of the subject using an embodiment of a method or system of the invention.

EXAMPLES

Materials and Methods for Examples 1-8
Dataset Annotation

Data was selected to annotate by training a preliminary JAABA classifier for grooming, then clipping video chunks based on predictions for a wide variety of videos. The initial JAABA classifier was trained on 13 short clips that were manually enriched for grooming activity. This classifier is intentionally weak, designed simply to prioritize video clips that would be beneficial to select for annotation. Video time segments with 150 frames surrounding grooming activity prediction were clipped to mitigate chances of a highly imbalanced dataset. 1,253 video clips were generated, with a total 2,637,363 frames. Each video has variable duration, depending upon the grooming prediction length. The shortest video clip contained 500 frames, while the longest video clip contained 23,922 frames. The median video clip length is 1,348 frames.

From here, seven (7) annotators were trained. From this pool of seven trained annotators, two (2) annotators were assigned to annotate each video clip completely. If there was confusion for a specific frame or sequence of frames, the annotators were allowed to request additional opinions. Annotators were required to provide a "Grooming" or "Not Grooming" annotation for each frame, with the intent that difficult frames to annotate would get different annotations from each annotator. Training and validating were done only using frames in which annotators agreed, which reduced the total frames to 2,487,883.

Neural Network Model

The neural network followed a typical feature encoder structure except using 3D convolutions and poolings instead of 2D convolutions. The model was started with a 16×112× 112×1 input video segment, where "16" refers to the time dimension of the input and "1" refers to the color depth (monochrome). Each convolutional layer that was applied was zero-padded to maintain the same height and width dimension. Additionally, each convolutional layer was followed by batch normalization and rectified linear unit (reLU) activation. First applied were two sequential 3D convolutional layers with a kernel size of 3×3×3 and number of filters of 4. Second applied was a max pooling layer of shape 2×2×2 to result in a new tensor shape of 8×64×64×4. This two 3D convolution and max pool was repeated, doubling the filter depth each time, an additional three (3) more times, which resulted in a 1×8×8×32 tensor shape. Two final 3D convolutions with a 1×3×3 kernel size and 64 filter depth were applied, resulting in a 1×8×8×64 tensor shape. Here, the network was flattened to produce a 64×64 tensor. After flattening, two fully connected layers were applied, each with 128 filter depth, batch normalization, and reLU activations. Finally, one more fully connected layer with only 2 filter depth and a softmax activation was added. This final layer was used as the output probabilities for not grooming and grooming predictions.

Neural Network Training

Four (4) individual neural networks were trained using the same training set and four (4) independent initializations. During training, video chunks from the dataset where the final frame contained an annotation where the annotators agree were randomly sampled. Because a 16-frame duration was sampled, this refers to the 16th frame's annotation. If a frame selected did not have 15 frames of video earlier, the tensor was padded with 0-initialized frames. Random rotations and reflections of the data were applied, achieving an 8× increase in effective dataset size. The loss function used in the network was a categorical cross entropy loss, comparing the softmax prediction from the network to a one-hot vector with the correct classification. The Adam optimizer with an initial learning rate of $10^{-5}$ was used. A decay schedule of learning rate was applied to halve the learning rate if 5 epochs persisted without validation accuracy increase. A stop criteria was also employed if validation accuracy did not improve by 1% after 10 epochs. During training, a batch size of 128 example video clips was assembled. Typical training would be done after 13-15 epochs, running for 23-25 epochs without additional improvement.

JAABA Training

Janelia Automatic Animal Behavior Annotator (JAABA) classifiers were trained using two different approaches. A first approach was using the guidelines provided by the software developers. This involved interactively and iteratively training classifiers. The data selection approach was to annotate some data, then prioritize new annotations where the algorithm was unsure or incorrectly making predictions. This interactive training was continued until the algorithm no longer made improvements in a k-fold cross validation.

The second approach was to subset the large annotated dataset to fit into JAABA and train on the agreeing annotations. Initially, utilizing the entire training dataset was attempted, but the machine did not have enough RAM to handle the entire training dataset. The workstation used contained 96 GB of available RAM. A custom program script was written to convert the annotation format to populate annotations in a JAABA classifier file. To confirm the data was input correctly, the annotations from within the JAABA interface were examined. After this file was created, the JAABA classification could be trained using JAABA's interface. After training, the model was applied to the validation dataset to compare with the neural network models. This was repeated this with various sizes of training datasets.

Definition of Grooming Behavioral Metrics

This section describes a variety of grooming behavioral metrics that were in following analyses. Following the approach that [Kalueff A V, et al., Neurobiology of grooming behavior. Cambridge University Press; 2010] set forth, we define a single grooming bout as a duration of continuous time spent grooming without interruption that exceeds 3 seconds. Brief pauses (less than 10 s) were allowed, but no locomotor activity was allowed for this merging of time segments spent grooming. Specifically, a pause occurred when motion of the mouse did not exceed twice its average body length. In order to reduce the complexity of the data, the grooming duration, number of bouts, and average bout duration was summarized into 1-minute segments. In order to have a whole number of bouts per time duration, grooming bouts were assigned to the time segment when a bout begins. In rare instances where multiple-minute bouts occurred, this allowed for a 1-minute time segment to contain more than 1-minute worth of grooming duration.

From here, the total duration of grooming calls in all grooming bouts were summed to calculate the total duration of grooming. Note that this excluded un-joined grooming segments less than 3 s duration as they were not considered a bout. Additionally, the total number of bouts was counted. Once the number of bouts and total duration is determined, the average bout duration was calculated by dividing the two. Finally, the data was binned into one minute time segments and a linear line was fit to the data. Positive slopes for total grooming duration inferred that the individual mouse was increasing its time spent grooming the longer it remained in the open field test. Negative slopes for total grooming duration inferred that the mouse spent more time grooming at the start of the open field test than at the end. This is typically due to the mouse choosing to spend more time doing another activity over grooming, such as sleeping. Positive slopes for number of bouts inferred that the mouse was initiating more grooming bouts the longer it remained in the open field test.

Genome Wide Association Analysis

The phenotypes obtained by the machine learning algorithm for several strains were used to study the association between the genome and the strains behavior. A subset of ten individuals from each combination of strain and sex were randomly selected from the tested mice to ensure equal within group sample sizes. The genotypes of the different strains were obtained from the mouse phenome database (//phenome.jax.org/genotypes). The Mouse Diversity Array (MDA) genotypes were used, di-allele genomes were deduced from parent genomes. SNPs with at least 10% MAF and at most 5% missing data were used, resulting in 222,967 SNPs out of 470,818 SNPs genotyped in the MDA array. LMM method from the GEMMA software package [Zhou and Stephens, 2012 Nature genetics 44(7):821-824] was used for GWAS of each phenotype with the Wald test for computing the p-values. A Leave One Chromosome Out (LOCO) approach was used, each chromosome was tested using a kinship matrix computed using the other chromosomes to avoid proximal contamination. Initial results showed a wide peak in chromosome 7 around the Tyr gene, a well-known coat-color locus, across most phenotypes. To control for this phenomenon, the genotype at SNP rs32105080 was used as a covariate when running GEMMA. Sex was also used as a covariate. To evaluate SNP heritability, GEMMA was used without the LOCO approach. The kinship matrix was evaluated using all the SNPs in the genome and GEMMA LMM output of the proportion of variance in phenotypes explained—the PVE and the PVESE were used as chip heritability and its standard error.

In order to determine the linkage interval, an LD decay was calculated. A selection of 100 snps within a 2.5 MB region was made and the correlation coefficient was calculated. These correlations were binned into 100,000 bp and a threshold $r^2$ of 0.2 was chosen. To determine the peak regions for each phenotype GWAS the SNPs were sorted according to their p-values, then, for each SNP, determining a peak region centered at this SNP by adding other SNPs with high correlation ($r^2 > 0.2$) to the peak SNP. A peak was limited to no larger than 10 million bp from the initial peak SNP selected. These regions were used to find proximate and uncorrelated SNPs in the genome. The peak SNPs were aggregated from all the phenotypes and the p-values from all the phenotypes' GWAS results were used to cluster the peaks into clusters using the k-means algorithm implemented in R. After observing the results, seven clusters were chosen.

To combine the 24 phenotypes tested, the phenotypes were taken from the same group and all of the phenotypes and for each SNP the minimal p-value from the phenotypes in the group was taken.

The significant peaks from each phenotype and aggregated peak regions from all phenotypes assigned to the same cluster were tested for gene ontology (GO) enrichment using INRICH [Lee et al., 2012 Bioinformatics. 2012 04; 28(13): 1797-1799]. The intervals used for gene enrichment were the peak regions described above for each peak SNP. GO annotations related to each gene were obtained from EnsE-BML through biomart interface and the biomaRt R interface [Durinck et al., 2009 Nature Protocols. 2009; 4:1184-1191].

The GWAS execution was wrapped in an R package called mousegwas available on github://github.com/TheJacksonLaboratory/mousegwas, it also includes a singularity container definition file and a nextflow pipeline for regenerating the results.

Example 1

Grooming

Mouse Grooming

Figure 8A:
FIG. 8A-D provides photographs and graphs relating to annotating mouse grooming behavior.

Behavior widely varies in both time and space scales, from fine spatial movements such as whisking, blinking, or tremors to large spatial movements such as turning or walking, and temporally from milliseconds to minutes. A goal of these studies was to develop a classifier that would generalize to complex behaviors seen in the mouse. It was decided to classify grooming because it is conserved across species, and is a neurobiologically important behavior that is of considerable interest [Kalueff et al., Neurobiology of grooming behavior. Cambridge University Press; 2010]. Grooming behavior consists of syntaxes that are small or micro-motions (paw lick) to mid-size movements (unilateral and bilateral face wash) and large movements (flank licking) (FIG. 8A). There are also rare syntaxes such as genital and tail grooming. The length of time of grooming can vary from sub-seconds to minutes. It was reasoned that a successful approach to classifying grooming behavior is important for the neurobiological community and that it would serve as a prototype for other actions.

Annotating Grooming

Figure 8B:
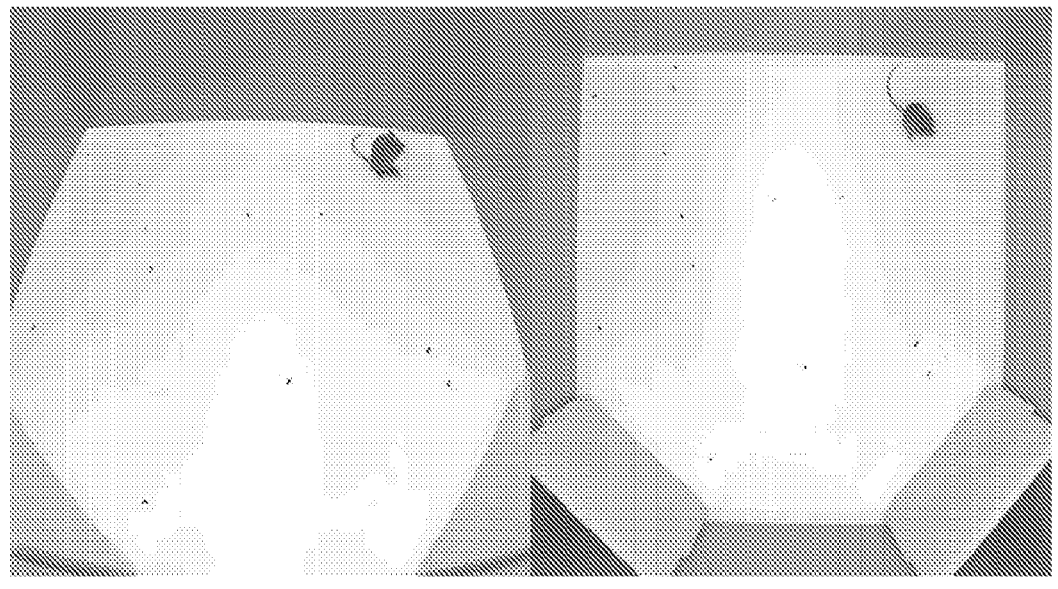
Figure 8C:
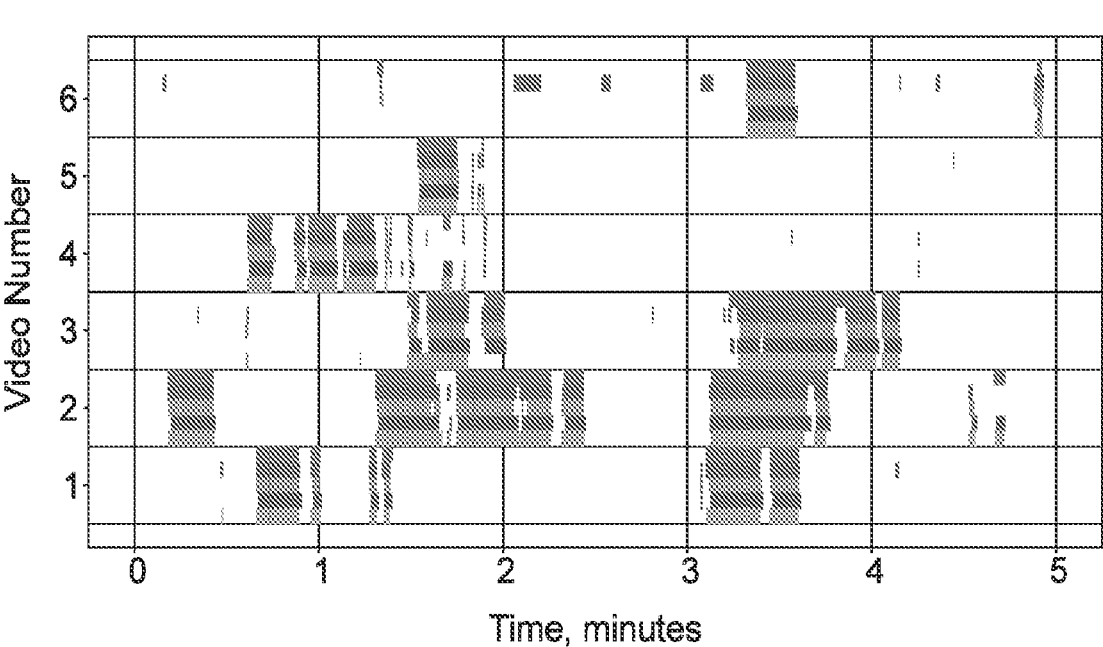
Figure 8D:
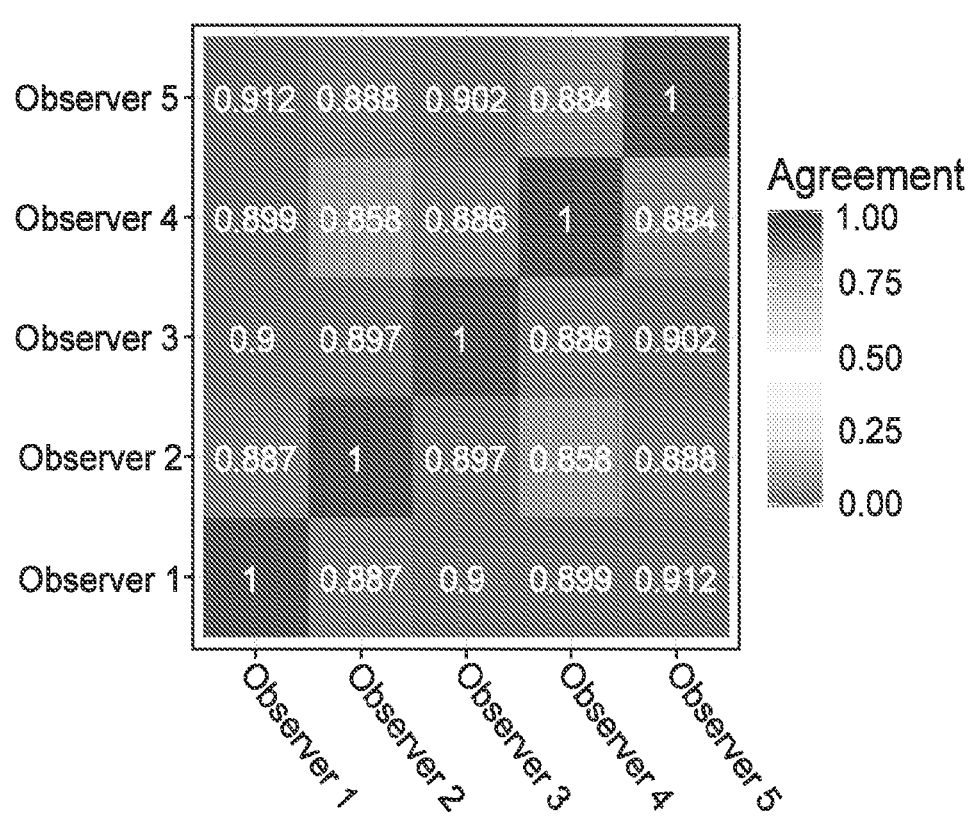

The approach to annotating grooming was by classifying every single frame in a video as the mouse being in one of two states: grooming or not grooming. It was specified that a frame should be annotated as grooming when the mouse was performing any of the syntaxes of grooming, whether or not the mouse is performing a stereotyped syntactic chain of grooming. This explicitly included individual paw licks as grooming, despite individual paw licks not constituting a bout of grooming. Scratching was not a syntax of grooming. This included a wide variety of postures and action duration which contribute to a diverse visual appearance. The variability in human annotation was investigated by tasking five (5) trained annotators with labeling the same six 5-minute videos (30 minutes total, FIG. 8C). To help human scorers, the scorers were provided these three (3) videos from a top-down 140 and side view of the mouse (FIG. 8B). Each annotator was given the same instructions to label the behavior (see Methods above herein). Strong agreement (89.1% average) was observed between annotators. Upon detailed examination of these disagreements between annotators, misclassifications fell into three classes: missed bout, skipped break, and misalignment (FIG. 8A-D and FIG. 9A-C). Missed bout calls were made when a disagreement occurred inside not-grooming call agreement. Similarly, skipped break calls were made when a disagreement occurred inside grooming call agreement. Finally, misalignment was called when both annotators agreed that grooming was either starting or ending but disagreed on the exact frame in which this occurred.

The most frequent type of error was misalignment, accounting for 50% of total duration of disagreement frames annotated and 149 75% of the disagreement calls (FIG. 8A-D and FIG. 9A-C). The observed 89% agreement was in concordance with prior work when annotating mouse grooming behavior [Kyzar et al., 2011 Behavioural Brain Research. 225(2):426-431.] From here, a large annotation dataset was constructed to train a machine learning algorithm. Although most machine learning contests seeking to solve tasks similar to those described herein have had widely varied dataset sizes, the work described herein leveraged network performance in these contests for design of the dataset. Networks in these contests performed well when an individual class contained at least 10,000 annotated frames [Girdhar et al., 2019 Proceedings of the IEEE Conference on Computer Vision and Pattern Recognition; p. 244-253]. As the number of annotations in a class exceeded 100,000, network performance for this task achieved mAP scores above 0.7 [Girdhar et al., 2019 Proceedings of the IEEE Conference on Computer Vision and Pattern Recognition; p. 244-253; Zhang et al. 2019 arXiv preprint arXiv: 190412993]. With deep learning approaches, model performance benefits from additional annotations [Sun et al., 2017 Proceedings of the IEEE International Conference on Computer Vision; p. 843-852.].

Figure 10A:
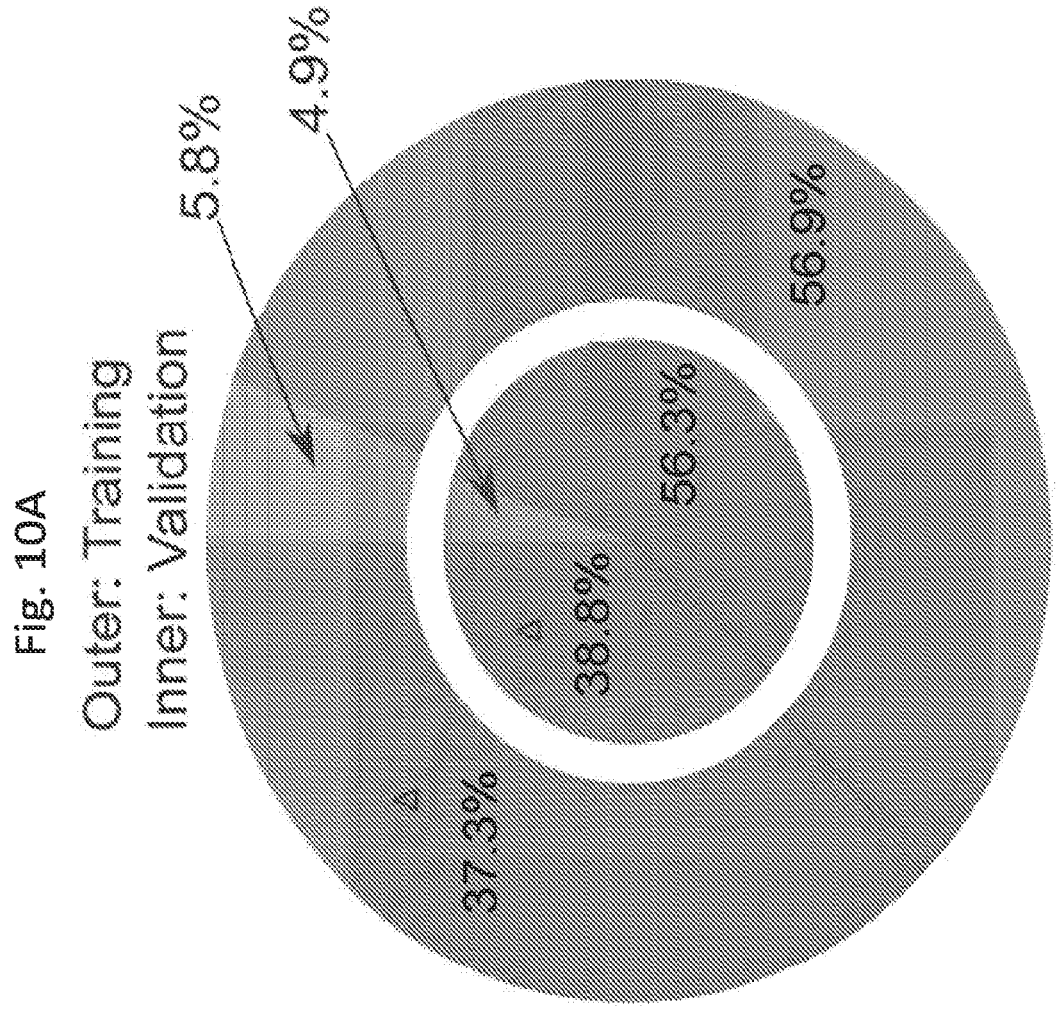

To ensure success, studies described herein set out to annotate over 2 million frames with either grooming or not grooming. A goal was to balance this dataset for grooming behavior by selecting video segments based on tracking heuristics, prioritizing segments with low velocity because a mouse cannot be grooming while walking. In addition, video frames were cropped to be centered on the mouse for reduced visual clutter using the tracker [Geuther et al, 2019 Communications Biology. 2019; 2(1):124]. This cropping that was centered around the mouse followed the video tube approach, as described in Feichtenhofer et al., 2019 *Proceedings of the IEEE International Conference on Computer Vision*; p. 6202-6211. From a pool of seven (7) validated annotators, two (2) annotations were obtained for 1,253 video segments totaling 2,637,363 frames with 94.3% agreement between annotations (FIG. 10A).

Example 2

Proposed Neural Network Solution

Figure 10B:
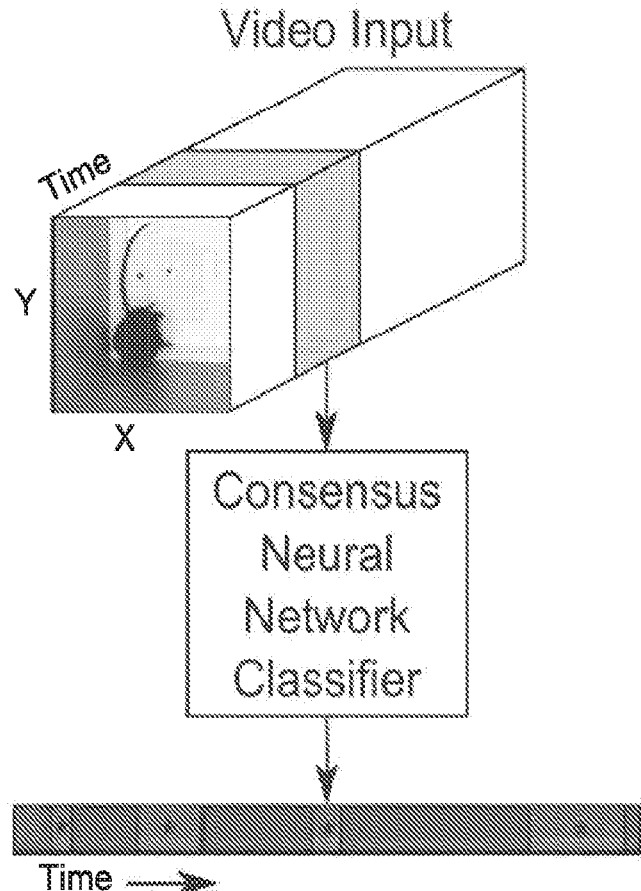
Figure 10C:
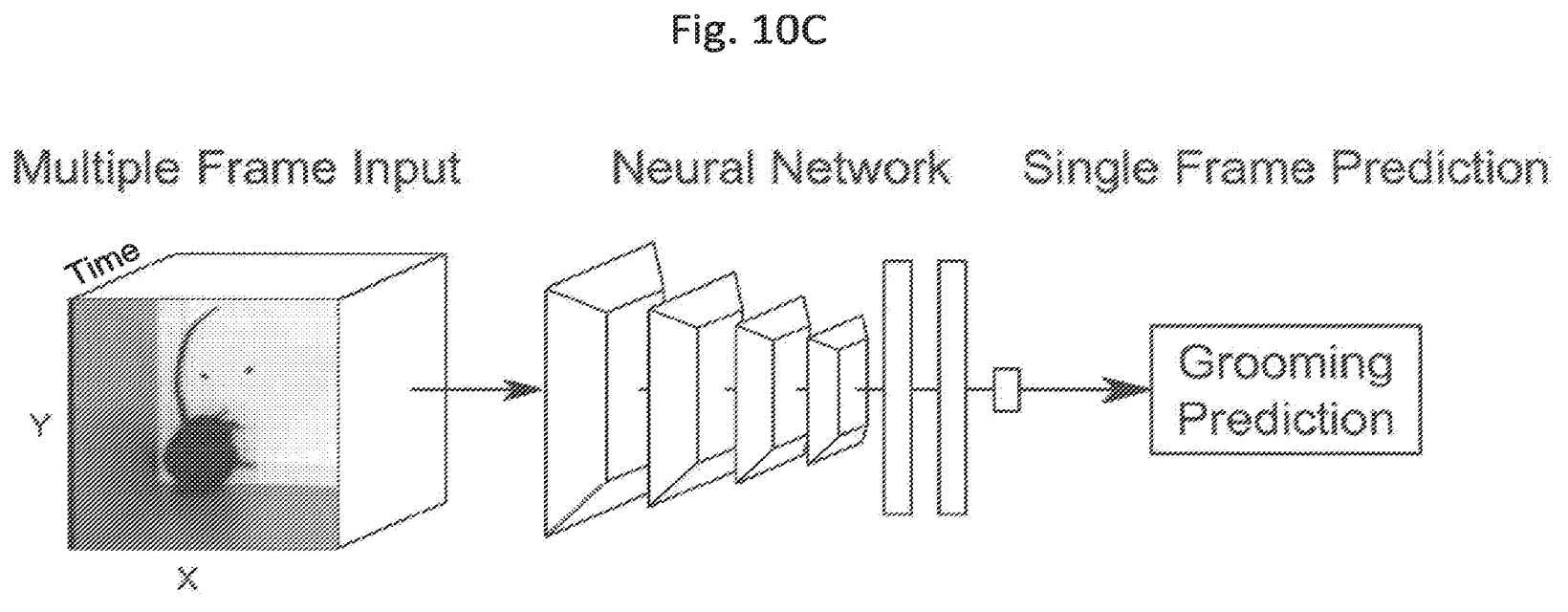

A neural network classifier was trained using a large annotated dataset. Of the 1,253 video segments, 153 video clips were held out for validation. Using this split, it was possible to achieve similar distributions of frame-level classifications between training and validation sets (FIG. 10A). The machine learning approach described herein took video input data and produced an ethogram output for grooming behavior (FIG. 10B). Functionally, the neural network model takes an input of 16 112×112 frames, applies multiple layers of 3D convolutions, 3D pooling, and fully connected layers to produce a prediction for only the last frame (FIG. 10C). To predict a completed ethogram for a video, the process included sliding the 16-frame window across the video. The neural network approach disclosed herein was compared to a previously established machine learning approach for annotating lab animal behavior, JAABA [Kabra et al., 2013 Nature methods. 2013; 10(1):64].

Figure 11A:
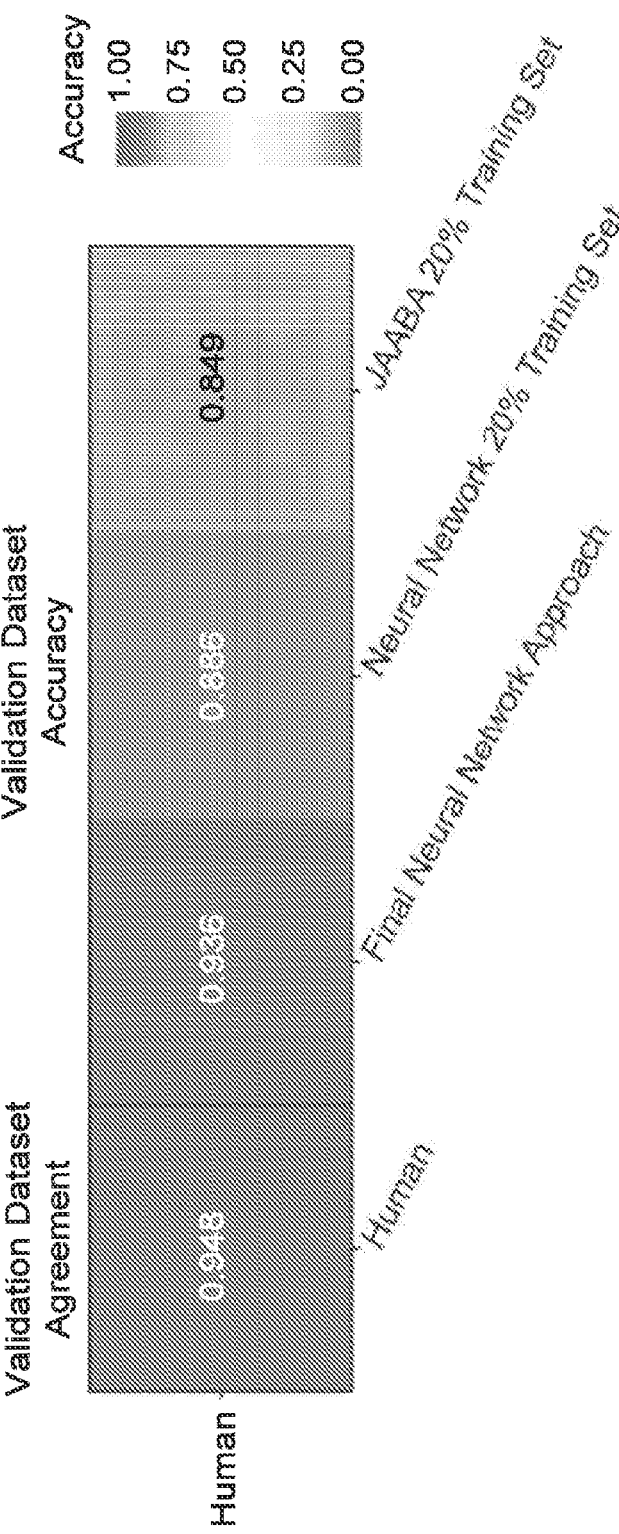
FIG. 11A-E provides graphs, drawings, and photographs illustrating dataset validation studies.

The neural network approach of the invention, achieved the best validation performance for both accuracy and true-positive rate (TPR) at a false-positive rate (FPR) of 5%. The neural network achieved 93.7% accuracy and 91.9% TPR with a 5% 179 FPR (FIG. 11A). In comparison, the JAABA trained classifier achieved a lower performance of 84.9% accuracy and 64.2% TPR at a 5% FPR (FIG. 11A).

Figure 11B:
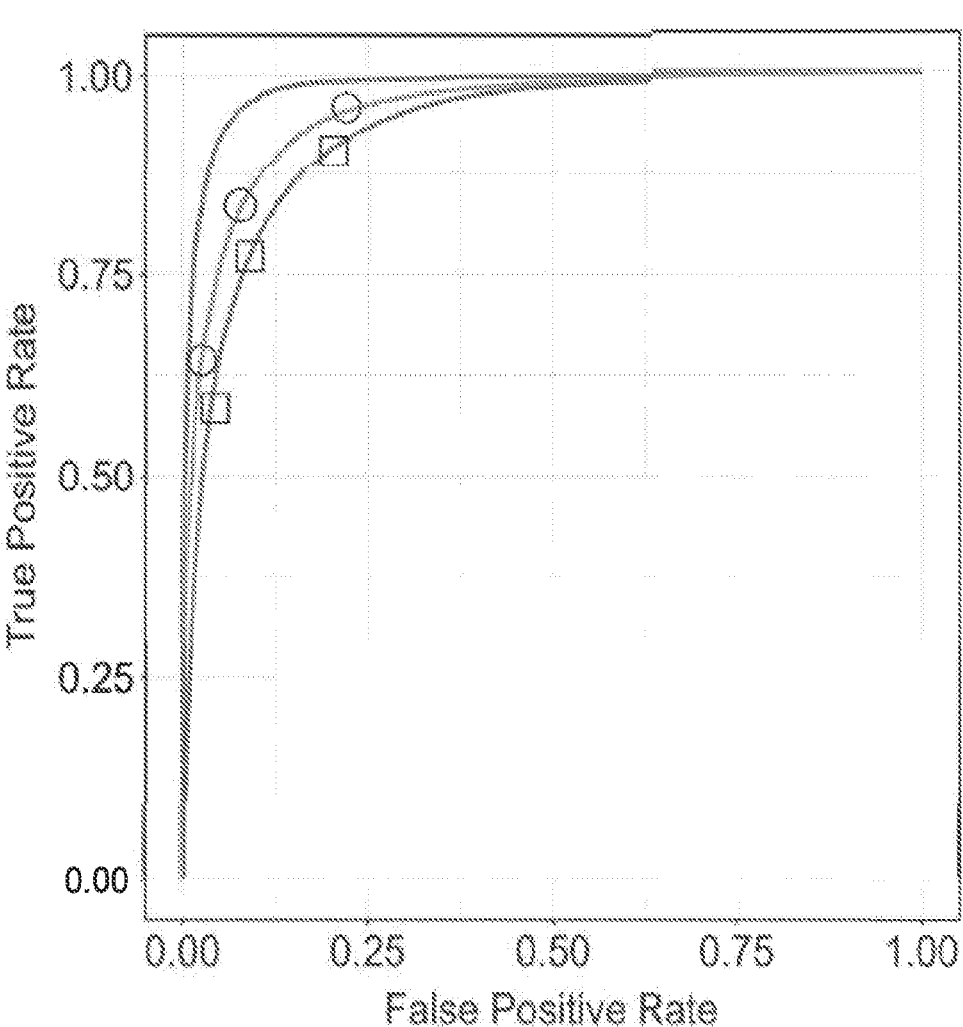
Figure 12:
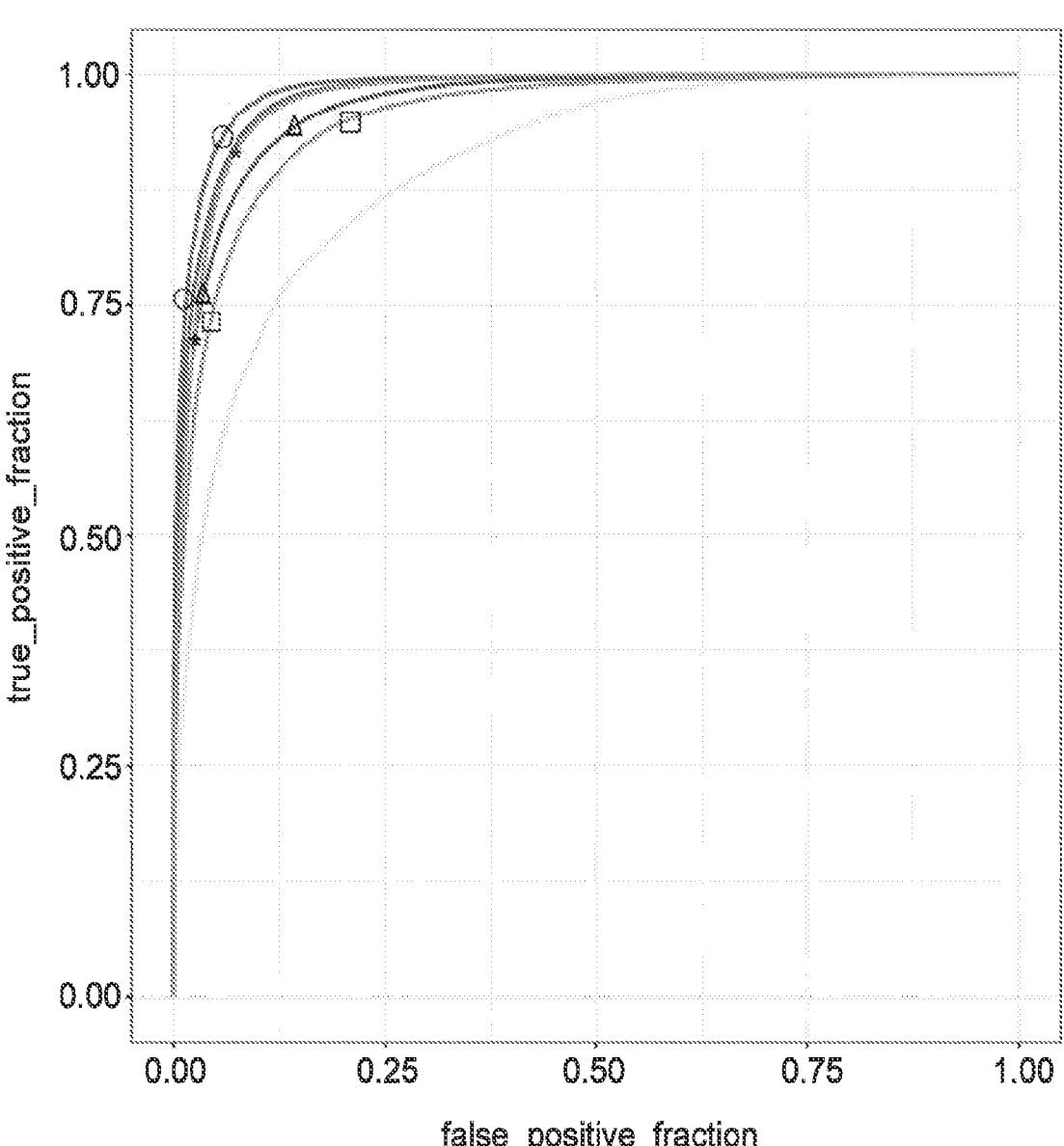
FIG. 12 provides a graph showing results of additional ROC curve subsets. The graph shows performance of the network using different training dataset sizes. Results indicated that as the number of training data samples increased, the ROC curve performance increased up to a point. Graphed curves: open circle, 4 model consensus neural network with temporal filter; no marker, 4 model consensus neural network; medium gray with asterisk, neural network 100% training set; triangle marker, neural network 65% training set; open square marker, neural network 20% training set; and light gray without marker, neural network 10% training set.

Due to memory limitations of JAABA, it was only possible to train using 20% of the training set. A neural network was also trained using an identical training set that JAABA used and the neural network still outperformed JAABA (FIG. 11B). Using different-sized training datasets, improved validation performance were observed with increasing dataset size (FIG. 12). Finally, the authors of JAABA also have a recommended interactive training protocol. Using their interactive training protocol, even poorer performance was observed. This was likely due to the drastic size difference of the annotated datasets used in training (475,000 187 frames vs 17,000 frames). The neural network approach of the invention was as good as human annotators, given previous observations in FIG. 8B-C of 89% agreement.

Figure 11C:
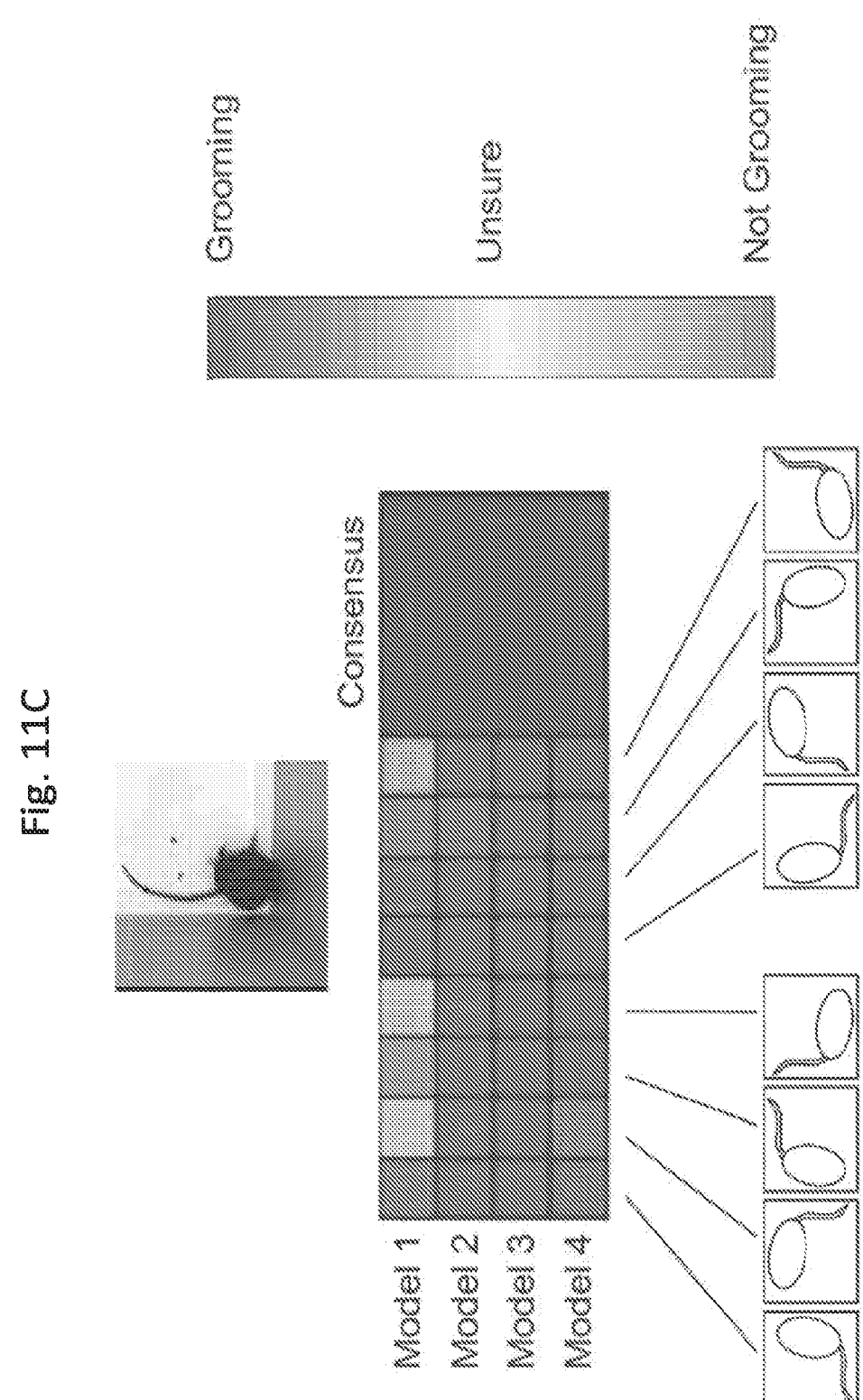

The receiver operating characteristic (ROC) curve performance were inspected on a per-video basis and it was found that performance was not uniform across all videos (FIG. 13A-E). The majority of validation videos were adequately annotated by both the neural network and JAABA. However, two (2) videos performed poorly with both algorithms and seven (7) videos showed drastic improvement using a neural network of the invention over the JAABA trained classifier. Visually inspecting the two (2) videos where both algorithms perform poorly suggested that these particular video clips did not provide sufficient visual information to annotate grooming. While developing the final neural network solution, two forms of consensus modalities were applied to improve single-model performance (FIG. 11C).

Each trained model made slightly different predictions, due to being randomly initialized. By training multiple models and merging the predictions, a slight improvement on validation performance was achieved. Additionally, the input image was also modified for different predictions. Rotating and reflecting the input image appeared visually different for neural networks. Thirty two (32) separate predictions were achieved for every frame by training four (4) models and applying eight (8) rotation and reflection transformations on the input. These individual predictions were merged by averaging the probability predictions. This consensus modality improved the ROC area under the curve (AUC) from 0.975 to 0.978.

Figure 14A:
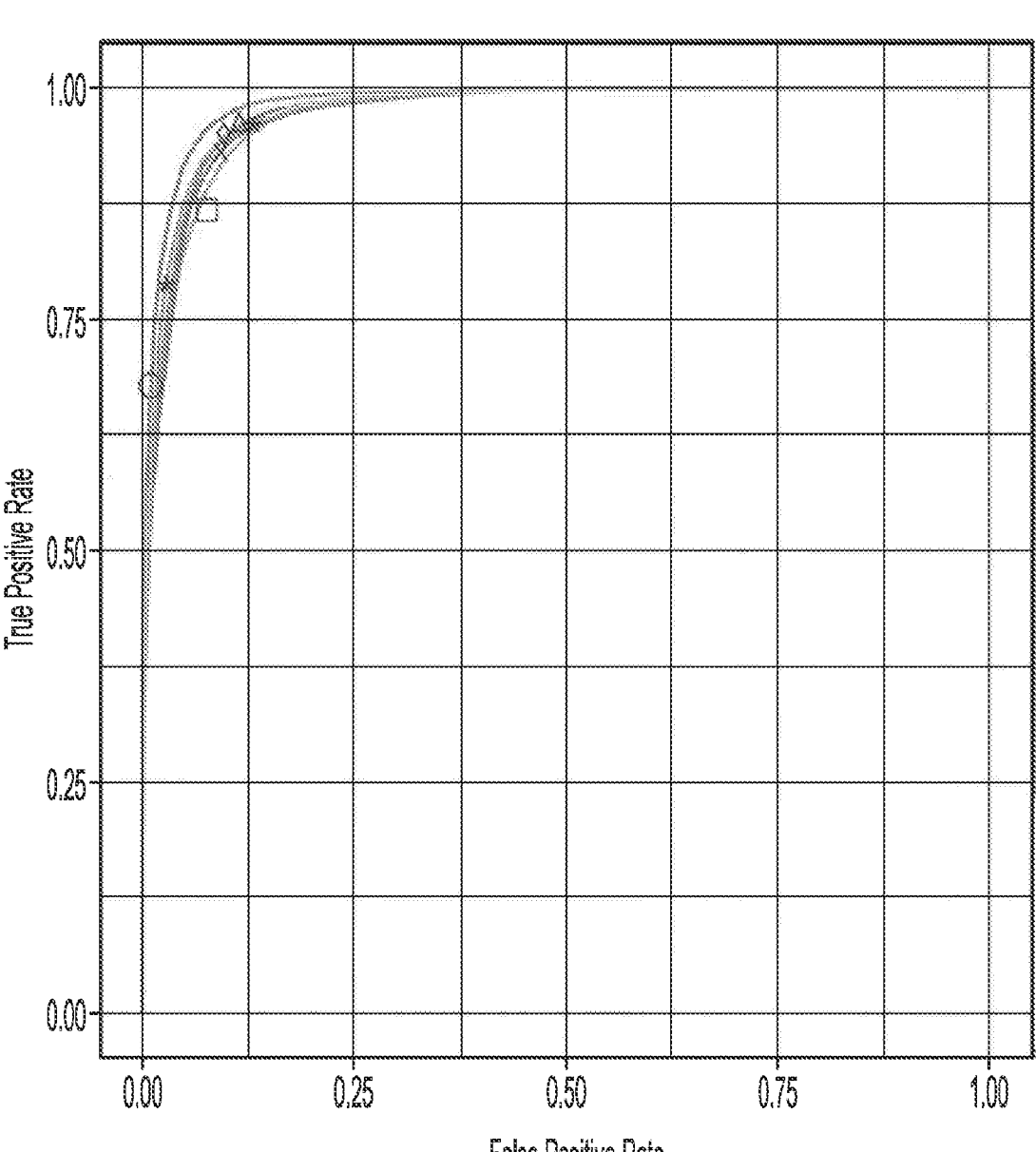
FIG. 14A-B provides graphs showing results of comparison of different consensus modalities and temporal smoothing.
Figure 14B:
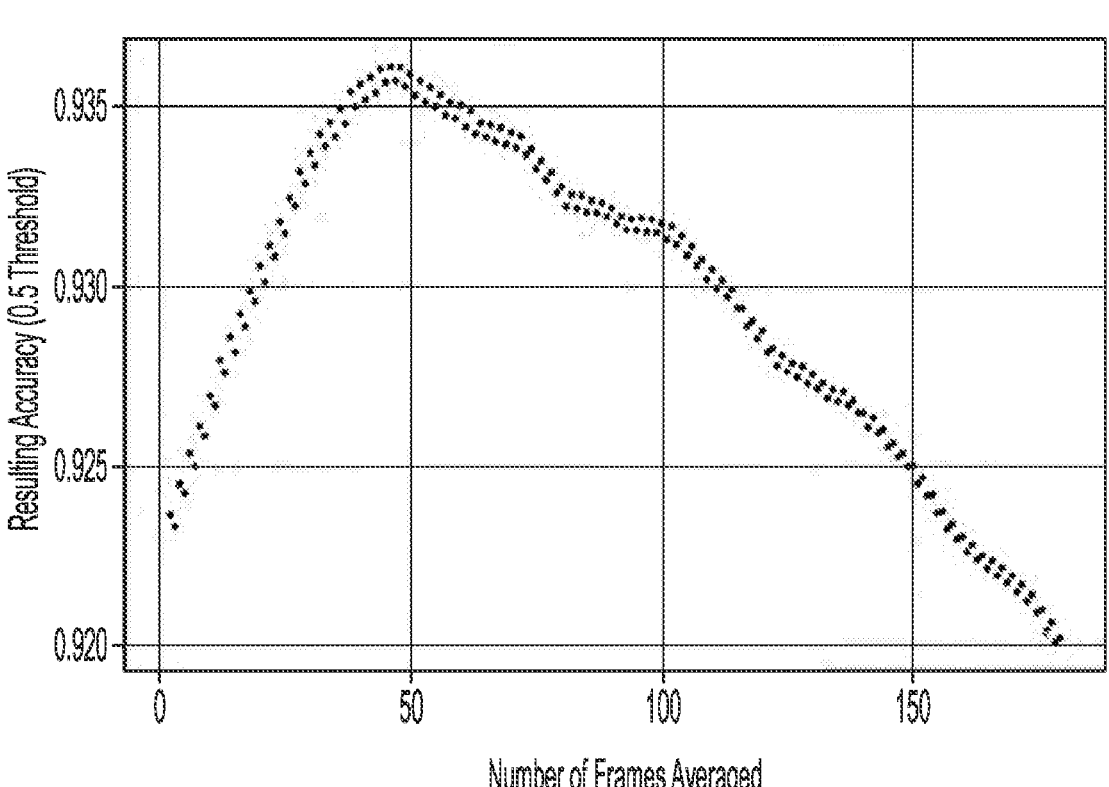

Other approaches for merging the 32 predictions were attempted, including selecting the max value or applying a vote (median prediction). Averaging the prediction probabilities achieved the best performance (FIG. 14A). Finally, a temporal smoothing filter was applied over 46 frames of prediction. Forty six (46) frames was identified as the optimal window for a rolling average (FIG. 14B), which resulted in a final accuracy of 93.7% (ROC AUC of 0.984). Because the network could only make predictions on half a second worth of information, investigations were done on the extremes grooming bout predictions in the large strain survey dataset that was not annotated by humans. Although most of the long bout (>2 minutes) predictions were real, there were some false positives in which the mouse was resting in a grooming-like posture. To mitigate these rare false positives, a heuristic was implemented to adjust predictions. Results of the studies identified that grooming motion typically caused ellipse-fit shape changes (W/L) to have a standard deviation greater than $2.5\times10^{-4}$. When a mouse was resting, the shape changes (W/L) standard deviation does not exceed $2\times10^{-5}$. Knowing that a mouse's posture in resting may be visually similar to a grooming posture, predictions were assigned in time segments where the standard deviation of shape change (W/L) over a 31 frame window was less than $5\times10^{-5}$ to a "not grooming"

prediction. Of all the frames in this difficult to annotation posture, 12% were classified as grooming. This suggests that this was not a failure case for the network, but rather a limitation of the network when only given half a second worth of information to make a prediction.

Figure 11D:
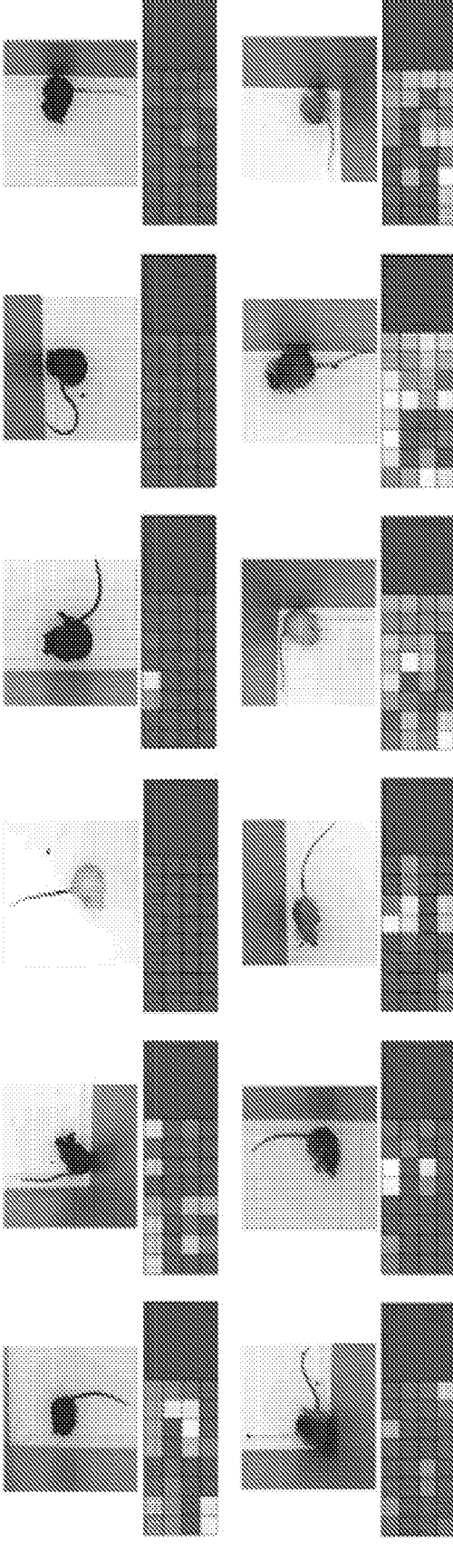
Figure 11E:
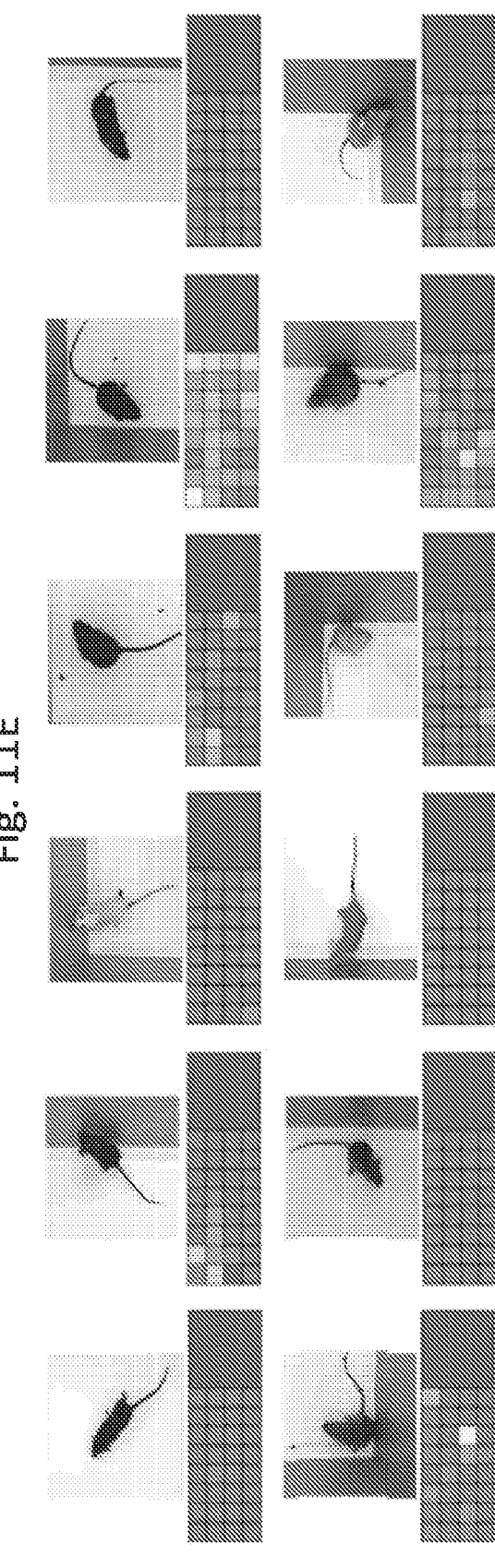

This approach was determined to be capable of handling varying mouse posture as well as physical appearance, e.g. coat color and body weight. Good performance was observed over a wide variety of postures and coat colors (FIG. 11D-E). Even nude mice, which have a drastically different appearance than other mice, achieved good performance. Visually, instances were observed where a small number of frame orientations and models made incorrect predictions. Despite this, the consensus classifier made the correct prediction.

Example 3

Definition of Grooming Behavioral Metrics

Figure 15A:
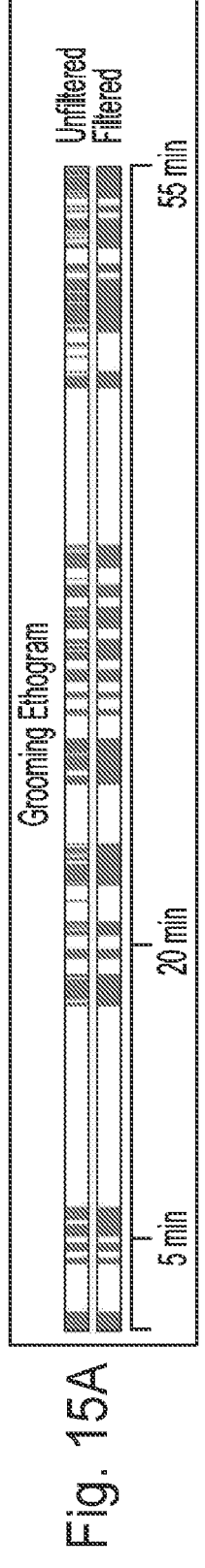
Figure 15B:
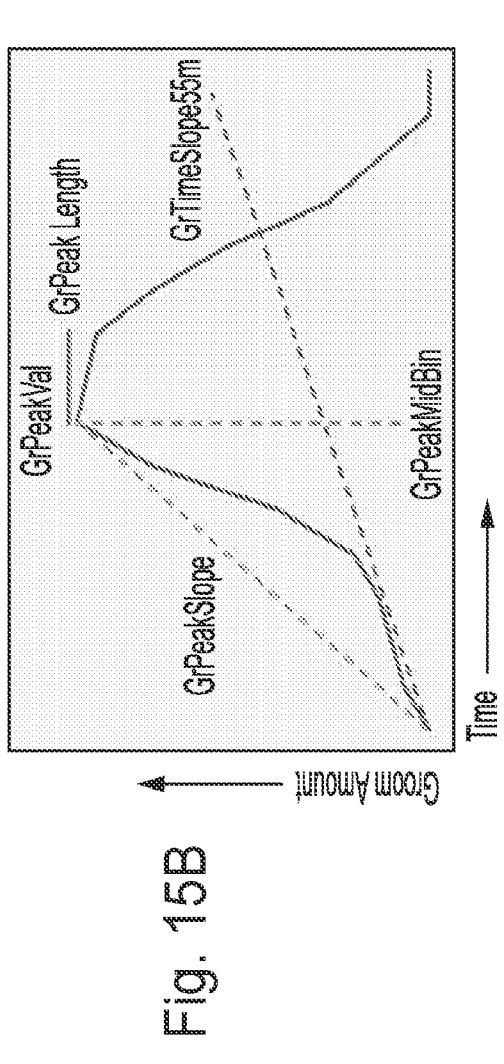

Studies were performed and a variety of grooming behavioral metrics were designed that described both grooming quantity and grooming pattern. A single grooming bout was defined as continuous time spent grooming without interruption that exceeds 3 seconds (see Kalueff et al., Neurobiology of grooming behavior. Cambridge University Press; 2010). Brief pauses (less than 10 s) were allowed, but no locomotor activity was allowed for this merging of time segments spent grooming. Specifically, a pause occurred when motion of the mouse did not exceed twice its average body length. From this, a grooming ethogram was obtained for each mouse (FIG. 15A). Using the ethogram, the total duration of grooming calls in all grooming bouts was summed to calculate the total duration of grooming. When the number of bouts and total duration were known, the average bout duration was calculated by dividing the two. For measurement purposes, the 5-minute, 20-minute, and 55-minute summaries of these measurements were calculated. The 5 and 20 minutes were included because these are typical open field assay durations. Using 1-minute binned data, a variety of grooming pattern metrics were calculated (FIG. 15B). A linear slope was fit to the results to discover temporal patterning of grooming during the 55 minute assay (GrTimeSlope55 min). Positive slopes for total grooming duration inferred that the individual mouse was increasing its time spent grooming the longer it remained in the open field test. Negative slopes for total grooming duration inferred that the mouse spent more time grooming at the start of the open field test than at the end. This is typically due to the mouse choosing to spend more time doing another activity over grooming, such as sleeping. Positive slopes for number of bouts inferred that the mouse was initiating more grooming bouts the longer it remained in the open field test. Using 5-minute binned data, additional metrics were designed to describe grooming pattern by selecting which minute a mouse spent the most time grooming (GrPeakMidBin) and the time duration spent grooming (GrPeakVal) in that minute. A ratio between these values (GrPeakSlope) was also calculated. Finally, when looking at strain-level averages of grooming, it was possible to identify how long a strain remained at its peak grooming (GrPeakLength). A variety of open-field measurements were compared, including both grooming behavior and classical open-field measurements (FIG. 15C). These phenotypes were grouped into four (4) groups. Grooming quantity described how much an animal groomed. Grooming pattern metrics described how an animal changed its grooming behavior over time. Open field anxiety measurements were traditional open-field phenotypes that have been validated to measure anxiety. Open field activity was a traditional open field phenotype that described the general activity of an animal.

Example 4

Sex and Environment Covariate Analysis of Grooming Behavior

With this trained classifier, studies were done to determine whether sex and environment factors affected grooming behavior expression in an open field. Data collected over 29 months for two strains, C57BL/6J and C57BL/6NJ was used to carry out this analysis. These two strains are sub-strains that were identical in 1951 and are two of the most widely used strains in mouse studies [Bryant et al., 2018 In: *Molecular-genetic and statistical techniques for behavioral and neural research* Elsevier; p. 165-190]. C57BL/6J is the mouse reference strain and C57BL/6NJ has been used by the IMPC to generate a large amount of phenotypic data [Brown S, & Moore M, 2012 Towards an Encyclopedia of Mammalian Gene Function: the International Mouse Phenotyping Consortium]. Analysis was done on the 775 C57BL/6J (317F, 267 458M) and 563 C57BL/6NJ (240F, 323M) under a wide variety of experimental conditions over the two and a half years. Across all these novel exposure to open field, their grooming behavior was quantified for the first 30 minutes (FIG. 16A-H, 669 hours total data). The data was analyzed for effect of sex, season, time-of-day, age, room origin of the mice, light levels, tester, and white noise. To achieve this, a stepwise linear model selection was applied to model these covariates. Both forward and backward model selection results matched. After identifying significant covariates, a second round of model selection was applied that included sex interaction terms. The model selection identified sex, strain, room of origin, time of day, season as significant while age, weight, presence of white noise, and tester were not significant under the described testing conditions. Additionally, the interaction between sex and both room of origin and season were identified as significant covariates. Results of studies are shown in Table 1.

TABLE 1

| Results of covariate studies | |
| --- | --- |
| Covariate | p-value |
| Sex | <2.2e−16 (p < or = 0.001) |
| Strain | 0.0267546 (p < or = 0.05) |
| Room Origin | 5.357e−13 (p < or = 0.001) |
| Morning | 0.0001506 (p < or = 0.001) |
| Season | 0.0039826 (p < or = 0.01) |
| Sex by Room Origin | 0.0001568 (p < or = 0.001) |
| Sex by Season | 0.0235954 (p < or = 0.05) |

Figure 16A:
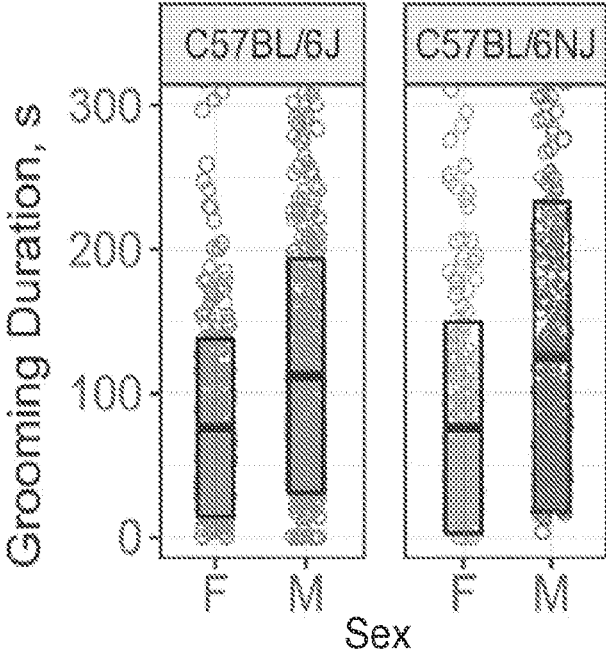
FIG. 16A-H provides images of covariant analysis results of subjects with various characteristics, such as sex, season, etc.
Figure 16B:
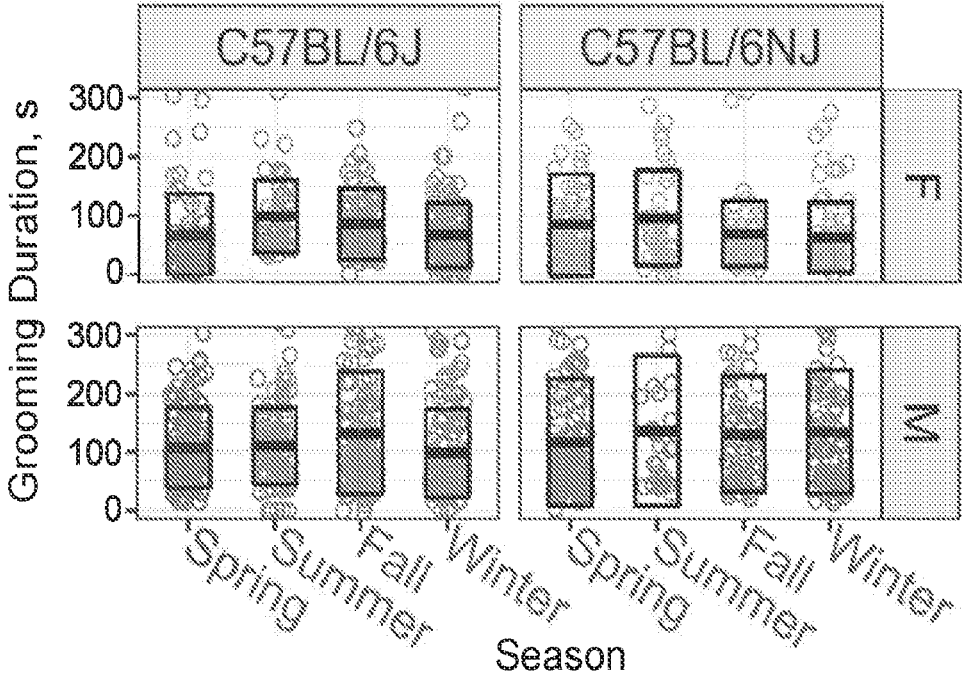
Figure 16C:
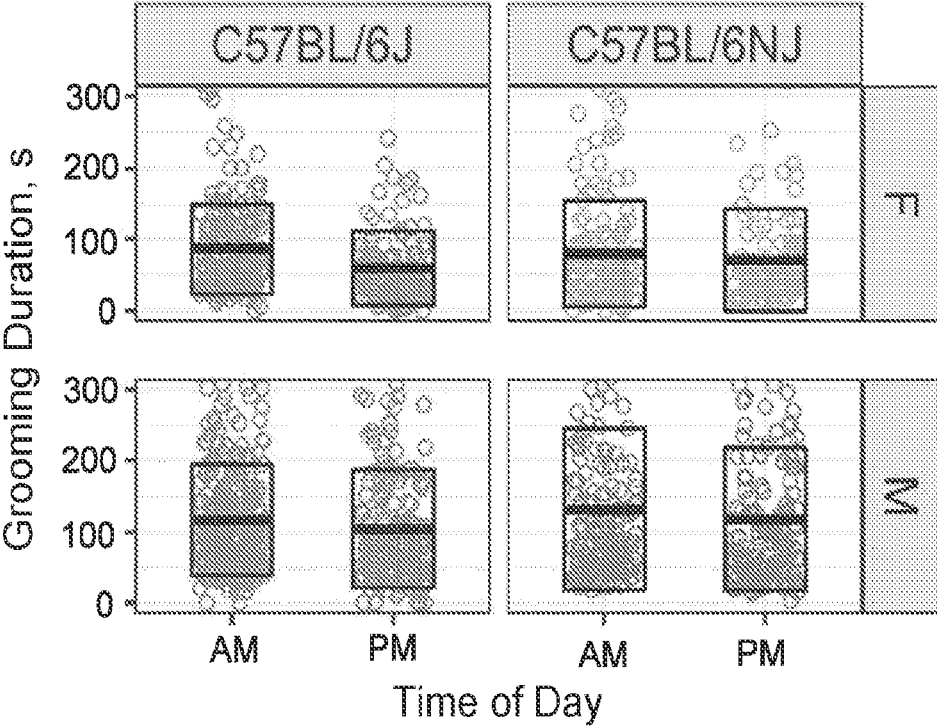
Figure 16D:
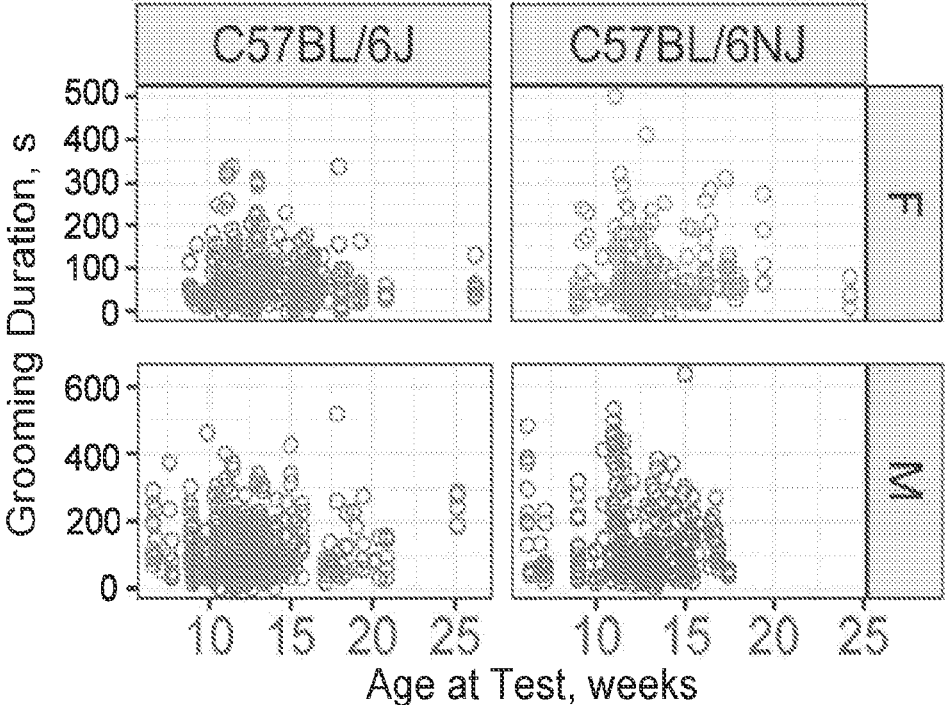

Results demonstrated an effect of Strain (FIG. 16A, p=0:0268 C57BL/6J vs C57BL/6NJ). Although the effect size is small, C57BL/6NJ groom more than C57BL/6J. Additionally, a sex difference was observed (FIG. 16A, $p < 2.2 \times 10^{-16}$ Males vs Females). Males groomed more than females in both strains. Because Sex had a strong effect, interaction terms were included with other covariates in a second pass of the model selection. The model identified season as a significant covariate (FIG. 16B, p=0.004). Surprisingly, the model also identified an interaction between sex and season (p=0.024). Female mice for both strains showed an increase in grooming during the summer and a decrease in the winter. Males did not show this trend, visually confirming the sex-season interaction. Testing was carried out between 8 AM and 4 PM. In order to determine if the time that test of was carried out affected grooming behavior, the data was split into two groups: morning (8 am to noon) and afternoon (noon to 4 pm). A clear effect of time of day was observed (FIG. 16C, p=0.00015). Mice tested in the morning groomed more overall. Mice of different ages were tested, with ages ranging from 6 weeks to 26 weeks old. At the beginning of every test, the mice were weighed and were found to have a range of 16 g to 42 g. No significant effect of age (FIG. 16D, r=−0.065, p=0.119) or body weight (r=0.206, p=0.289) on grooming duration was observed.

Figure 16E:
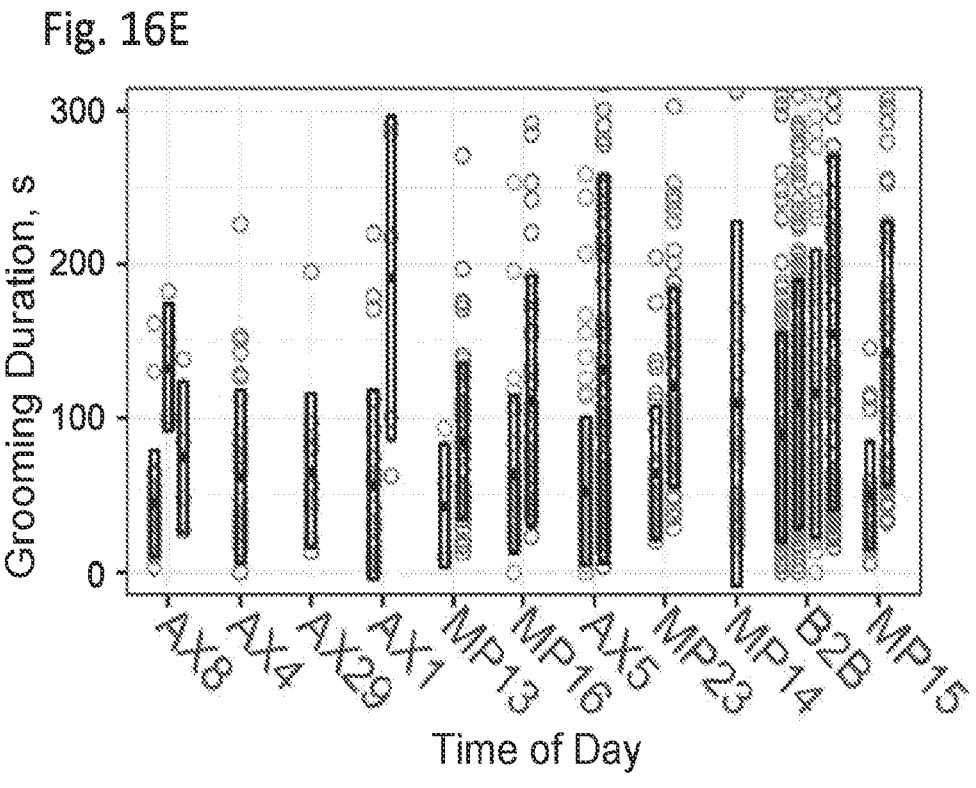
Figure 16F:
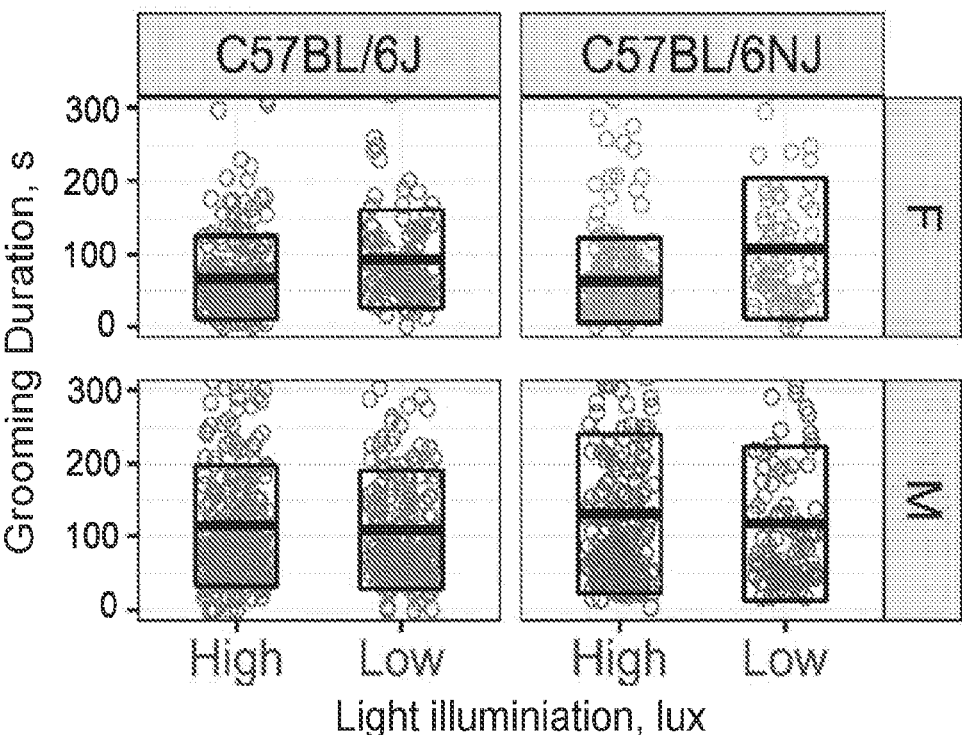
Figure 16G:
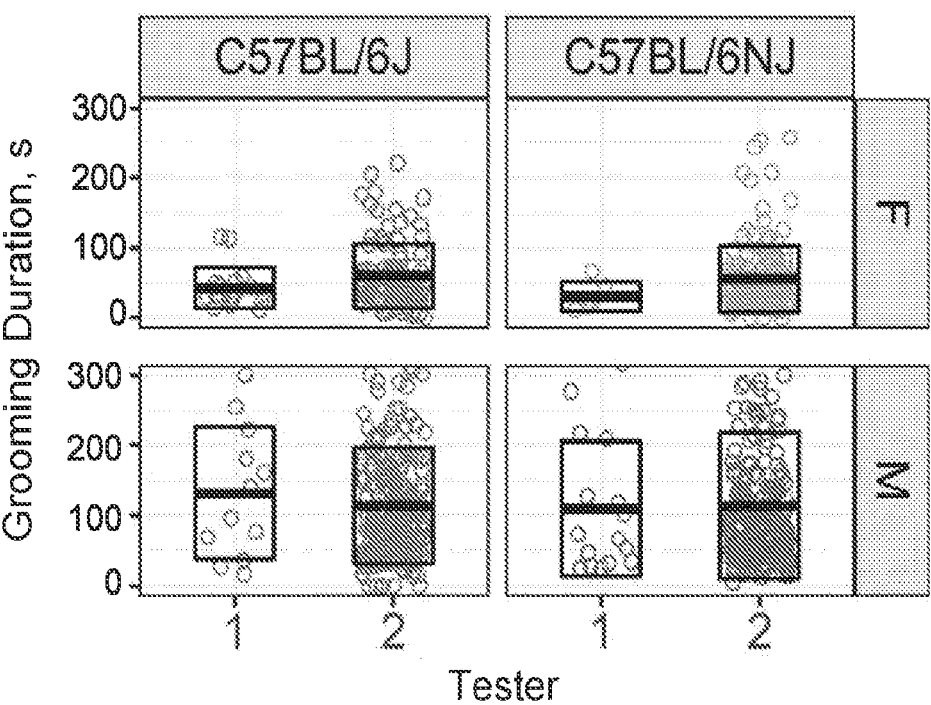
Figure 16H:
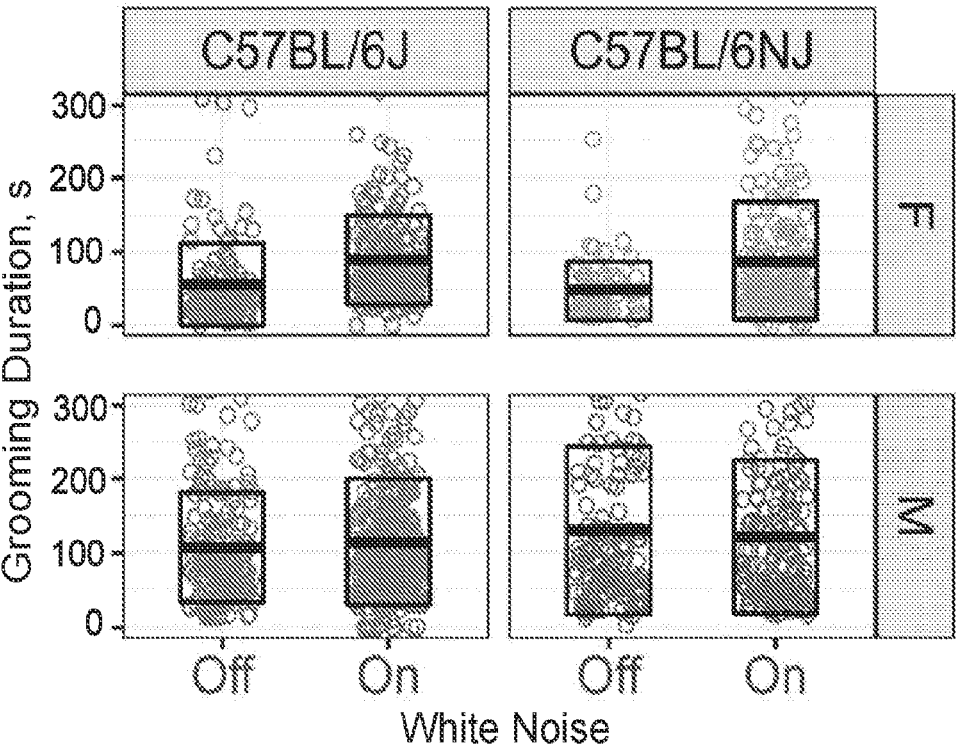

Grooming levels of mice from production that were internally shipped were compared to testing room with mice bred and raised in a room adjacent to the testing room (B2B). Six production rooms supplied exclusively C57BL/6J (AX4, AX29, AX1, MP23, MP14, MP15), 3 rooms supplied exclusively C57BL/6NJ (MP13, MP16, AX5), and one room supplied both strains (AX8). All shipped mice were housed in B2B for at least a week prior to testing. Significant effects were observed based for room of origin (FIG. 16E, p=5.357×10$^{-13}$). For instance, C57BL/6J males from AX4 and AX29 were low groomers compared to other rooms, including B2B. Shipped C57BL/6NJ from all rooms seemed to have low levels of grooming compared with B2B. It was concluded that room of origin and shipping could have large effects on grooming behaviors. Two light levels were also tested, 350-450 lux and 500-600 lux white light (5600K). Results demonstrated there were significant effects of light levels on grooming behavior (FIG. 16F, p=0.04873). Females from both strains groomed more in lower light, however males didn't seem to be affected. Despite this, the model did not include a light-sex interaction, suggesting that other covariates better accounted for the visual interaction with sex here. The open field assays were carried out by two male testers, although the majority of tests were carried out by tester 2. Both testers carefully followed a testing protocol designed to minimize tester variation. No significant effect was observed (FIG. 16G, p=0.65718) between testers. Finally, white noise was frequently added to prior open-field assays in order to create a uniform background noise levels and to mask noise created by experimenter [Gould, T. Mood and Anxiety Related Phenotypes in Mice, 2009 Neuromethods 42. DOI 10.1007/978-1-60761-303-9_1, Humana Press]. Although the effects of white noise have not been extensively studied in mice, existing data indicates that at higher levels of white noise increases ambulation [Weyers P, et al., 1994 Behavioural Processes 31(2-3):257-267]. Studies were performed in which effects of white noise (70 db) on grooming behavior of C57BL/6J and C57BL/6NJ mice were tested using methods of the invention and no significant difference was identified in duration spent grooming (FIG. 16H). Although there appeared to be a stratification present for both C57BL/6J 316 and C57BL/6NJ females, other cofactors better accounted for this result. Combined, these results indicated environmental factors such as season, time of day, and room origin of the mice affected grooming behavior and may serve as environmental confounds in any grooming study. Age, body weight, light level, tester, and white noise were also investigated and it was determined that these cofactors did not influence grooming behavior under these experimental conditions.

Example 5

Strain Differences for Grooming Behavior

Next, the grooming classifier was used to carry out a survey of grooming behavior in the inbred mouse. Animals tested included 43 standard and 8 wild-derived strains and 11 diallel F1 hybrid mice from the Jackson Laboratory mouse production. These were tested over a 31-month period and in most cases consisted of a single mouse shipment from Jackson Laboratory production. Other than C57BL/6J and C57BL6/NJ, on average 8 males and 8 females from each strain were tested, and the animals were on average 11 weeks in age. Each mouse was tested for 55 minutes in the open field as previously described [Geuther B. Q., et al., 2019 Communications Biology. 2(1):124]. This data set consisted of 2457 animals, 2252 hours of video. Video data were classified for grooming behavior as well as open-field activity and anxiety metrics. Behavior metrics were extracted as described in FIG. 15. In order to visualize the variance in phenotypes, each animal was plotted across all strains with corresponding strain mean and 1 standard deviation range and ethograms of select strains (FIG. 17A-F). Studies included distinguishing between classical laboratory strains and wild-derived inbred strains.

Grooming Amount and Pattern in Genetically Diverse Mice

Figure 19A:
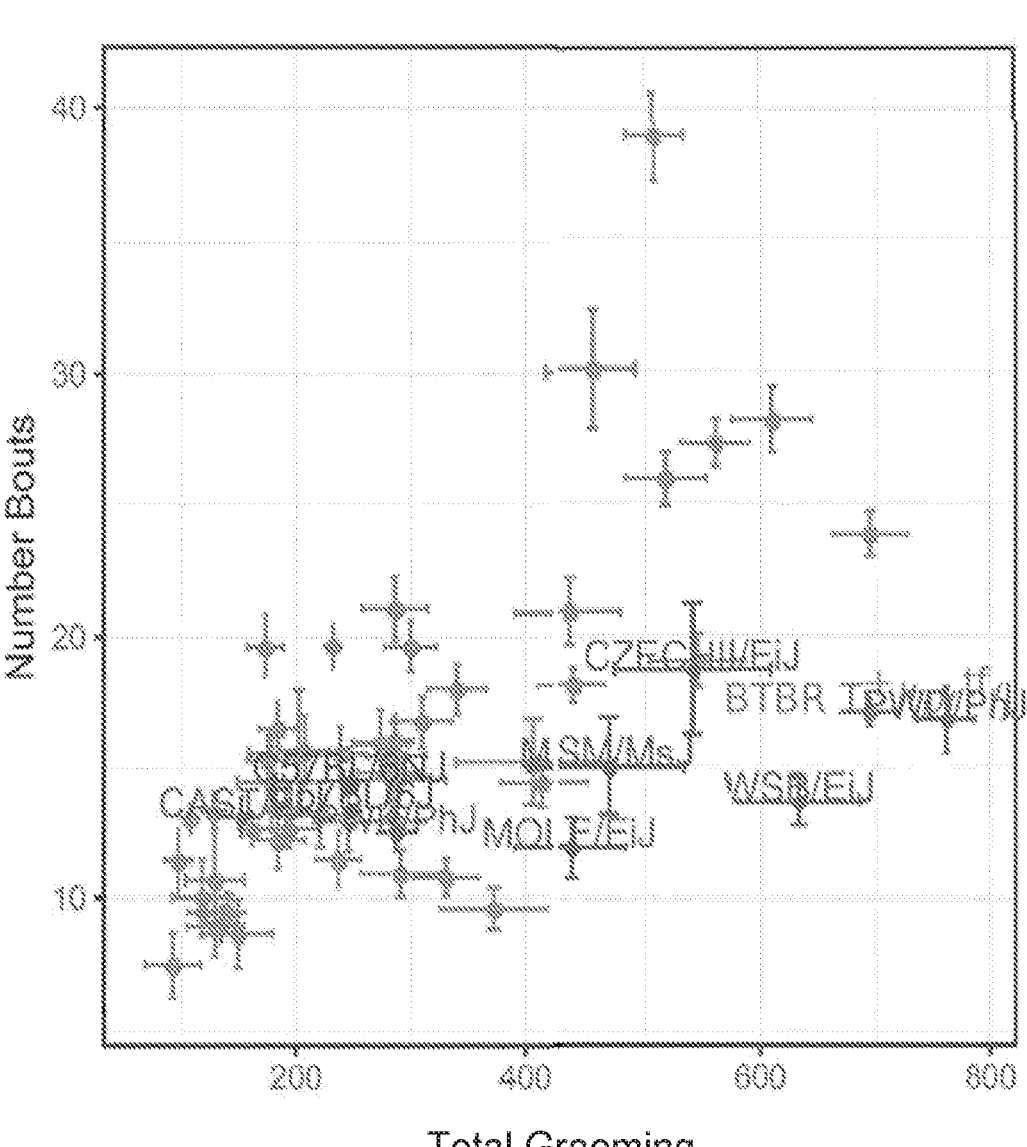
Figure 19B:
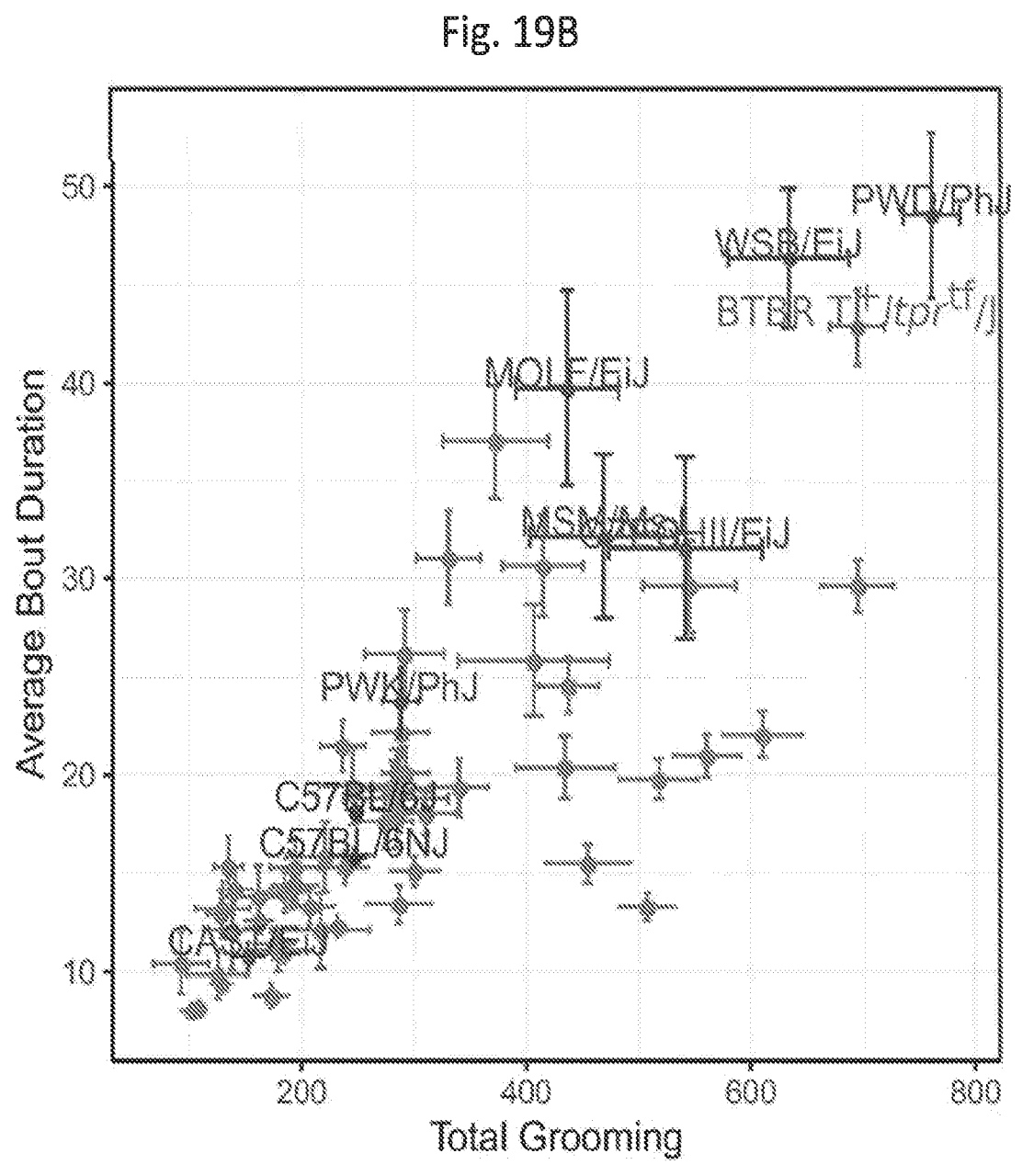
Figure 19C:
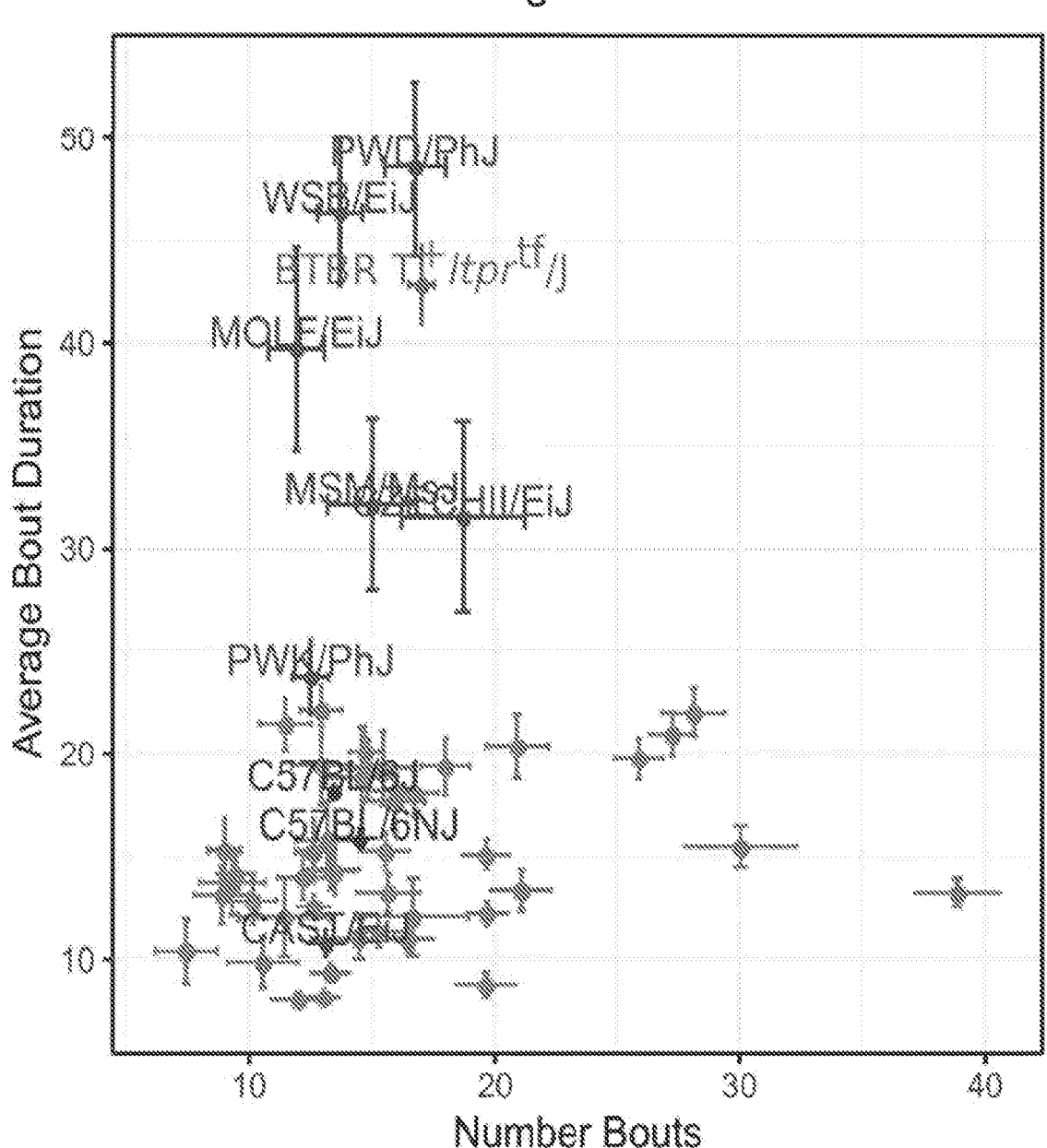
Figure 20:
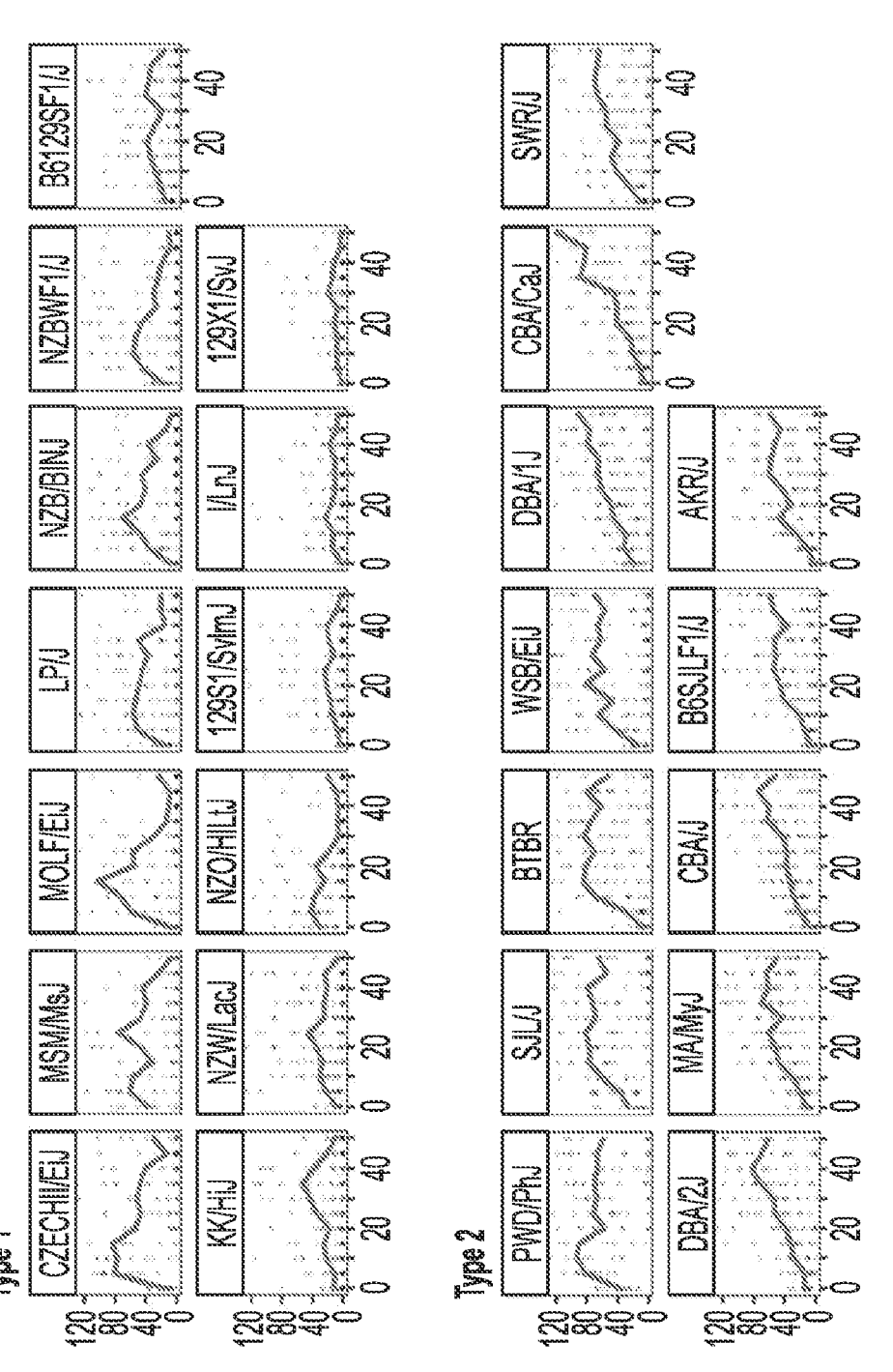
FIG. 20 provides graph panels illustrating clustering for strain survey of grooming pattern over time. Three types of grooming patterns of mice in the open field revealed by k-means clustering of grooming pattern over time. Grooming duration in 5-minute bins is shown over the course of the open field experiment (solid line) and data from individual mice (grey points).
Figure 20:
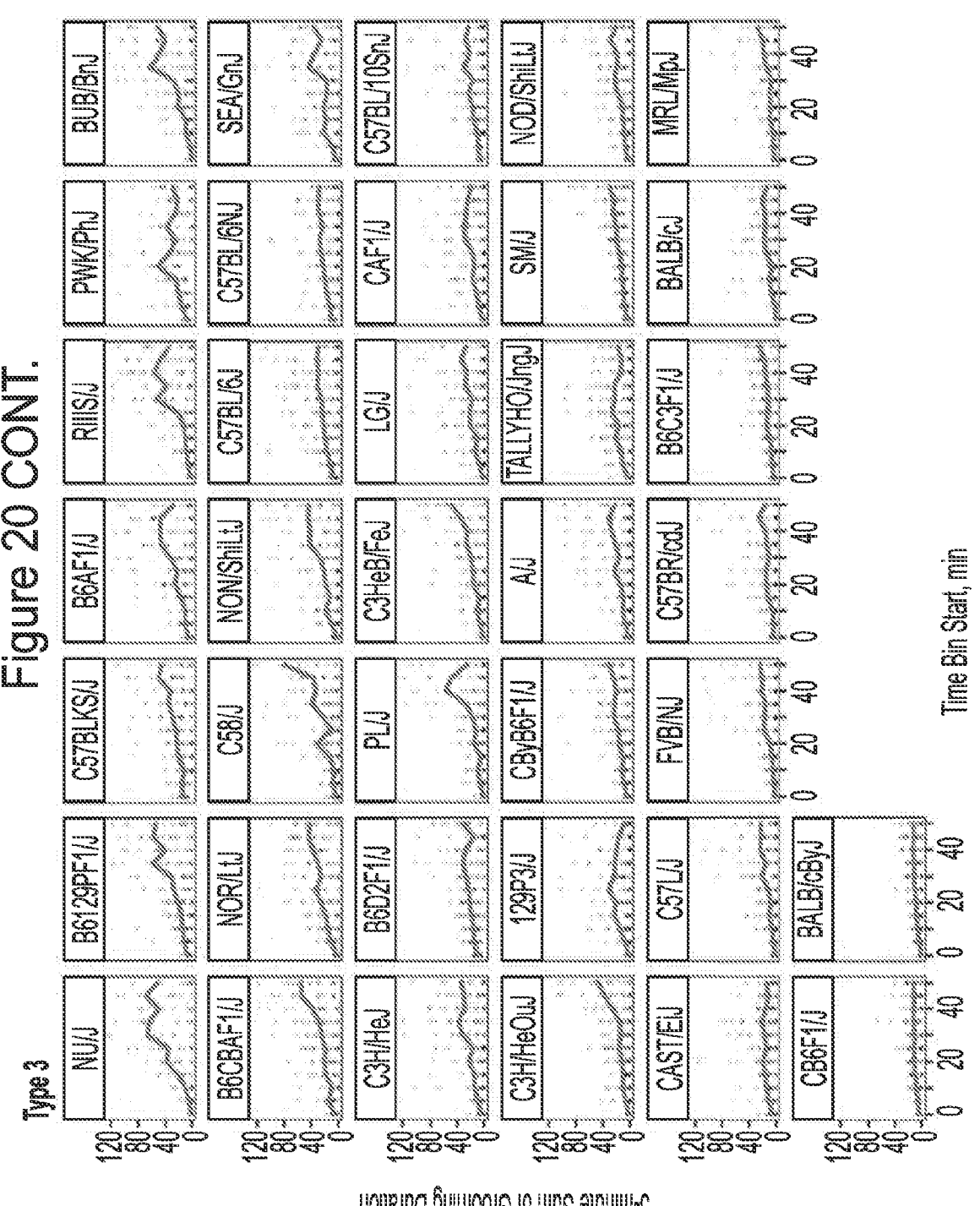
Figure 21:
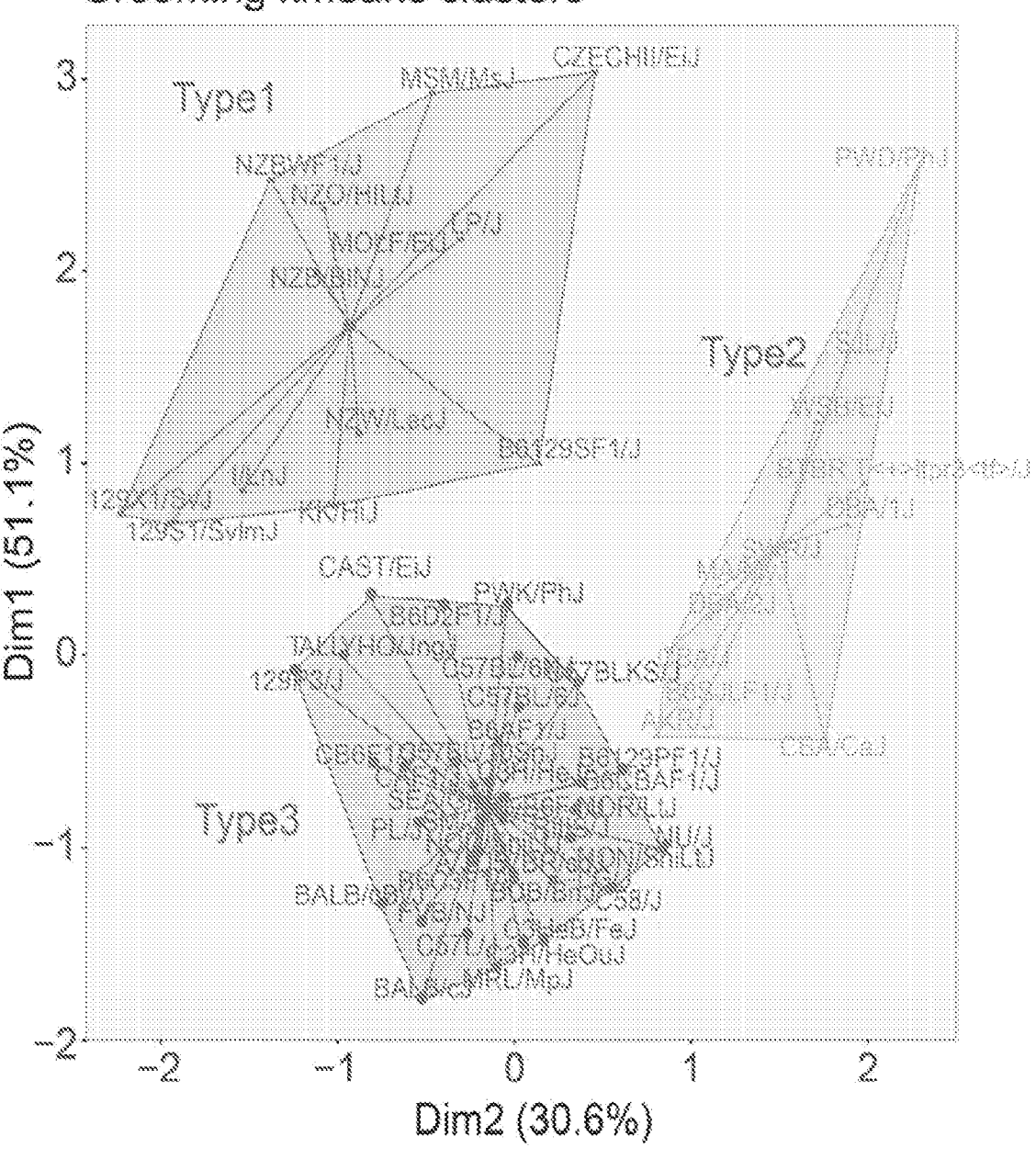
FIG. 21 Results from the k-means clustering. The first two principal components from this clustering accounts for 81.7% of variance. 3 clusters were identified. This allows us to assign each strain to one of three classes of grooming behaviors.

Large continuous variance in total grooming time, average length of grooming bouts, and the number of grooming bouts were observed in the 55-minute open field assay (FIG. 17A-F). Total grooming time varied from 2-3 minutes in strains such as 129X1/SvJ and BALB/cByJ to 12 minutes in strains such as SJL/J and PWD/PhJ, approximately a 6-fold difference in grooming time. Strains such as 129X1/SvJ and C57BR/cdJ had less than 10 bouts, whereas MA/MyJ had almost 40 bouts. The bout duration also varied from 5 seconds to approximately 50 seconds in BALB/cByJ and PWD/PhJ, respectively. In order to visualize relationships between phenotypes strain mean and 1SD range correlation plots (FIG. 19A-C) were created. There was a positive correlation between the total grooming time and the number of bouts as well as the total grooming time and average bout duration. Overall, strains with high total grooming time had increased number of bouts as well as longer duration of bouts. However, there did not seem to be a relationship between number of bouts and the average bout duration, implying that the bout lengths stay constant regardless of how many may occur (FIG. 19A-C). In general, C57BL/6J and C57BL6/NJ fell roughly in the middle for classical inbred strains. Studies included investigation of the pattern of grooming over time by constructing a rate of change in 5 minute bins for each strain (FIG. 20). k-means clustering was used to define three clusters of grooming patterns based on rate of increase in grooming over time, total grooming level, time of peak grooming, and the length of time peak grooming (FIG. 21).

Type 1 consisted of 13 strains with an inverted U grooming pattern. These strains escalated grooming quickly once in the open field, reached a peak, and then started to decrease the amount of grooming, usually leading to a negative overall grooming slope. Often, it was found that animals from these strains were sleeping by the end of the 55-minute open field assay. These strains included high groomers such as CZECHII/EiJ, MOLF/EiJ, and low groomers such as 129X1/SvJ and I/LnJ.

Type 2 consisted of 12 strains that were high-grooming strains that did not reduce grooming by end of the assay. They reached peak grooming early and stayed at this level for the duration of this assay (e.g. PWD/PhJ, SJL/J and BTBR). Others in this group reached peak grooming late and plateaued (e.g. DBA/2J, CBA/J). The defining feature of this group was that high level of grooming was maintained throughout the assay.

Type 3 consisted of most of the strains (30) and showed steady increase in grooming till the end of the assay. Overall, these were medium-to-low grooming strains in this group with a constant low positive or flat slope. It was concluded that under these experimental conditions there were at least three broad, albeit continuous, classes of observable grooming patterns in the mouse.

Example 6

Wild Derived Vs. Classical Strain Grooming Patterns

Figure 17A:
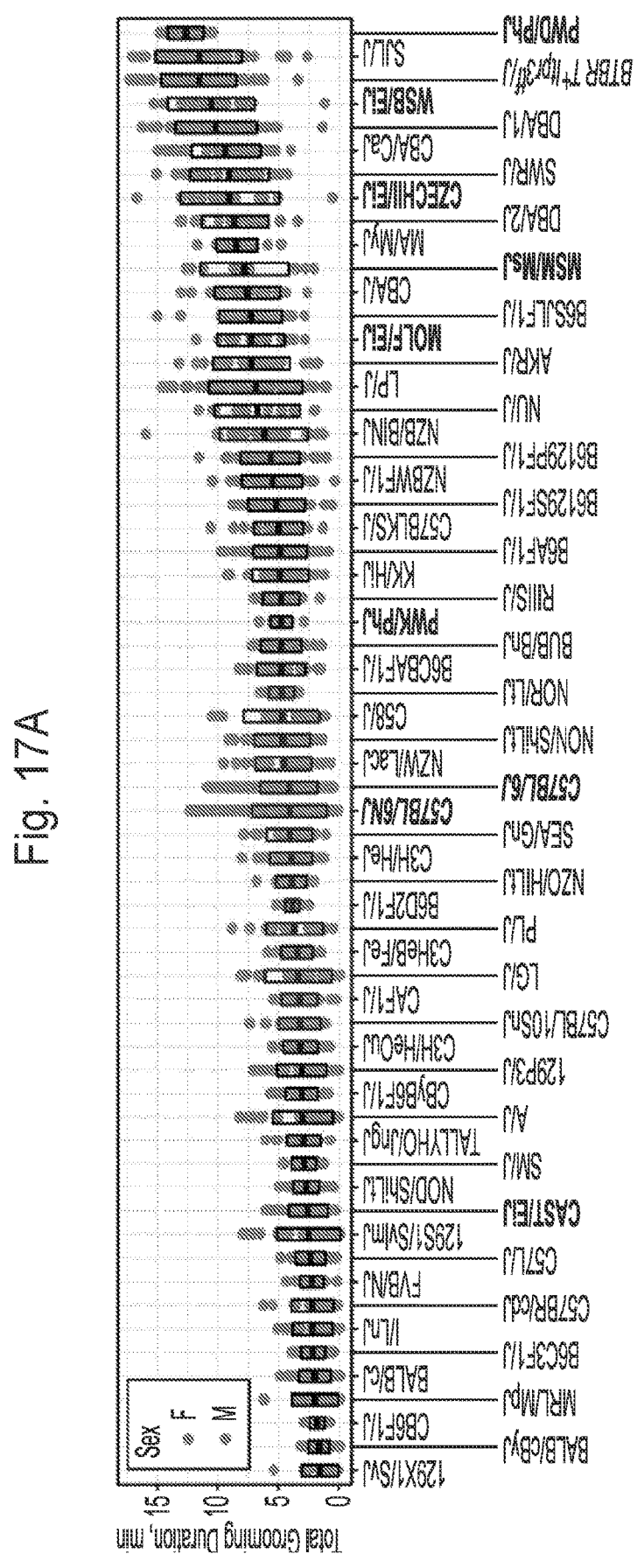

Grooming patterns of classical and wild-derived laboratory strains were compared. Classical laboratory strains are derived from limited genetic stock originating from Japanese and European mouse fanciers [Keeler C E. Laboratory Mouse: Its Origin, Heredity, and Culture; Cambridge, Harvard University Press 1931; Morse H C. Origins of Inbred Mice: Proceedings of a Workshop, Bethesda, Maryland, February 14-16. Acad. Press; 1978; and Silver, L. M. Mouse Genetics: Concepts and Applications. Oxford University Press; 1995]. Classical laboratory inbred mouse lines represent the genome of *Mus musculus domesticus* (*M.m domesticus*) 95% and have only *Mus musculus* 5% [Yang et al., 2011 Nature Genetics. 2011; 43(7):648]. New wild-derived inbred strains were established specifically to overcome the limited genetic diversity of the classical inbred lines [Guénet J L, & Bonhomme F. 2003 Trends in Genetics 19(1):24-31 and Koide T, et al., Experimental Animals. 2011; 60(4):347-354]. Surprisingly, results of the studies demonstrated that most wild-derived strains groomed at significantly higher levels and had longer average bout length than the classical inbred strains. Five of the highest 16 grooming strains were wild-derived (PWD/PhJ, WSB/EiJ, CZECHII/EiJ, MSM/MsJ, MOLF/EiJ) (FIG. 17A). The wild-derived strains also had significantly longer bouts of grooming, with 6 of 16 longest average-grooming-bout strains from this group. Both the total grooming time and average bout length were significantly different between classical and wild-derived strains (FIG. 18A-B). These high-grooming strains represented *M.m. domesticus* and *M.m. musculus* subspecies, which were the precursors to laboratory classical laboratory strains [Yang et al., 2011 Nature Genetics. 2011; 43(7):648]. These wild-derived strains also represented much more of the natural genetic diversity of the mouse populations than the larger number of classical strains tested. This led to a conclusion that the high levels of grooming seen in the wild-derived strains were the normal levels of grooming behavior in mice. This implied that classical laboratory stains may have been selected for low grooming behavior, at least as observed in these experimental conditions.

BTBR Grooming Pattern

Experiments were also performed to closely examine the grooming patterns of the BTBR strain which has been proposed as a model with certain features of autism spectrum disorder (ASD). ASD is a complex neurodevelopmental disorder leading to communication deficits, repetitive behaviors, and social interactions [Association A P, et al. Diagnostic and statistical manual of mental disorders) (DSM-5®. American Psychiatric Pub; 2013]. Compared to C57BL/6J mice, BTBR have been shown to have high levels of repetitive behavior, low sociability, unusual vocalization, and behavioral inflexibility [McFarlane H. G., et al., 2008

Genes, Brain and Behavior 7(2):152-163; Silverman J. L., et al., 2010 Neuropsychopharmacology 35(4):976-989; Moy S. S., et al., 2007 Behavioural Brain Research 176(1):4-20; and Scattoni M. L., et al., 2008 PloS one 3(8)]. Repetitive behavior is often assessed by self-grooming behavior and it has been previously determined that drugs with efficacy in alleviating symptoms of repetitive behavior in ASD also reduce grooming in BTBR without affecting overall activity levels, which provides some level construct validity [Silverman J. L., et al., 2010 Science Translational Medicine 4(131):131ra51 and Amodeo, D. A., et al., 2017 Genes, Brain and Behavior 16(3):342-351].

Figure 17B:
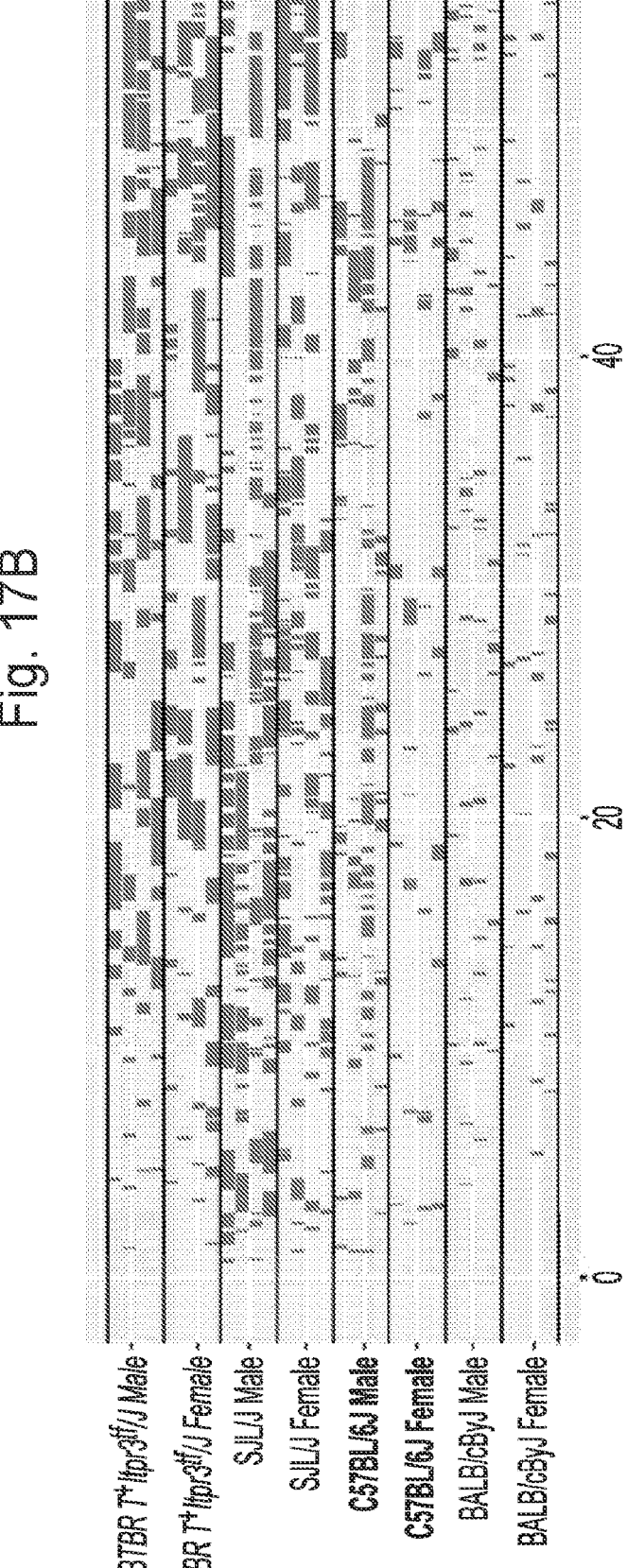
Figure 17C:
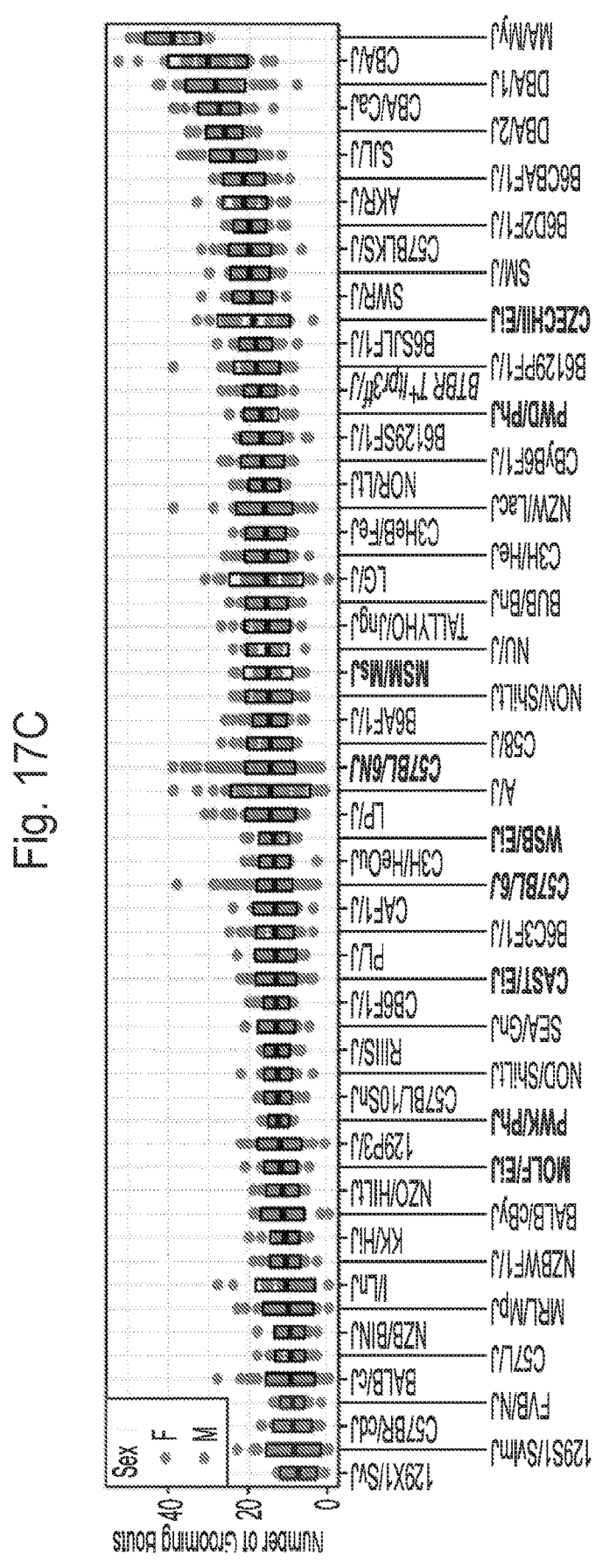
Figure 17D:
Figure 17E:
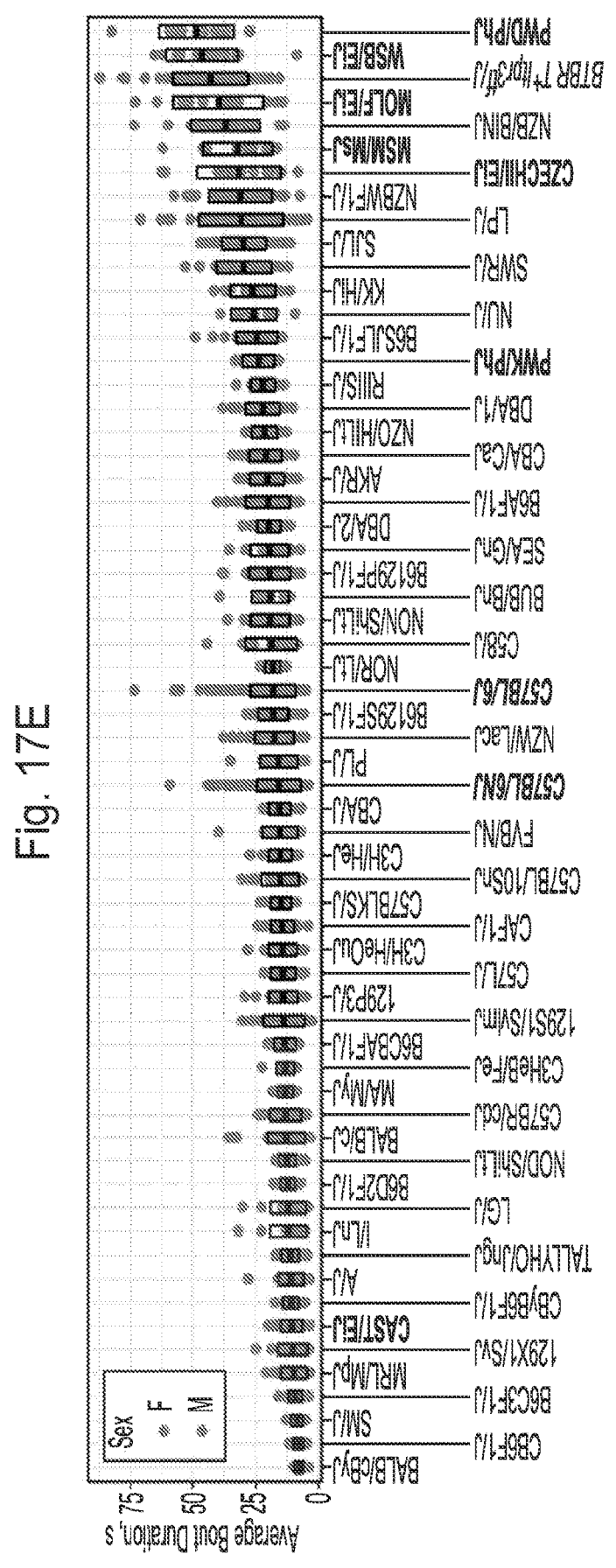
Figure 17F:
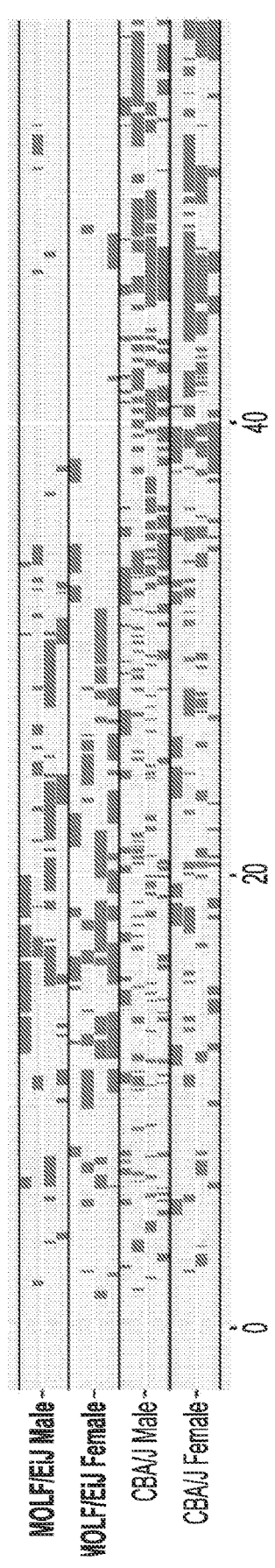
Figure 18B:
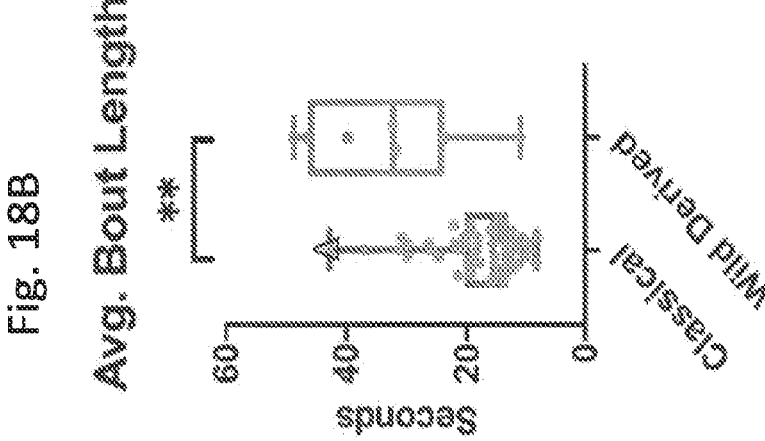
FIG. 18B shows results indicating that wild-derived lines have significantly longer grooming bouts (** $p < 0.01$, Mann-Whitney Test). In both graphs, BTBR strain is indicated with a triangle.
Figure 18A:
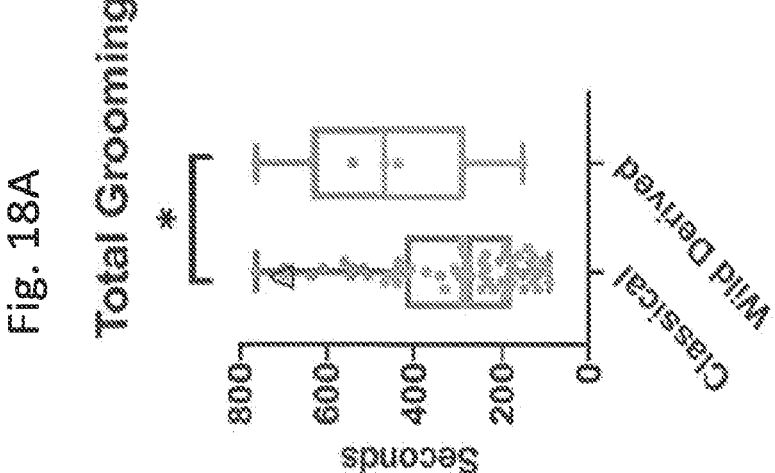
FIG. 18A shows results indicating total grooming time of wild-derived and classical strains are significantly different (* $p < 0.05$, Mann-Whitney Test).

Results of studies described herein identified that total grooming time in BTBR was high compared with C57BL/6J but was not exceptionally high compared to all strains (FIG. 17A-F). C57BL/6J groomed approximately 5 minutes over a 55 minute open-field session, whereas BTBR groom approximately 12 minutes (FIG. 17A). Several classical inbred strains had similar levels of high grooming such as SJL/J, DBA/1J, and CBA/CaJ. The grooming pattern of BTBR belonged to Type 2, which contains five other strains (FIG. 20). One distinguishing factor of BTBR is that they had longer average bouts of grooming from an early point in the open field (FIG. 18A-B). However, again they were not exceptionally high in average bout length measure (FIG. 18A-B). Strains such as SJL/J,PWD/PhJ, MOLF/EiJ, NZB/BINJ had similar long bouts from an early point. It was concluded that BTBR displayed high levels of grooming with long grooming bouts, however this behavior was similar to several wild-derived and classical laboratory inbred strains and was not exceptional. Because social interaction and other features of ASD were not measured, the results did not argue against BTBR as an ASD model.

Example 7

Grooming Mouse GWAS

Figure 22A:
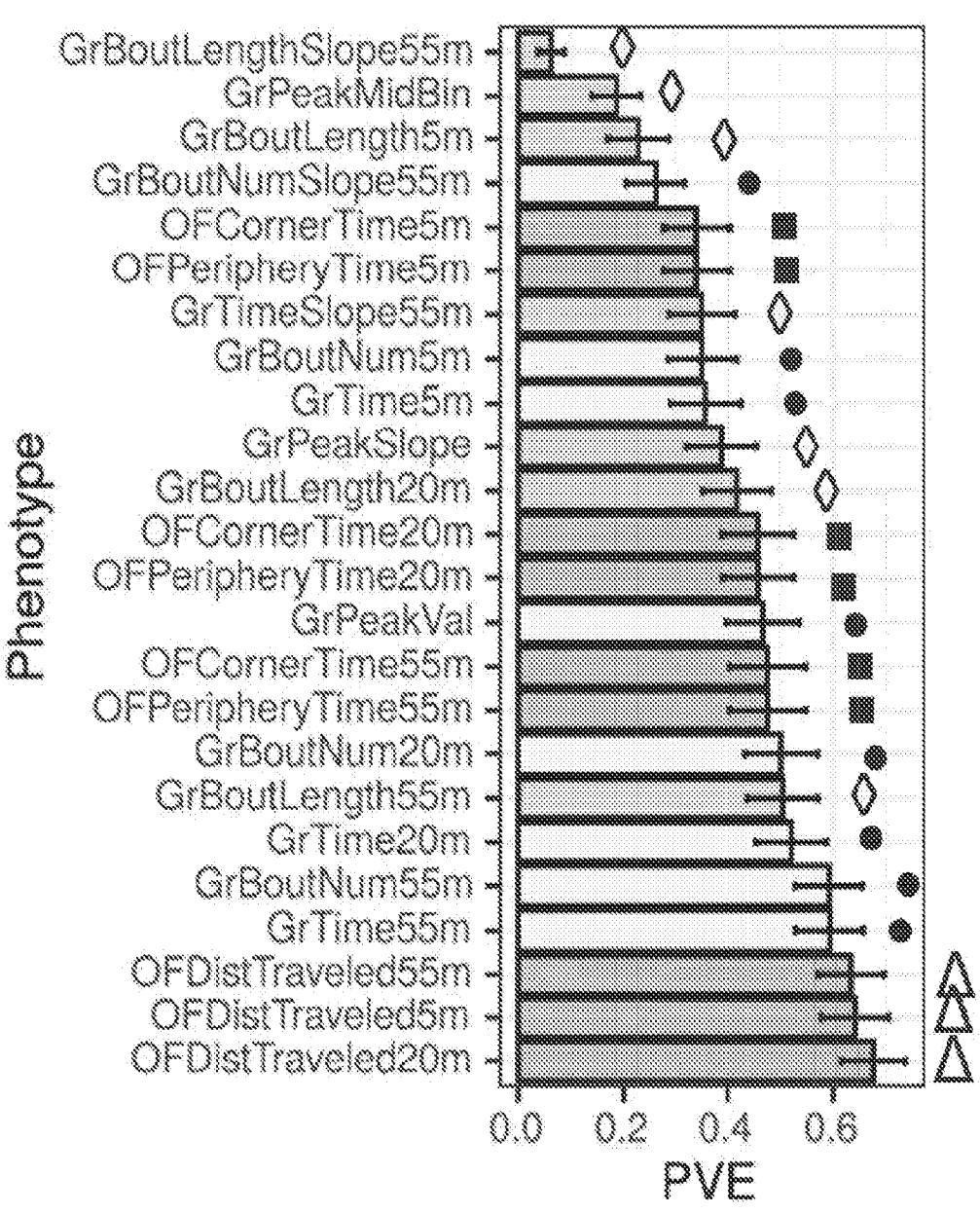
FIG. 22A-D provides graphs, plots, and a heatmap illustrating genotype/phenotype correlation in grooming and open field data.

Studies were done to investigate the underlying genetic architecture of complex mouse grooming behavior and open-field behaviors, and to relate these to human traits. Data from the 51 classical inbred strains and 11 diallel F1 hybrid strains was used to carry out genome-wide association study (GWAS). The eight wild-derived strains were not included because they were highly divergent and could skew mouse GWAS analysis. The 24 phenotypes were categorized into four categories—(1) open-field activity, (2) anxiety, (3) grooming pattern, and (4) quantity (FIG. 15A-C). Linear mixed model (LMM) implemented in Genome-wide EZcient Mixed Model Association (GEMMA) was used for this analysis [Zhou X. & Stephens M. 2012 Nature Genetics 44(7):821-824]. First, heritability of each phenotype was calculated by determining the proportion of variance in phenotypes explained by the typed genotypes (PVE) (FIG. 22A). Heritability ranged from 6% to 68%, with 22/24 traits depicting heritability estimates greater than 20%, a reasonable estimate for behavioral traits in mice and humans [Valdar W, et al., 2006 Genetics 174(2):959-984 and Bouchard Jr T J. 2004 Current Directions in Psychological Science 13(4):148-151], making them amenable for GWAS analysis (FIG. 22A).

Figure 22B:
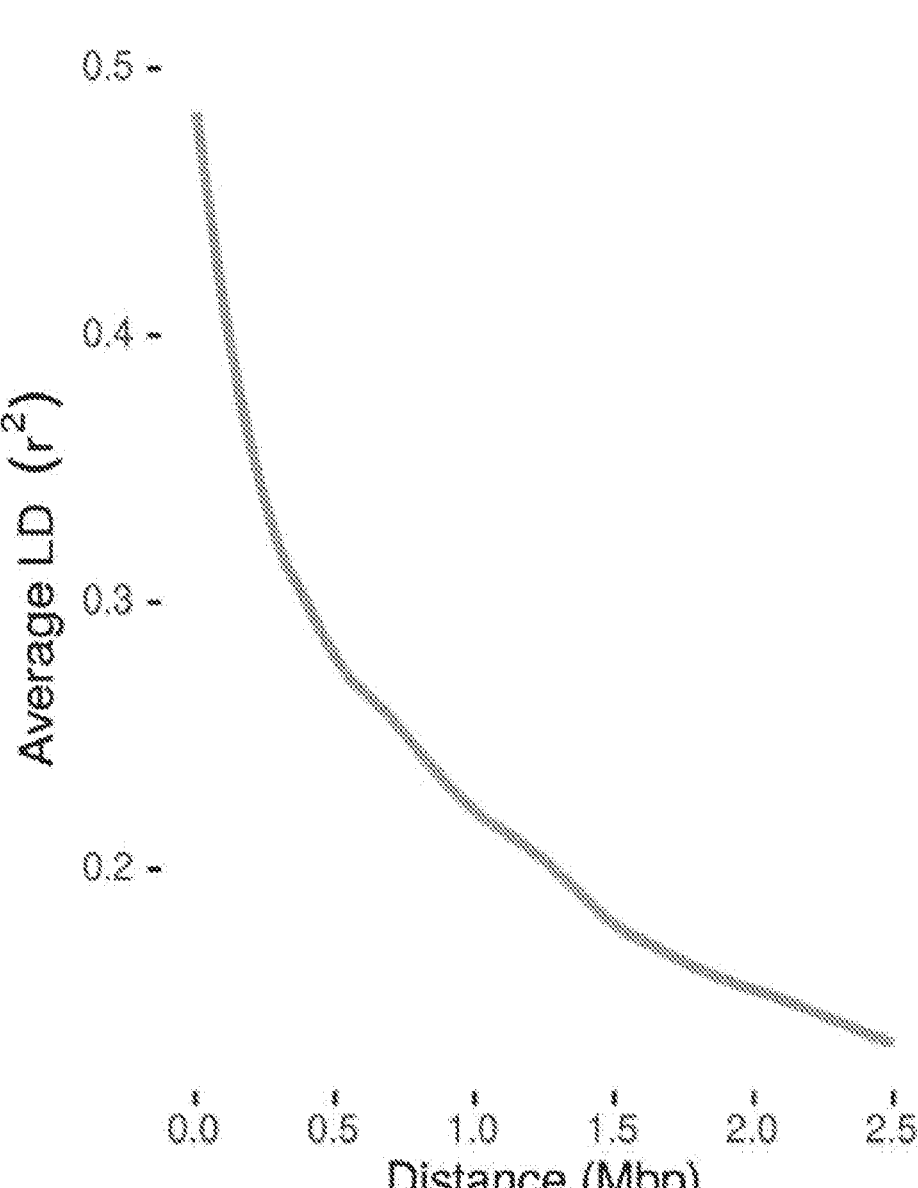

Each phenotype was analyzed using GEMMA, considering the resulting Wald test p-value. In order to correct for the multiple (222,966) SNPs that were tested, and to account for the correlations between SNPs genotypes, an empirical threshold for the p-values was obtained by shuffling the values of one normally distributed phenotype (OFDistTraveled20m) and the minimal p-value of each permutation was taken. This process resulted with a p-value threshold of $1.4 \times 10^{-5}$ that reflected a corrected p-value of 0.05 [Belmonte M. & Yurgelun-Todd D. 2001 IEEE Transactions on Medical Imaging 20(3):243-248]. In order to avoid calling multiple correlating adjacent SNPs, correlated SNPs were clustered under the same peak. A correlation coefficient of $r^2 >= 0.2$ was selected which resulted with large peak regions but seemed like a reasonable compromise between capturing LD blocks and avoiding overly inflated ones (FIG. 22B).

Figure 9A:
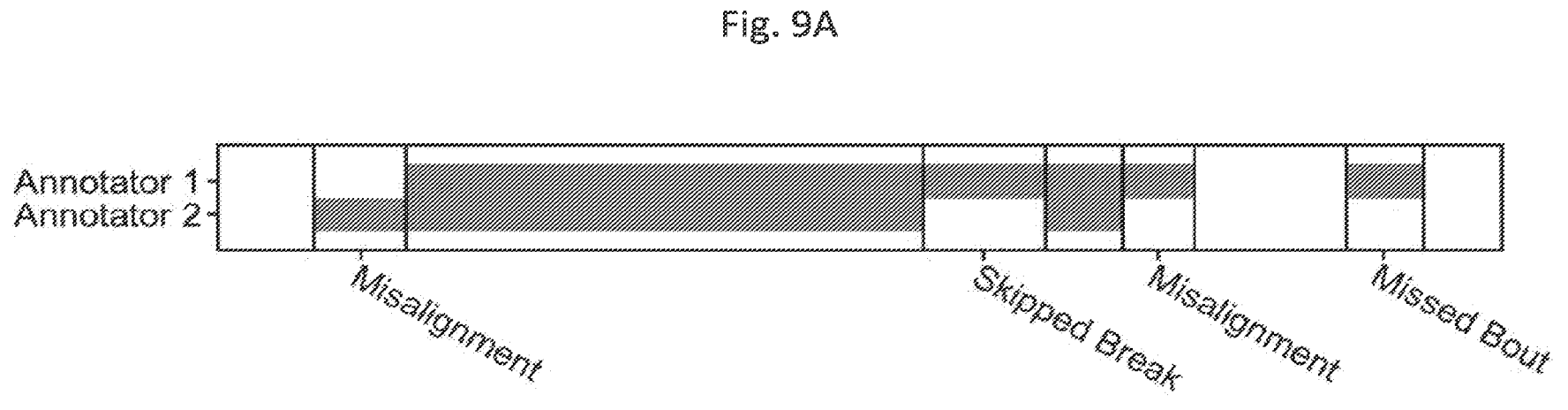
Figures 9B, 9C:
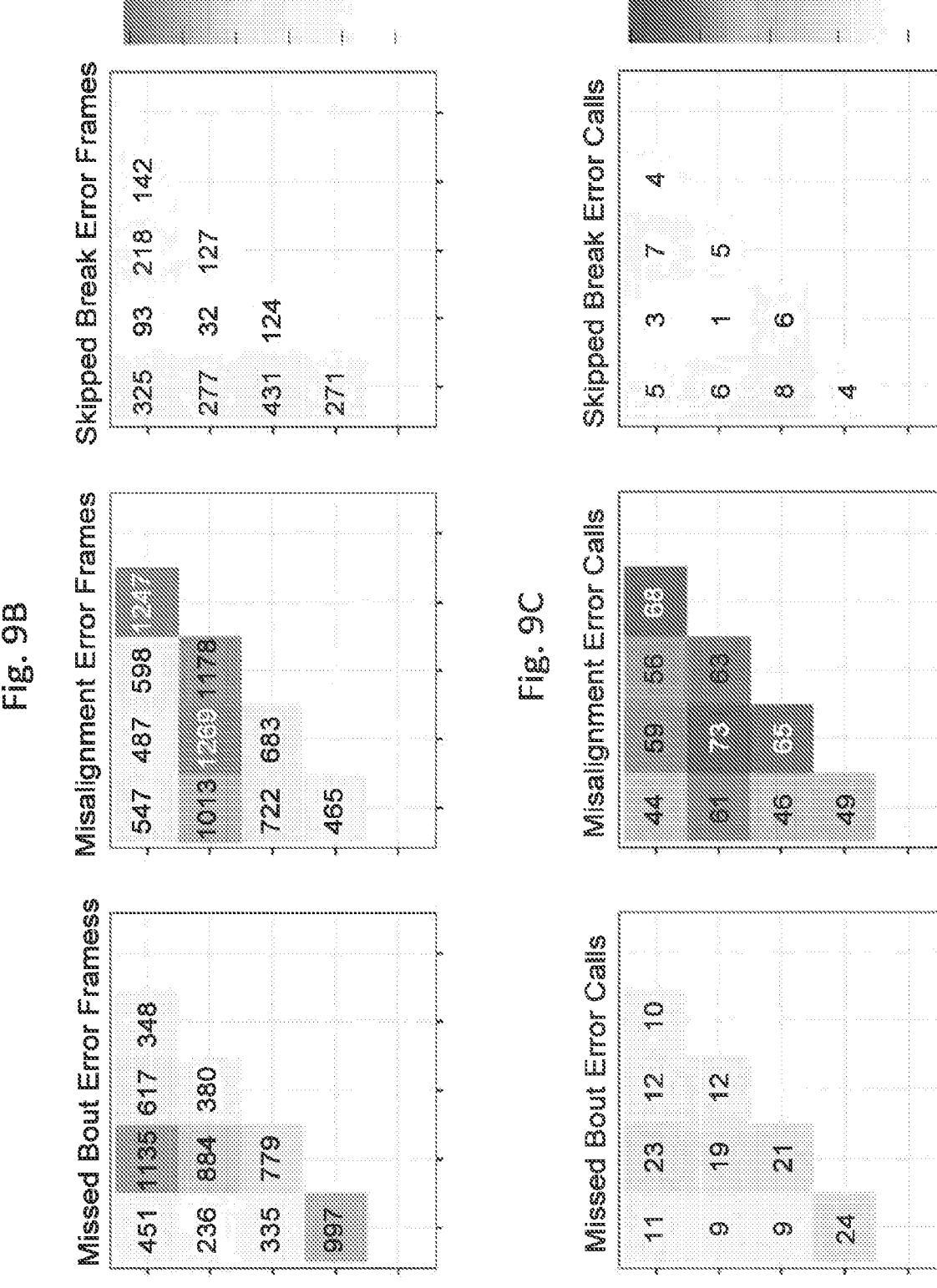
Figure 23:
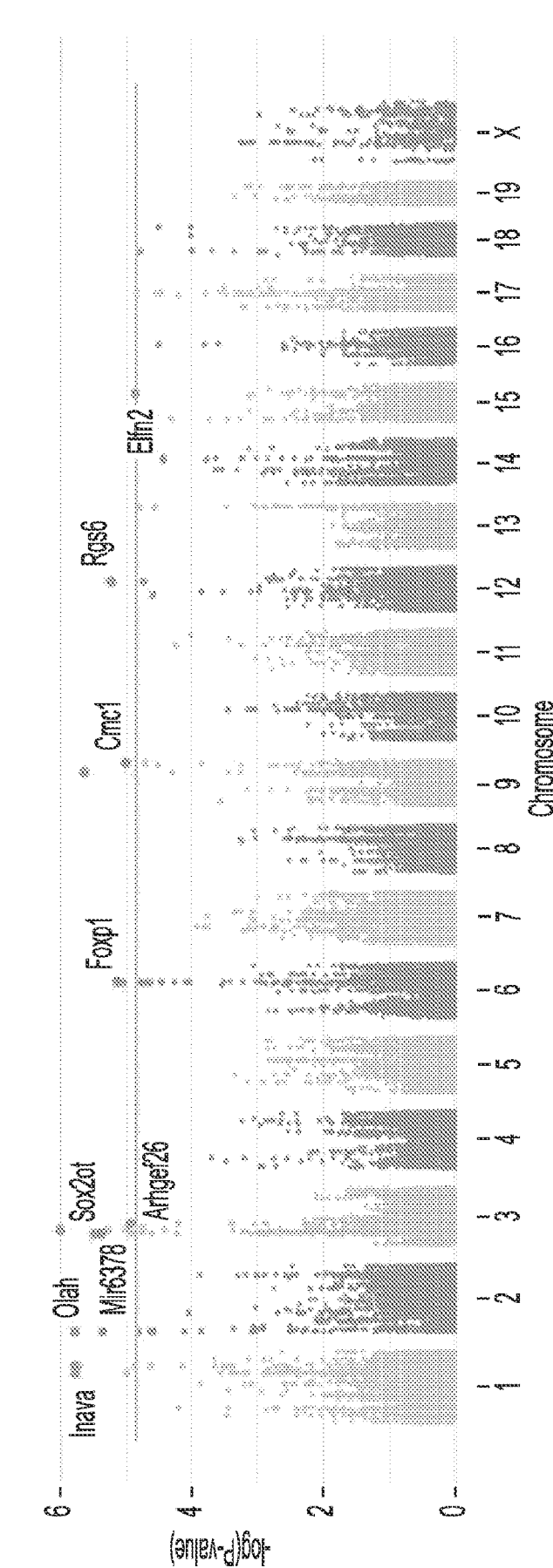
FIG. 23 provides a Manhattan plot for individual phenotypes. The plot was prepared from Linear Mixed Model (LMM) results for each SNP genotype using Wald test for each of the phenotypes.

GWAS analysis resulted in between 2 and 22 peaks that passed the permutation threshold p-value (FIG. 23). Overall, the open field activity had 15 significant peaks; anxiety 10; grooming pattern 76; and grooming quantity had 51 peaks, leading to 130 peaks combined over all the tested phenotypes (FIG. 9C). Pleiotropy was observed with the same loci significantly associated with multiple phenotypes. Pleiotropy was expected because many of the phenotypes were correlated and individual traits may be regulated by similar genetic architecture. For instance, pleiotropy was expected for grooming time in 55 and 20 minutes (GrTime55 and GrTime20) because these are correlated traits. It was also expected that some loci that would regulate open-field activity phenotypes might regulate grooming.

Figure 22C:
Figure 22D:
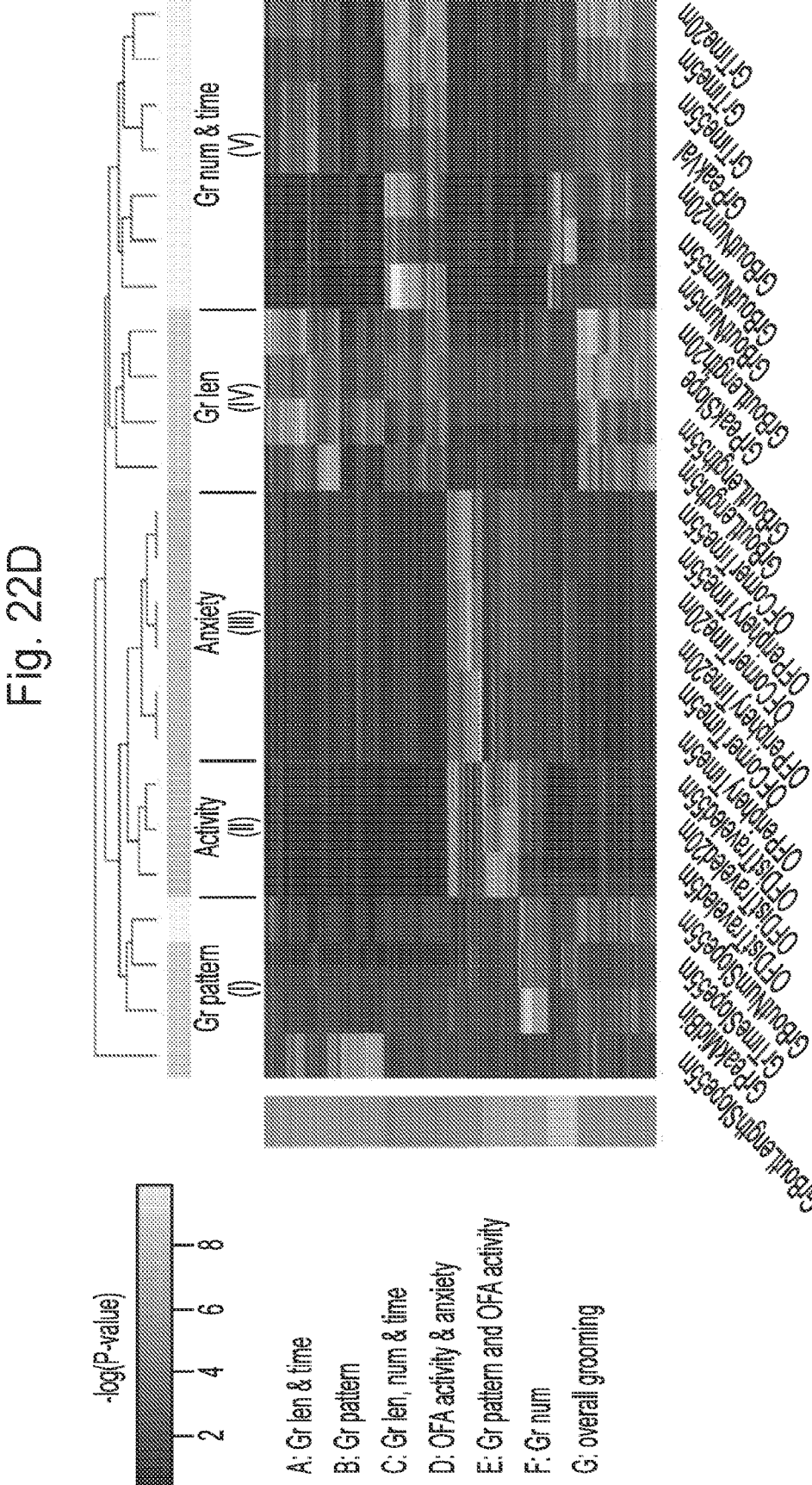

In order to better understand the pleiotropic structure of our GWAS results, a heat map of significant SNPs across all phenotypes was generated. These were then clustered to find sets of SNPs that regulated groups of phenotypes (FIG. 22D). The phenotypes clustered into 5 subgroups consisting of grooming pattern (I), open field activity (II), open field anxiety (III), grooming length (IV), and grooming number and amount (V) (FIG. 22D top x-axis). Seven clusters of SNPs that regulated combinations of these phenotypes were identified (FIG. 22D y-axis). For instance clusters A and G were composed of pleiotropic SNPs that regulated grooming length (IV) and grooming time but SNPs in cluster G also regulated bout number and amount (V). SNP cluster D regulated open-field activity and anxiety phenotypes. Cluster E contained SNPs that regulated grooming and open-field activity and anxiety phenotypes, but most of the SNPs only had significant p-values for either open-field phenotypes or grooming phenotypes but not both, indicating that independent genetic architectures are largely responsible for these phenotypes. The associated regions in GWAS (FIG. 22C) were shaded to mark one of the seven SNP clusters (FIG. 22D). These clusters ranged from 13 to 35 SNPs with the smallest being cluster F, which was mostly pleiotropic for grooming number, and the largest cluster, cluster G, was pleiotropic for most of the grooming-related phenotypes. In order to prioritize genes, the associated genes were ordered based on degree of pleiotropy.

These highly pleiotropic genes included several genes known to regulate grooming, striatal function, neuronal development, and even language. Mammalian Phenotype Ontology Enrichment showed "nervous system development" as the most significant module with 178 genes ($p=7.5 \times 10^{-4}$) followed by preweaning lethality ($p=3.5 \times 10^{-3}$, 189 genes) and abnormal embryo development ($p=5.5 \times 10^{-3}$, 62 genes) (see FIG. 24A-G). Pathway analysis was carried out using pathwAX [Ogris, C. et al., 2016 Nucleic Acids Res July 8; 44(W1):W105-9] using KEGG and Reactome databases. This analysis showed 14 disease pathways that were enriched including Parkinson's (9.68E-09), Huntington's (1.07E-06), Non-alcoholic fatty liver disease (9.31E-06), Alzheimer's (1.15E-05) diseases as the most significantly enriched. Enriched pathways included Oxidative phosphorylation (6.42E-08), Ribosome (0.00000102), RNA transport (0.00000315), Ribosome biogenesis (0.00000465). Reactome enriched pathways included mitochondrial translation termination and elongation (2.50E-19, 5.89E-19, respectively), Ubiquitin-specific processing proteases (1.86E-08). The highest pleiotropic gene was Sox5 which associated with 11 grooming and open-field phenotypes Sox5 has been extensively linked to neuronal differentiation, patterning, and stem cell maintenance [Lefebvre V. 2010 The international Journal of Biochemistry & Cell Biology 42(3):429-432]. Its dis-regulation in humans has been implicated in Lamb-Shaffer syndrome and ASD, both neurodevelopmental disorders [Kwan K Y. In: *International Review of Neurobiology*, vol. 113 Elsevier; 2013.p. 167-205 and Zawerton A, et al., 2020 Genetics in Medicine 22(3):524-537]. 102 genes were associated with 10 phenotypes, and 105 genes were associated with 9 phenotypes. The analysis was limited to genes with at least 6 significantly associated phenotypes, resulting in 860 genes. Other genes included FoxP1, which has been linked to striatal function and regulation of language [Bowers, J. M. & Konopka, G., 2012 Disease Markers 33(5):251-60]. Ctnnb1, regulator of wnt signaling, Grin2b, is a regulator of glutamate signaling. Combined, this analysis indicated genes known to regulate nervous system function and development, and genes known to regulate neurodegenerative diseases as regulators of grooming and open field behaviors. The GWAS analysis also defined the genetic architecture of grooming and open-field behavior in mice.

Example 8

PheWAS

Other studies were performed to link the 860 genes (see Example 7) that were associated with open-field and grooming phenotypes in the mouse with human phenotypes. It was hypothesized that common underlying genetic and neuronal architecture exist between mouse and human, however they give rise to disparate phenotypes in each organism. Thus for example, the misregulation of certain pathways in the mouse may lead to over-grooming phenotypes but in humans the same pathway perturbation may manifest itself as neuroticism or obsessive compulsive disorder. These relationships between phenotypes between organisms can be revealed through identification of common underlying genetic architectures.

Figure 25:
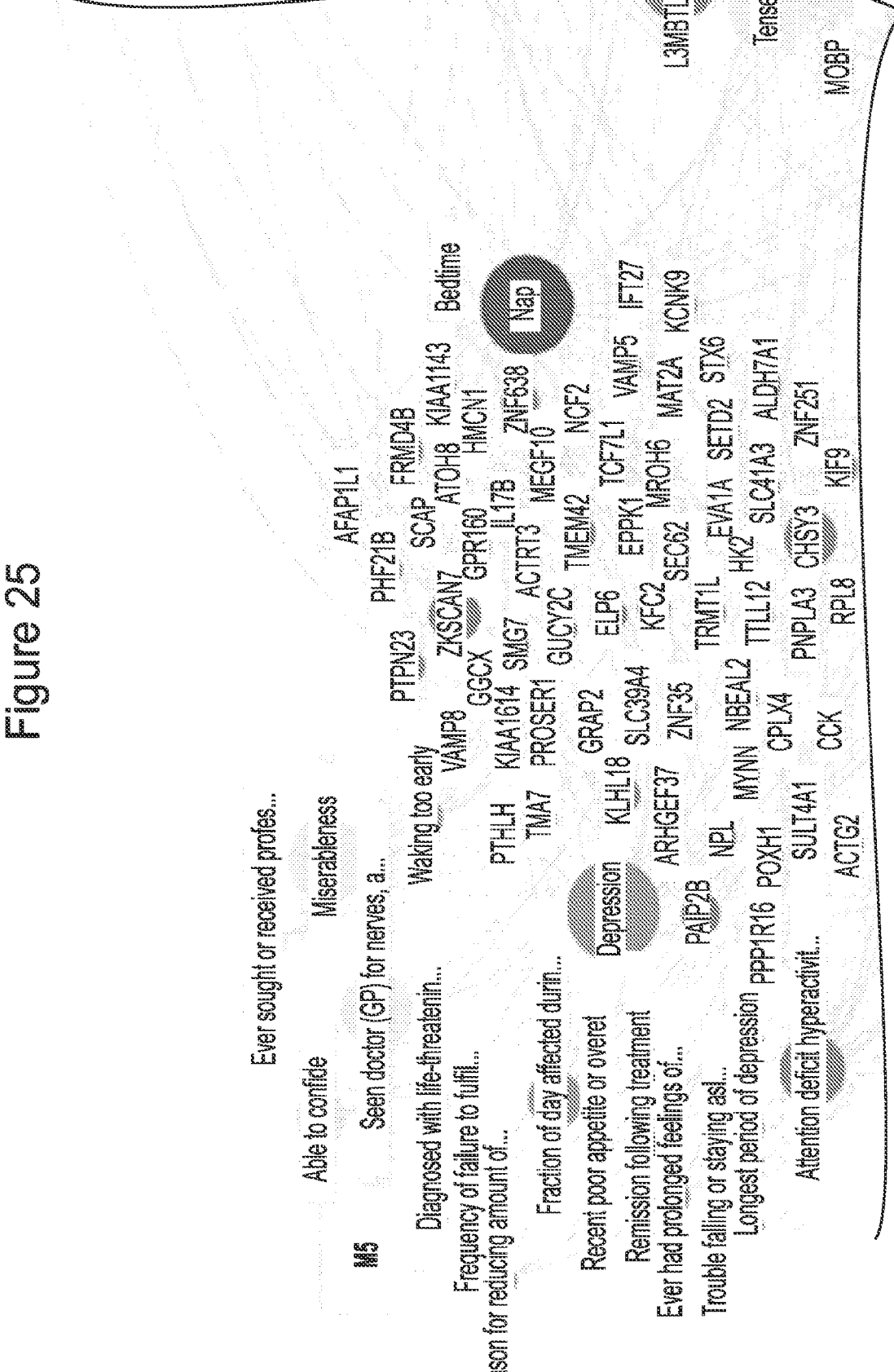
FIG. 25 provides illustration showing Human-Mouse trait relations through weighted bipartite network of PheWAS results. The width of an edge between a gene node (filled circles) and a Psychiatric trait node is proportional to the association strength (− log 10(p value)). The size of a node is proportional to the number of associated genes or traits and the color of a trait node corresponds to the subchapter level in the Psychiatric domain. Eight modules were identified and visualized using Gephi 0.9.2 software.
Figure 25:
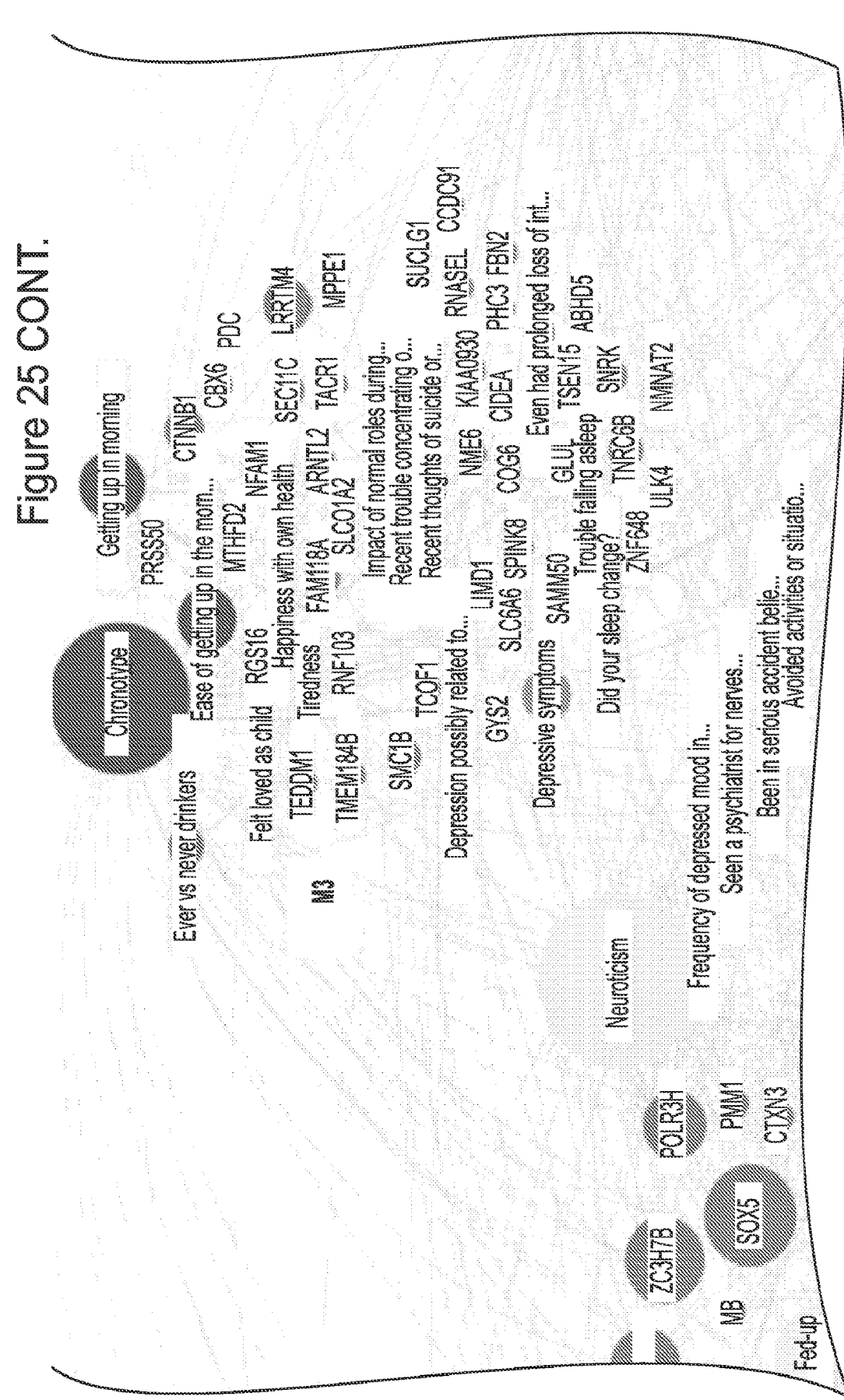
Figure 25:
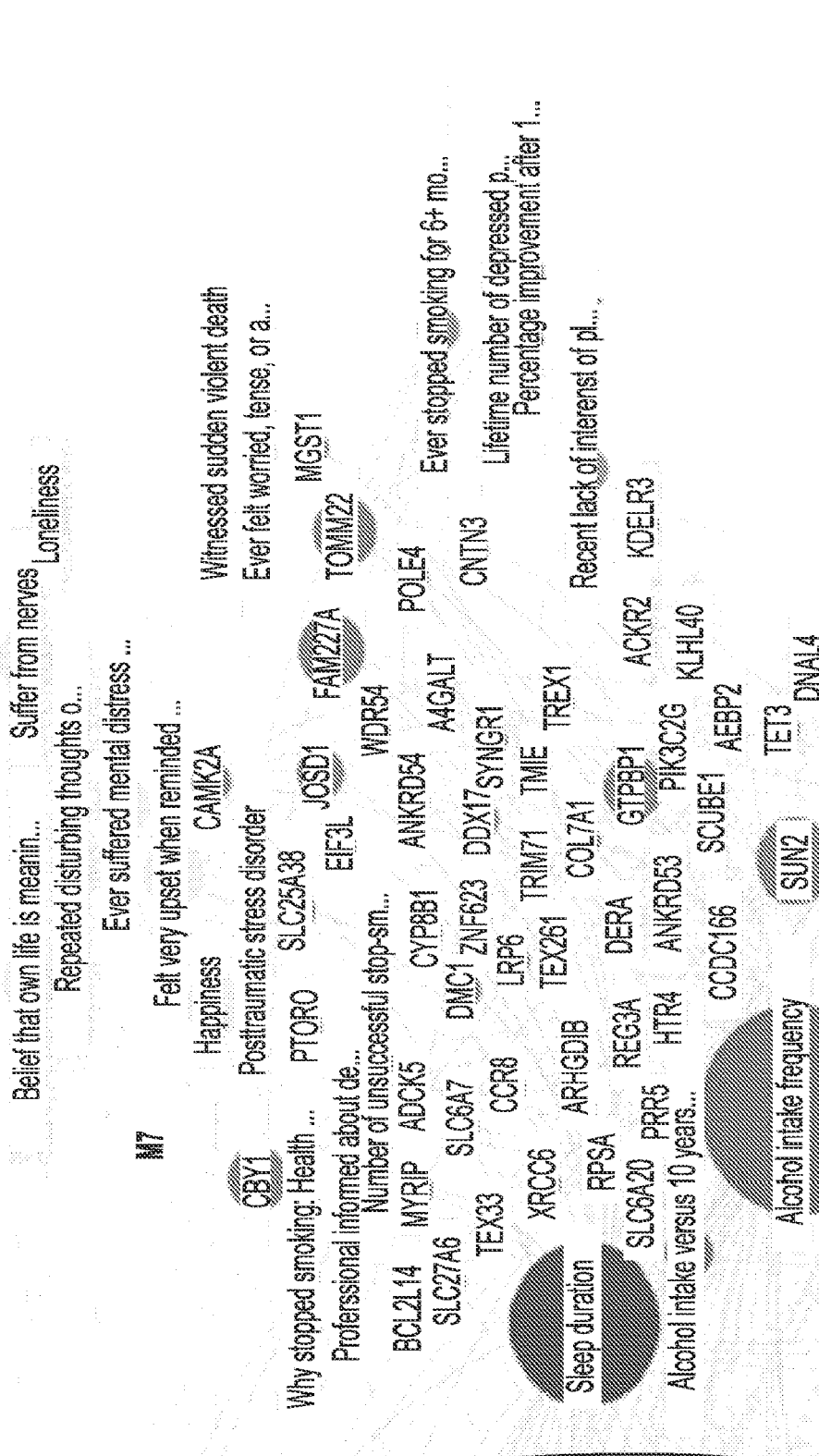
Figure 25:
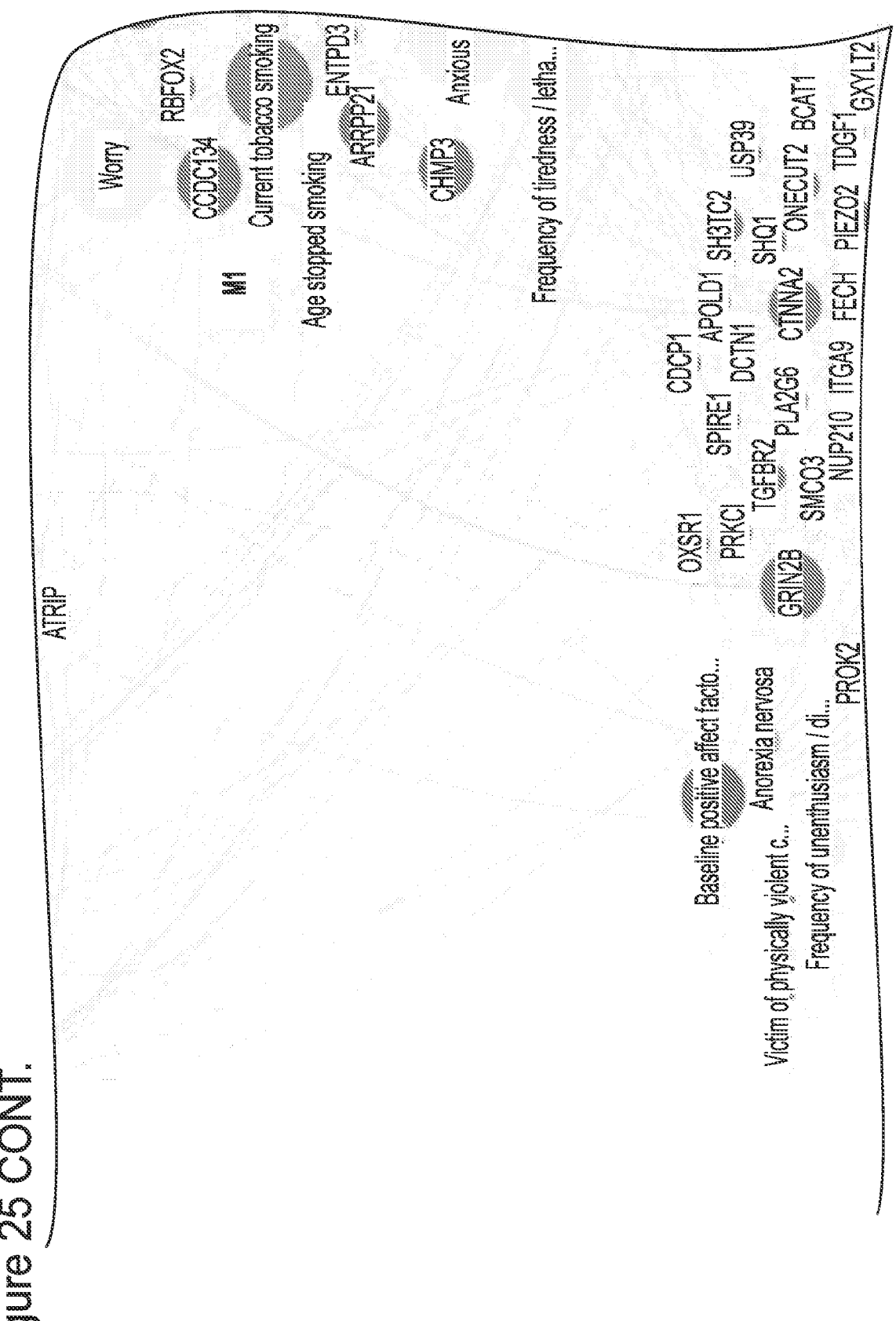
Figure 25:
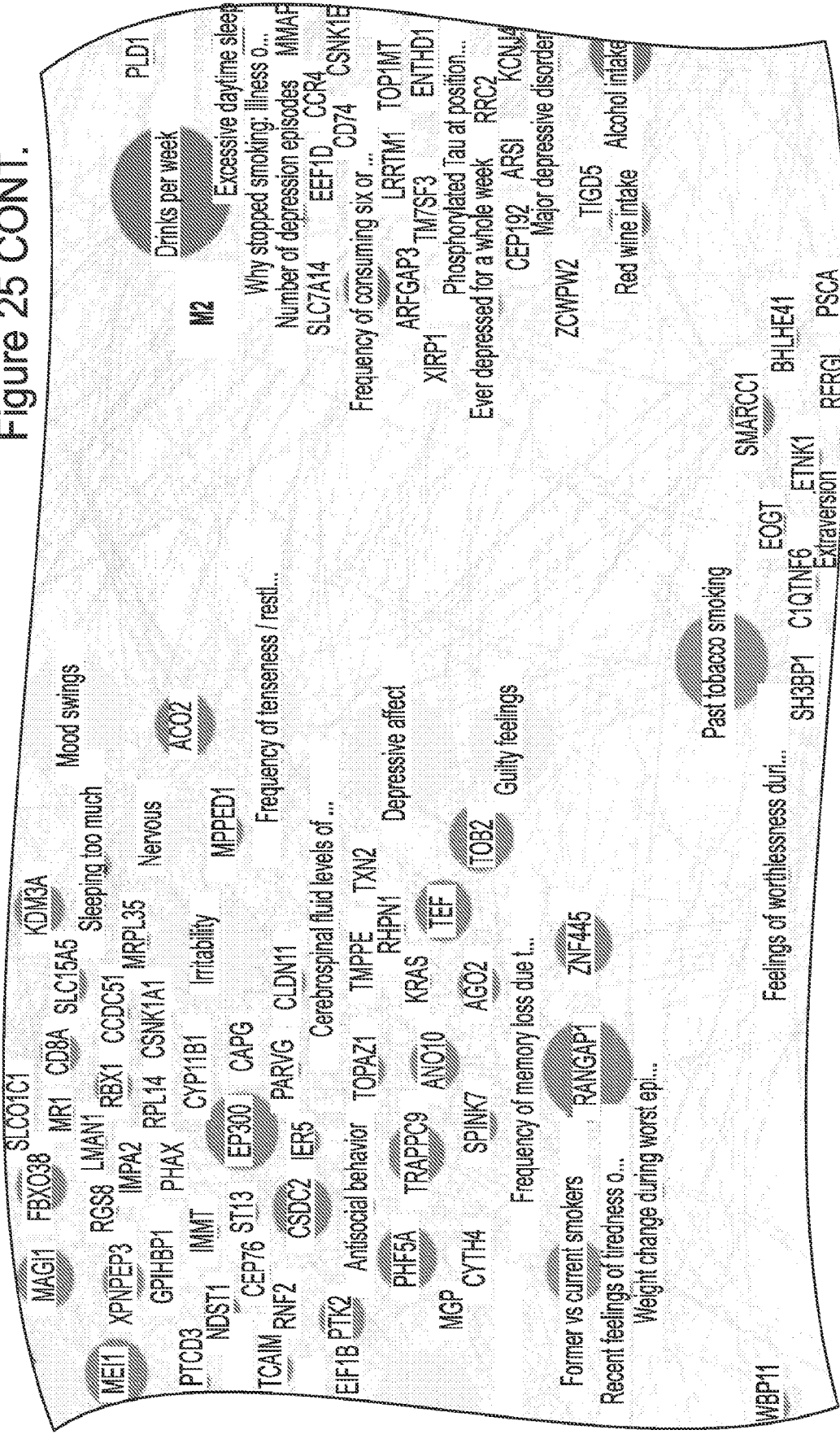
Figure 25:
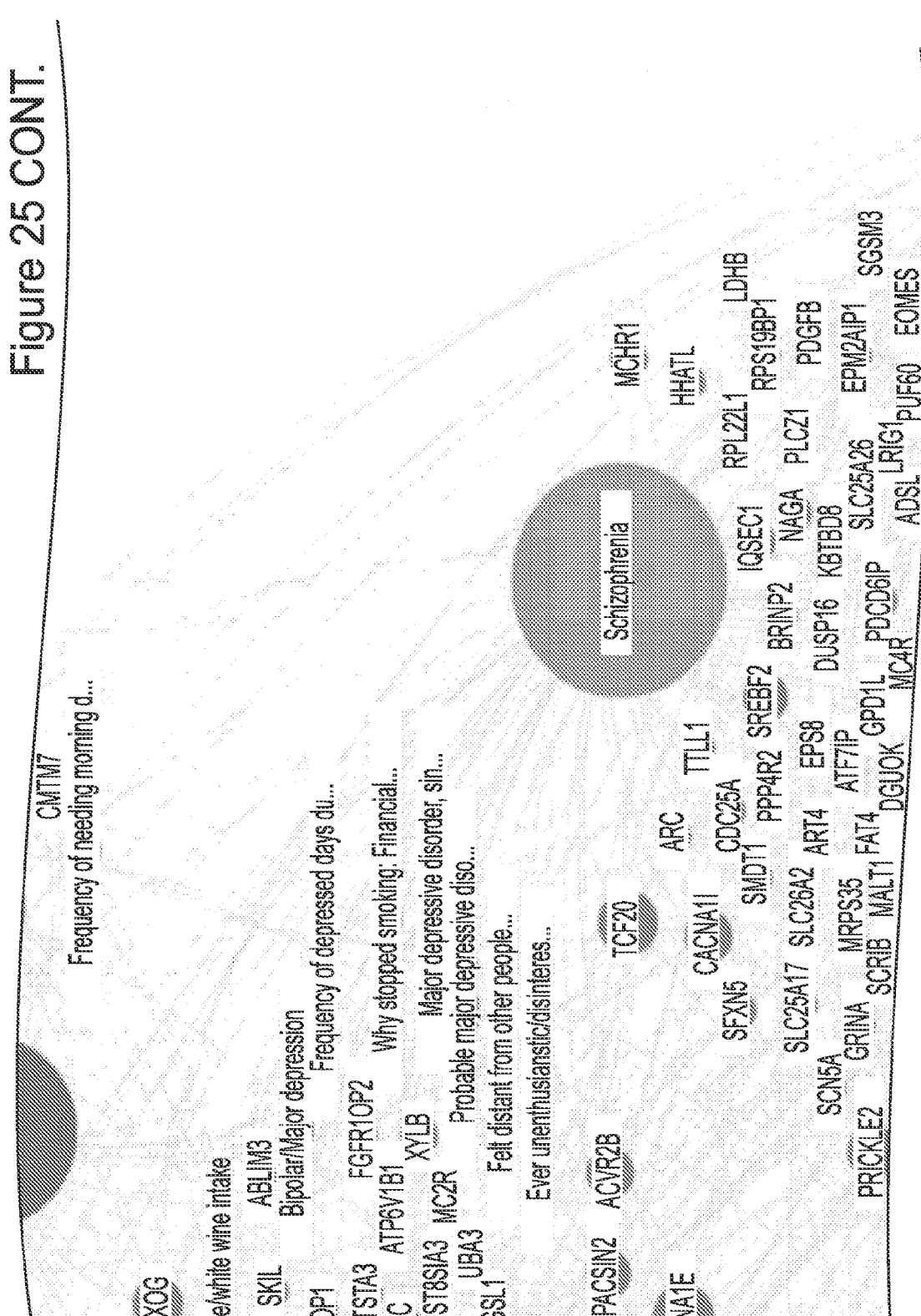
Figure 25:
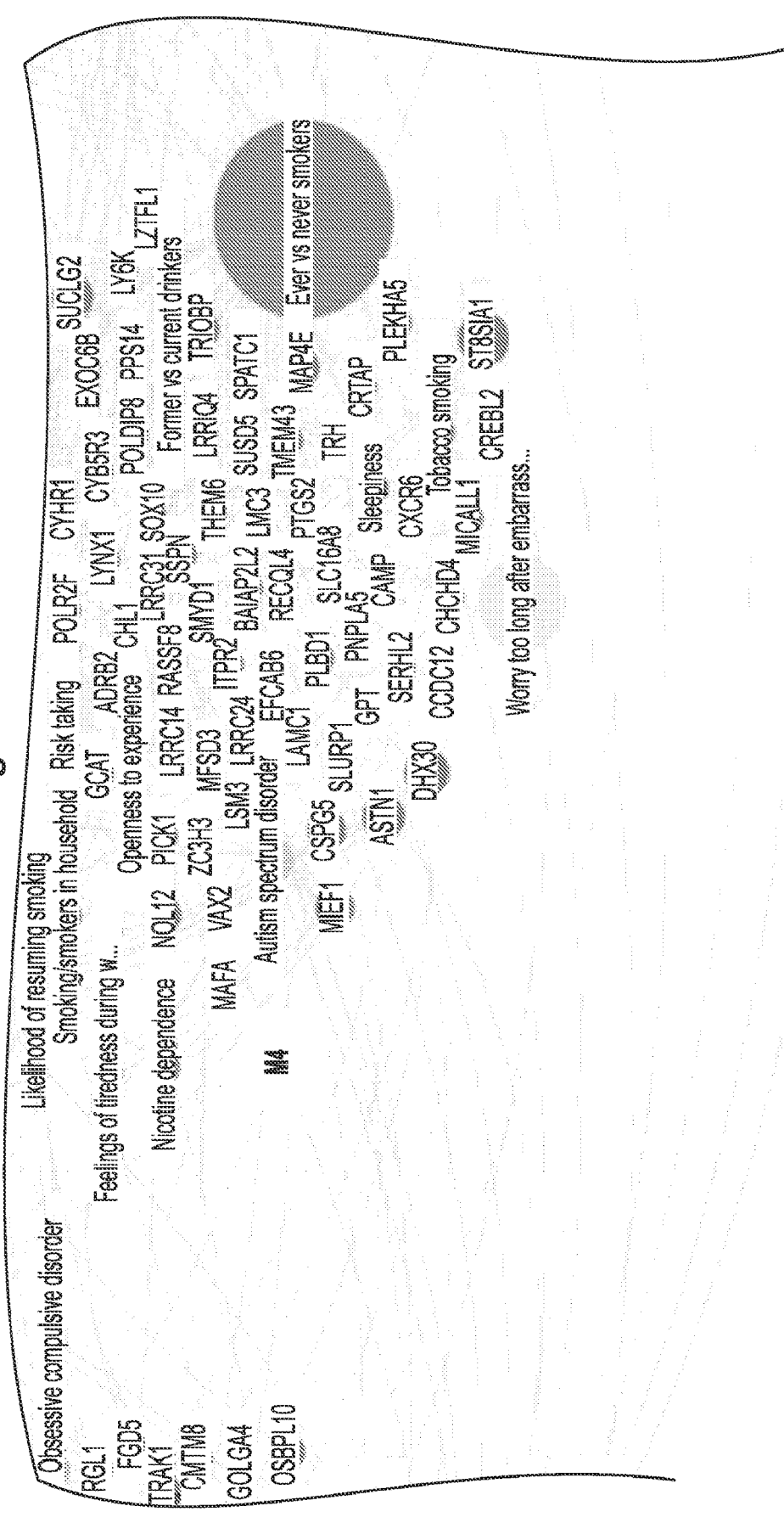

In order to link the mouse genetic circuit of grooming to human phenotypes, a PheWAS was conducted with Psychiatric Genetics GWAS catalog. A first step included identification of human orthologs of the 860 mouse grooming and open-field genes with at least six degrees of pleiotropy. For each human ortholog, PheWAS summary statistics were downloaded from gwasATLAS (//atlas.ctglab.nl/) [Watanabe K, et al., 2019 Nature Genetics 51(9):1339-1348]. The gwasATLAS currently contains 4756 GWAS from 473 unique studies across 3302 unique traits that are classified into 28 domains. Studies were focused on the association in Psychiatric domain with gene-level p value≤0.001. In addition, to visualize and cluster these associations, the relationships between genes and psychiatric traits were represented by a weighted bipartite network, in which the width of an edge between a gene node and a Psychiatric trait node was proportional to the association strength [- log 10(p value)]. The size of a node was proportional to the number of associated genes or traits and the shading of a trait node corresponded to the subchapter level in the Psychiatric domain. To identify modules within this network, an improved community detection algorithm was applied for maximizing weighted modularity in weighted bipartite networks [Dormann C F. & Strauss R. 2014 Methods in Ecology and Evolution 5(1):90-98]. This network was used to detect communities as input to produce a ranked list of communities based on modularity score, where high-ranking communities represent promising candidates for further research [Newman M E. & Girvan M. 2004 Physical Review E 69(2):026113]. This analysis resulted in 8 gene-phenotype modules (FIG. 25). These modules contained between 15 and 32 individual phenotypes and between 41 and 103 genes. At the subchapter level, modules were enriched for temperament and personality phenotypes, mental and behavioral disorders (schizophrenia, bipolar, dementia), addiction (alcohol, tobacco, cannabinoid) obsessive-compulsive disorder, anxiety, and sleep.

Surprisingly, the results identified identical genes that showed high levels of pleiotropy in mouse GWAS and the resulting human PheWAS. FOXP1 was the most pleiotropic gene with 35 associations and SOXS with 33 associations. This network was used to detect communities as input to produce a ranked list of communities based on modularity score, where high-ranking communities represent promising candidates for further research. Modularity scores of the 8 modules ranged from 0.028 to 0.083 and module 1 was ranked at the top with a modularity score of 0.103). Furthermore, Simes test was used to combine the p values of genes to obtain an overall p value for the association of each Psychiatric trait. Then the median of association [– log 10(Simes p value)] was calculated in each detected community for prioritization. Similarly, module 1 ranked at the top of eight modules (median LOD=5.29). Module 1 was primarily composed of Temperament and Personality phenotypes, including neuroticism, mood swings, irritability traits. Genes in this module have high level of pleiotropy in both human PheWAS and mouse GWAS. These genes include SOXS, associated with 33 human phenotypes, RANGAP1, GRIN2B, and others. Eight of 10 highest pleiotropic genes from the PheWAS analysis belonged in this module. Genes in this module included SOXS, which was the second most pleiotropic gene in the PheWAS study with 33 significant associations, RANGAP1, with 31 associations, EP300 with 23 significant associations. In conclusion, PheWAS analysis linked genes that upregulate grooming and other open-field behaviors to human phenotypes. These human phenotypes include personality traits, addiction, and schizophrenia. It was also found that similar genes were highly pleiotropic in mouse GWAS and human PheWAS analysis.

Summary and Discussion Relating to Examples 1-8

Grooming is an ethologically conserved, neurobiologically important behavior that is of interest to the behavioral genetics community. It is often used as an endophenotype for several psychiatric illness and is a prototypical example of stereotyped, patterned behavior and the ability to automatically quantify grooming behavior is a needed tool [Spruijt B M. et al., 1992 Physiological reviews 72(3):825-852; Kalueff A V, et al., Neurobiology of grooming behavior. Cambridge University Press; 2010; and Kalueff A V. Et al., 2016 Nature Reviews Neuroscience 17(1):45]. In addition, the ability to detect grooming behavior, with highly variable posture and temporal length, serves as a prototype for other behaviors. Work described herein presents a neural network approach towards automated model organism behavioral classification and ethogram generation.

The approach was implemented for grooming behavior in mice, which is a complex behavior that poses challenges for existing automated systems and the system and methods described herein achieved human level performance. Using this grooming behavior classifier, a large data set was analyzed. The resulting data demonstrated the stability of grooming as a behavioral metric by running a covariate analysis. Mouse GWAS study and human PheWAS study were also performed in order to understand the underlying genetic architecture of grooming and open-field behavior in the laboratory mouse and to link them to human traits.

Although the machine learning community has implemented a wide variety solutions for human action detection, few applications have been applied to animal behavior. This could be due to a variety of reasons such as the wide availability of human action datasets and the stringent performance requirements for bio-behavioral research. It was observed that the cost of achieving this stringent performance is very high, requiring a large quantity of annotations. More often than not, prior experimental paradigms were short or small enough to cost less to simply annotate the data without automation.

Other machine learning approaches have been applied to this automated annotation of behavioral data. It was observed that a 3D convolutional neural network outperformed a JAABA classifier when trained on the same training dataset. This improvement was not uniform over all samples and was instead localized to certain types of grooming bouts. This suggests that although the JAABA classifier is powerful and has utility for smaller more uniform datasets, experiments and behaviors with diverse expression require a more powerful machine learning approach. With the grooming classifier, genetic and environmental factors that regulate this behavior were determined. In a large dataset with two reference strains, C57BL/6J and C67BL/6N, that was collected over 18-month period, studies were conducted that assessed effects of several factors that varied over time in the dataset including, sex, strain, age, time of day, season, tester, room origin, white noise, and body weight. All these mice were housed in identical conditions for at least a week prior to testing. A strong effect of sex, time of test, and even season were observed.

Tester effects have been widely observed in previous open field in both mice and rats [Walsh R N. & Cummins R A. 1976 Psychological Bulletin 83(3):482; McCall R B. et al., 1969 Developmental Psychology 1(6p1):771; and Bohlen M. et al., 2014 Behavioural Brain Research 272:46-54]. A recent study demonstrated that male experimenters or even clothes of males elicit stress responses from mice leading to increased thigmotaxis [Sorge R E. et al., 2014 Nature Methods 11(6):629]. However, experimenter effects are not always observed across open leld studies [Lewejohann L. et al., 2006 Genes, Brain and Behavior 5(1):64-72]. Results of the studies described herein indicated that room of origin had a strong effect on grooming. Grooming in mice shipped from Jackson Laboratory production rooms was compared to that of mice bred in a room adjacent to the phenotyping room. It was observed that shipped mice could vary in total grooming duration compared to mice that did not experience shipping. There was no clear directionality of the effect and in some cases the effect size was high (Z>1). The same strain shipped from different rooms had higher or lower total grooming amount. It was hypothesized that the change in grooming was due to stress, which has previously been demonstrated to alter this behavior [Kalueff A V. et al., 2016 Nature Reviews Neuroscience 17(1):45]. Presumably, all external mice had similar experience of shipping from the production rooms to the testing area where they were housed identically for at least one week prior to testing. Thus, the potential differential stress experience was in the room of origin where the mouse was born and held until shipping. This is a point of caution for use of this behavior as an endophenotype.

A large strain survey was carried out to characterize grooming behavior in the laboratory mouse. Three types of grooming patterns were found under the test conditions. Type 1 consisted of mice that escalated and de-escalated grooming within the 55-minute open-field test. Strains in this group were often sleeping by the end of the assay, indicating a low arousal state towards the end of the assay. It was hypothesized that these strains used grooming as a form of successful de-arousal, a behavior that has been previously noted in rats, birds, and apes [Spruijt B M. et al., 1992 Physiological reviews 72(3):825-852 and Delius J D. 1970 Psychologische Forschung 33(2):165-188. doi: 10.1007/BF00424983]. Similar to type 1, type 2 groomers escalated grooming quickly to reach peak grooming, however, this group did not seem to de-escalate grooming during the assay. It was hypothesized that these strains needed longer time or had some deficiency in de-arousal under the test conditions. Type3 strains escalated for the duration of the assay indicating they had not reached peak grooming under the assay conditions. BTBR is a member of type 2 group with prolonged high levels of grooming from an early point, perhaps indicating a hyperaroused state, or an inability to de-arouse. BTBR have previously been shown to have high arousal states and altered dopamine function which may lead to the sustained high levels of grooming. It is postulated that other strains in the type 2 grooming class may also show endophenotypic features of ASD.

Results of the studies indicated that the wild-derived strains had distinct patterns of grooming compared to classical strains. Wild-derived strains groomed significantly more and had longer grooming bouts than classical strains. In the grooming clustering analysis most of the wild-derived strains belonged to Type 1 or 2, whereas most classical strains belonged in Type 3. In addition to *M.m domesticus*, the wild-derived inbred lines that were tested represent *M.m musculus*, *M.m castaneous*, and *M.m molossinus* subspecies. Even though there are dozens of classical inbred strains, there are approximately 5 million SNPs between two classical inbred laboratory strains such as C57BL/6J and DBA2J [Keane T M. et al., 2011 Nature. 477(7364):289-294]. Indeed, over 97% of the genome of classical strains can be explained by fewer than ten haplotypes indicating small number of classes within which all strains are identical by descent with respect to common ancestor [Yang H. et al., 2011 Nature Genetics 43(7):648]. In contrast, wild-derived inbred strains such as CAST/EiJ and 599 PWK/PhJ have over 17 million SNPs compared to B6J, and WSB/EiJ have 8 million SNPs. Thus, the seven wild-derived strains that were tested represent far more of the genetic diversity present in the natural mouse population than the numerous classical inbred laboratory strains. Behaviors seen in the wild-derived strains are more likely to represent behaviors the natural mouse population.

Classical laboratory strains are derived from mouse fanciers in China, Japan, and Europe before being co-opted for biomedical research [Morse H C. 1978 Proceedings of a Workshop, Bethesda, Maryland, Feb. 14-16, 1978. Acad. Press; 1978 and Silver L M. Mouse Genetics: Concepts and Applications. Oxford University Press; 1995]. As a result, even though there are hundreds of classical strains, genetic variance is limited within these strains [Yang H. et al., 2011 Nature Genetics 43(7):648]. Wild-derived strains were developed specifically to overcome these limitations of the classical strains [Poltorak A. et al., 2018 Mammalian Genome 29(7-8):577-584]. Mouse fanciers breed mice for visual and behavioral distinctiveness, and many exhibit them in competitive shows. Mouse fanciers judge mice on "condition and temperament" and suggest that "it is useless to show a mouse rough in coat or in anything but the mouse perfect condition" [Davies C. Fancy Mice: Their Varieties and Management as Pets or for Show, Including the Latest Scientific Information as to Breeding for Colour. LU Gill; 1912]. Much like dogs and horses, the "best individuals should be mated together regardless of relationship as long as mice are large, hardy, and free from disease" [Davies C. Fancy Mice: Their Varieties and Management as Pets or for Show, Including the Latest Scientific Information as to Breeding for Colour. LU Gill; 1912]. It is plausible that normal levels of grooming behavior seen in wild mice was considered unhygienic or indicative of parasites such as lice, tics, fleas, mites. High grooming could be interpreted as poor condition and would lead the mouse fancier to select mouse strains with low grooming behaviors. This selection could account for low grooming seen in the classical strains.

The strain survey data was used to conduct a mouse GWAS which identified xx genetic loci that regulates heritable variation in open-field and grooming behaviors. Results indicated that a majority of the grooming traits are moderately to highly heritable. In studies exemplified herein, 862 genes that were pleiotropic were closely analyzed and the results indicated genes and pathways known to regulate neuronal development and function. It was identified that these associated regions belonged to one of seven clusters that regulate combinations of open field and grooming phenotypes. One previous study using BXD recombinant inbred panel identified 1 significant locus on chromosome 4 that regulates grooming and open-field activity [Delprato A. et al., 2017 Genes, Brain and Behavior 16(8): 790-799]. Also, as described herein, a PheWAS was conducted with these genes and psychiatric traits were identified that are associated with these genes. This approach permitted linking of mouse and human phenotypes through the underlying genetic architecture. This approach linked human temperament and personality traits, schizophrenia, bipolar disorder traits to mouse open-field and grooming phenotypes. Grooming can be used as a model of human grooming disorders such as tricotillomania. However, grooming is regulated by the basal ganglia and other brain regions and can be used as an endophenotype for many psychiatric traits, including ASD, schizophrenia, and Parkinson's [Kalueff A V. et al., 2016 Nature Reviews Neuroscience 17(1):45]. Results of the studies herein linked grooming to temperament and personality traits, schizophrenia, bipolar disorder, among others. The GWAS results provided increased understanding of the genetic architecture of grooming behavior.

In conclusion, experiments and studies described herein demonstrate a neural network based machine learning approach for action detection in mice, and its application towards grooming behavior. This tool has now been, and can be used to characterize grooming behavior and its underlying genetic architecture in the laboratory mice and other mammals. The approach to grooming can be carried out using standard open-field apparatus and should be of use to the behavioral neuroscience community.

Example Devices and Systems

One or more of the trained models of the system(s) 150 may take many forms, including a neural network. A neural network may include a number of layers, from an input layer through an output layer. Each layer is configured to take as input a particular type of data and output another type of data. The output from one layer is taken as the input to the next layer. While values for the input data/output data of a particular layer are not known until a neural network is actually operating during runtime, the data describing the neural network describes the structure, parameters, and operations of the layers of the neural network.

One or more of the middle layers of the neural network may also be known as the hidden layer. Each node of the hidden layer is connected to each node in the input layer and each node in the output layer. In the case where the neural network comprises multiple middle networks, each node in a hidden layer will connect to each node in the next higher layer and next lower layer. Each node of the input layer represents a potential input to the neural network and each node of the output layer represents a potential output of the neural network. Each connection from one node to another node in the next layer may be associated with a weight or score. A neural network may output a single output or a weighted set of possible outputs.

In one aspect, the neural network may be a fully connected convolutional neural network (CNN) having regularized versions of multilayer perceptrons. In a fully connected network each neuron in one layer is connected to all neurons in the next layer. Typical ways of regularization include adding some form of magnitude measurement of weights to the loss function. CNN take a different approach towards regularization: they take advantage of the hierarchical pattern in data and assemble more complex patterns using smaller and simpler patterns.

In one aspect, the neural network may be constructed with recurrent connections such that the output of the hidden layer of the network feeds back into the hidden layer again for the next set of inputs. Each node of the input layer connects to each node of the hidden layer. Each node of the hidden layer connects to each node of the output layer. The output of the hidden layer is fed back into the hidden layer for processing of the next set of inputs. A neural network incorporating recurrent connections may be referred to as a recurrent neural network (RNN).

In some embodiments, the neural network may be a long short-term memory (LSTM) network. In some embodiments, the LSTM may be a bidirectional LSTM. The bidirectional LSTM runs inputs from two temporal directions, one from past states to future states and one from future states to past states, where the past state may correspond to characteristics for the video data for a first time frame and the future state may corresponding to characteristics for the video data for a second subsequent time frame.

Processing by a neural network is determined by the learned weights on each node input and the structure of the network. Given a particular input, the neural network determines the output one layer at a time until the output layer of the entire network is calculated.

Connection weights may be initially learned by the neural network during training, where given inputs are associated with known outputs. In a set of training data, a variety of training examples are fed into the network. Each example typically sets the weights of the correct connections from input to output to 1 and gives all connections a weight of 0. As examples in the training data are processed by the neural network, an input may be sent to the network and compared with the associated output to determine how the network performance compares to the target performance. Using a training technique, such as back propagation, the weights of the neural network may be updated to reduce errors made by the neural network when processing the training data.

Various machine learning techniques may be used to train and operate models to perform various steps described herein, such as user recognition feature extraction, encoding, user recognition scoring, user recognition confidence determination, etc. Models may be trained and operated according to various machine learning techniques. Such techniques may include, for example, neural networks (such as deep neural networks and/or recurrent neural networks), inference engines, trained classifiers, etc. Examples of trained classifiers include Support Vector Machines (SVMs), neural networks, decision trees, AdaBoost (short for "Adaptive Boosting") combined with decision trees, and random forests. Focusing on SVM as an example, SVM is a supervised learning model with associated learning algorithms that analyze data and recognize patterns in the data, and which are commonly used for classification and regression analysis. Given a set of training examples, each marked as belonging to one of two categories, an SVM training algorithm builds a model that assigns new examples into one category or the other, making it a non-probabilistic binary linear classifier. More complex SVM models may be built with the training set identifying more than two categories, with the SVM determining which category is most similar to input data. An SVM model may be mapped so that the examples of the separate categories are divided by clear gaps. New examples are then mapped into that same space and predicted to belong to a category based on which side of the gaps they fall on. Classifiers may issue a "score" indicating which category the data most closely matches. The score may provide an indication of how closely the data matches the category.

In order to apply the machine learning techniques, the machine learning processes themselves need to be trained. Training a machine learning component such as, in this case, one of the first or second models, requires establishing a "ground truth" for the training examples. In machine learning, the term "ground truth" refers to the accuracy of a training set's classification for supervised learning techniques. Various techniques may be used to train the models including backpropagation, statistical learning, supervised learning, semi-supervised learning, stochastic learning, or other known techniques.

Figure 26:
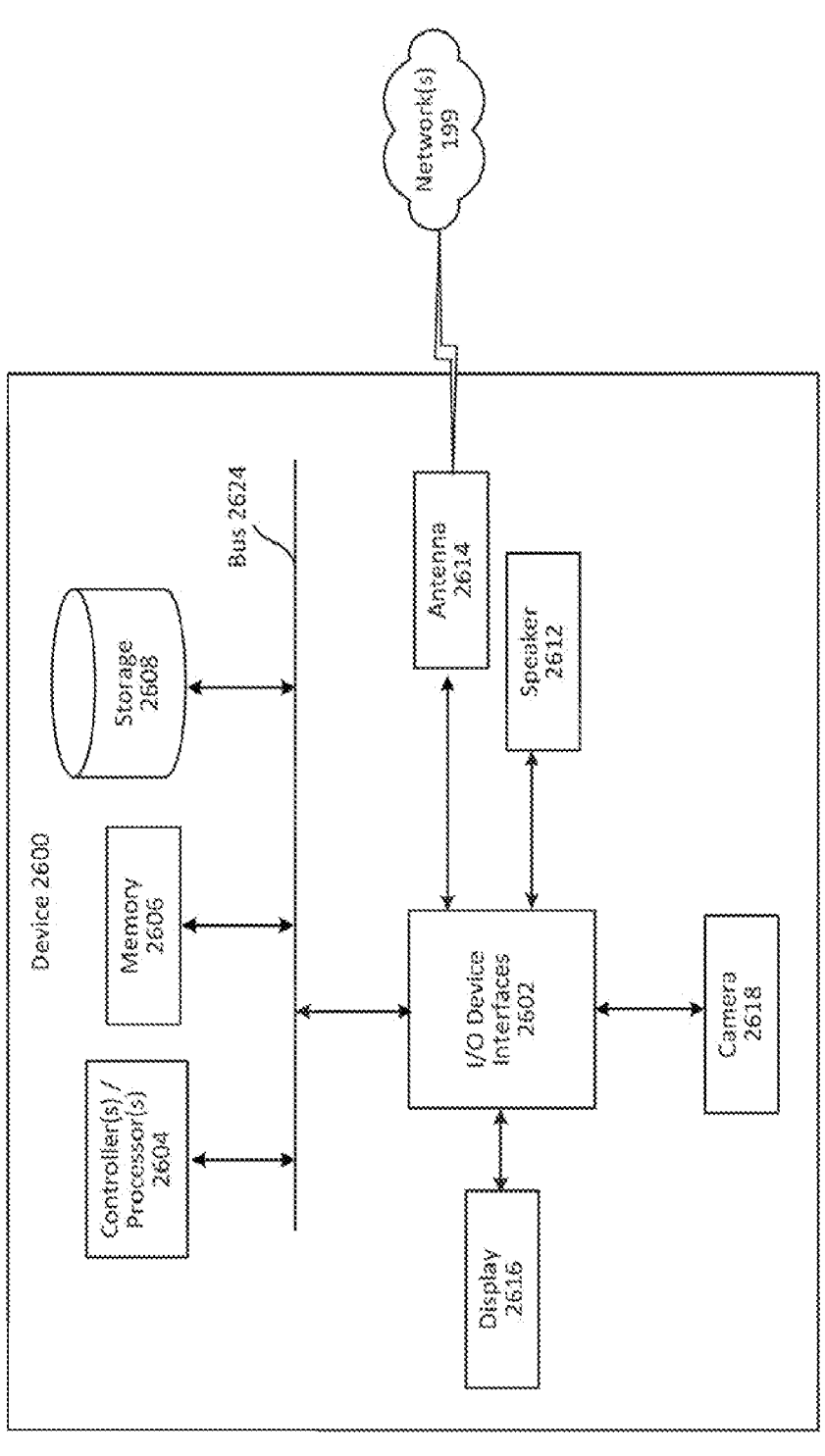
FIG. 26 is a block diagram conceptually illustrating example components of a device according to embodiments of the present disclosure.
Figure 27:
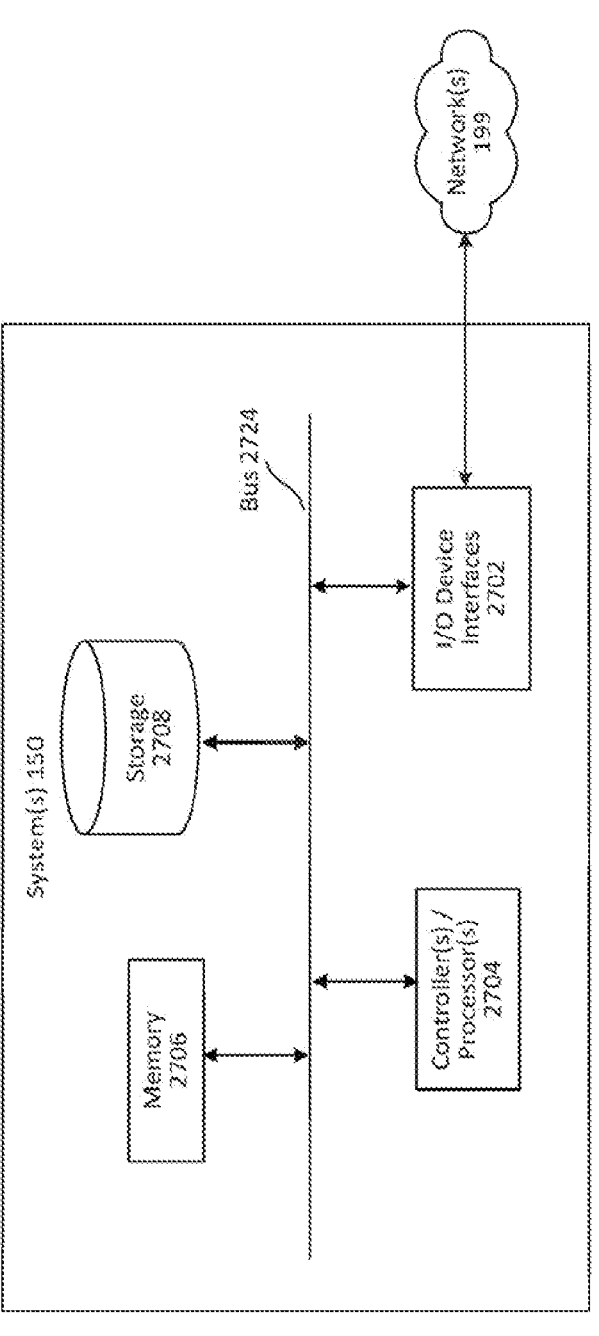
FIG. 27 is a block diagram conceptually illustrating example components of a server according to embodiments of the present disclosure.

FIG. 26 is a block diagram conceptually illustrating a device 2600 that may be used with the system. FIG. 27 is a block diagram conceptually illustrating example components of a remote device, such as the system(s) 150, which may assist processing of video data, detecting subject behavior, etc. A system(s) 150 may include one or more servers. A "server" as used herein may refer to a traditional server as understood in a server/client computing structure but may also refer to a number of different computing components that may assist with the operations discussed herein. For example, a server may include one or more physical computing components (such as a rack server) that are connected to other devices/components either physically and/or over a network and is capable of performing computing operations. A server may also include one or more virtual machines that emulates a computer system and is run on one or across multiple devices. A server may also include other combinations of hardware, software, firmware, or the like to perform operations discussed herein. The server(s) may be configured to operate using one or more of a client-server model, a computer bureau model, grid computing techniques, fog computing techniques, mainframe techniques, utility computing techniques, a peer-to-peer model, sandbox techniques, or other computing techniques.

Multiple systems 150 may be included in the overall system of the present disclosure, such as one or more systems 150 for determining the different orientations for the frames, one or more systems 150 for executing a first trained model to process the different sets of frames, one or more systems 150 for executing a second trained to process the different sets of frames, one or more systems 150 for aggregating the results of the different trained models, one or more systems 150 for training/configuring the different trained models, etc. In operation, each of these systems may include computer-readable and computer-executable instructions that reside on the respective device 150, as will be discussed further below. Each of these devices (2600/150) may include one or more controllers/processors (2604/2704), which may each include a central processing unit (CPU) for processing data and computer-readable instructions, and a memory (2606/2706) for storing data and instructions of the respective device. The memories (2606/2706) may individually include volatile random access memory (RAM), non-volatile read only memory (ROM), non-volatile magnetoresistive memory (MRAM), and/or other types of memory. Each device (2600/150) may also include a data storage component (2608/2708) for storing data and controller/processor-executable instructions. Each data storage component (2608/2708) may individually include one or more non-volatile storage types such as magnetic storage, optical storage, solid-state storage, etc. Each device (2600/150) may also be connected to removable or external non-volatile memory and/or storage (such as a removable memory card, memory key drive, networked storage, etc.) through respective input/output device interfaces (2602/2702).

Computer instructions for operating each device (2600/150) and its various components may be executed by the respective device's controller(s)/processor(s) (2604/2704), using the memory (2606/2706) as temporary "working" storage at runtime. A device's computer instructions may be stored in a non-transitory manner in non-volatile memory (2606/2706), storage (2608/2708), or an external device(s). Alternatively, some or all of the executable instructions may be embedded in hardware or firmware on the respective device in addition to or instead of software.

Each device (2600/150) includes input/output device interfaces (2602/2702). A variety of components may be connected through the input/output device interfaces (2602/2702), as will be discussed further below. Additionally, each device (2600/150) may include an address/data bus (2624/2724) for conveying data among components of the respective device. Each component within a device (2600/150) may also be directly connected to other components in addition to (or instead of) being connected to other components across the bus (2624/2724).

Referring to FIG. 26, the device 2600 may include input/output device interfaces 2602 that connect to a variety of components such as an audio output component such as a speaker 2612, a wired headset or a wireless headset (not illustrated), or other component capable of outputting audio. The device 2600 may additionally include a display 2616 for displaying content. The device 2600 may further include a camera 2618.

Via antenna(s) 2614, the input/output device interfaces 2602 may connect to one or more networks 199 via a wireless local area network (WLAN) (such as WiFi) radio, Bluetooth, and/or wireless network radio, such as a radio capable of communication with a wireless communication network such as a Long Term Evolution (LTE) network, WiMAX network, 3G network, 4G network, 5G network, etc. A wired connection such as Ethernet may also be supported. Through the network(s) 199, the system may be distributed across a networked environment. The I/O device interface (2602/2702) may also include communication components that allow data to be exchanged between devices such as different physical servers in a collection of servers or other components.

The components of the device(s) 2600 or the system(s) 150 may include their own dedicated processors, memory, and/or storage. Alternatively, one or more of the components of the device(s) 2600, or the system(s) 150 may utilize the I/O interfaces (2602/2702), processor(s) (2604/2704), memory (2606/2706), and/or storage (2608/2708) of the device(s) 2600, or the system(s) 150, respectively.

As noted above, multiple devices may be employed in a single system. In such a multi-device system, each of the devices may include different components for performing different aspects of the system's processing. The multiple devices may include overlapping components. The components of the device 2600, and the system(s) 150, as described herein, are illustrative, and may be located as a stand-alone device or may be included, in whole or in part, as a component of a larger device or system.

The concepts disclosed herein may be applied within a number of different devices and computer systems, including, for example, general-purpose computing systems, video/image processing systems, and distributed computing environments.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers and speech processing should recognize that components and process steps described herein may be interchangeable with other components or steps, or combinations of components or steps, and still achieve the benefits and advantages of the present disclosure.

Moreover, it should be apparent to one skilled in the art, that the disclosure may be practiced without some or all of the specific details and steps disclosed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage medium may be implemented by a volatile computer memory, non-volatile computer memory, hard drive, solid-state memory, flash drive, removable disk, and/or other media. In addition, components of system may be implemented as in firmware or hardware.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without other input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

All references, patents and patent applications and publications that are cited or referred to in this application are incorporated by reference in their entirety herein.

What is claimed is:

1. A computer-implemented method comprising:
receiving video data representing a video that captures movements of a subject in a plurality of subjects;
identifying a first set of frames from the video data;
determining a rotated set of frames by rotating the first set of frames;
processing the first set of frames using a first trained model configured to identify a likelihood of the subject exhibiting a predetermined behavioral action;
based on the processing of the first set of frames by the first trained model, determining a first probability of the subject exhibiting the predetermined behavioral action in a first frame of the first set of frames, the first frame corresponding to a time duration of the video data;
processing the rotated set of frames using the first trained model;
determining a reflected set of frames by reflecting the first set of frames;
processing the reflected set of frames using the first trained model;
identifying the first label using the first probability, the second probability, and the third probability;
based on the processing of the rotated set of frames by the first trained model, determining a second probability of the subject exhibiting the predetermined behavioral action in a second frame of the rotated set of frames, the second frame corresponding to the time duration of the first frame;
based on the processing of the reflected set of frames by the first trained model, determining a third probability of the subject exhibiting the predetermined behavioral action a third frame of the reflected set of frames, the third frame corresponding to the first frame; and
using the first probability, the second probability, and the third probability, identifying a first label for the first frame, the first label indicating that the subject exhibits the predetermined behavioral action.

2. The computer-implemented method of claim 1, further comprising:
processing the first set of frames using a second trained model configured to identify a likelihood of the subject exhibiting the predetermined behavioral action;
based on the processing of the first set of frames by the second trained model, determining a third probability of the subject exhibiting the predetermined behavioral action in the first frame;
processing the rotated set of frames using the second trained model;
based on the processing of the rotated set of frames by the second trained model, determining a fourth probability of the subject exhibiting the predetermined behavioral action in the second frame; and
identifying the first label using the first probability, the second probability, the third probability and the fourth probability.

3. The computer-implemented method of claim 1, wherein the predetermined behavioral action comprises a grooming behavior, wherein the grooming behavior comprises at least one of paw licking, unilateral face wash, bilateral face wash, and flank licking.

4. The computer-implemented method of claim 1, wherein the first set of frames represent a portion of the video data during a time period, and the first frame is a last temporal frame of the time period.

5. The computer-implemented method of claim 1, further comprising:
identifying a second set of frames from the video data;
determining a second rotated set of frames by rotating the second set of frames;
processing the second set of frames using the first trained model;
based on the processing of the second set of frames by the first trained model, determining a third probability of the subject exhibiting the predetermined behavioral action in a third frame of the second set of frames;
processing the second rotated set of frames using the first trained model;

based on the processing of the second rotated set of frames by the first trained model, determining a fourth probability of the subject exhibiting the predetermined behavioral action in a fourth frame of the rotated set of frames, the fourth frame corresponding to the third frame; and using the third probability and the fourth probability, identifying a second label for the fourth frame, the first label indicating that the subject exhibits the predetermined behavioral action.

6. The computer-implemented method of claim 5, further comprising:

using at least the first label and the second label, generating an ethogram representing the predetermined behavioral action of the subject during a time period.

7. The computer-implemented method of claim 1, further comprising prior to receiving the video data:

receiving training data including a first plurality of video frames and a second plurality of video frames, each of the first plurality of video frames associated with a positive label indicating that the subject is exhibiting the predetermined behavioral action and each of the second plurality of video frames associated with a negative label indicating that the subject is exhibiting a behavioral action that is not the predetermined behavior action; and processing the training data using a first set of model parameters and first classifier model data to determine the first trained model.

8. The computer-implemented method of claim 7, wherein the first plurality of video frames and the second plurality of video frames represent movements of the plurality of subjects, wherein the subject in the plurality of subjects comprises one or more pre-identified physical characteristic(s).

9. The computer-implemented method of claim 8, wherein the pre-identified physical characteristic is one or more of a body shape, a body size, a coat color, a gender, an age, or a phenotype of a disease or disorder.

10. The computer-implemented method of claim 9, wherein the disease or disorder is a heritable disease, an injury, or a contagious disease.

11. The computer-implemented method of claim 7, wherein the first plurality of video frames and the second plurality of video frames represent movements of the plurality of subjects that are mice, wherein a mouse in the plurality of subjects that are mice comprises a coat color, a gender, a body shape and a size.

12. A computer-implemented method comprising:

receiving video data representing a video that captures movements of a subject in a plurality of subjects;

identifying a first set of frames from the video data;

processing the first set of frames using a first trained model configured to identify a likelihood of the subject exhibiting a predetermined behavioral action;

determining a reflected set of frames by reflecting the first set of frames;

processing the reflected set of frames using the first trained model;

based on the processing of the first set of frames by the first trained model, determining a first probability of the subject exhibiting the predetermined behavioral action in a first frame of the first set of frames;

processing the first set of frames using a second trained model configured to identify a likelihood of the subject exhibiting the predetermined behavioral action;

based on the processing of the first set of frames by the second trained model, determining a second probability of the subject exhibiting the predetermined behavioral action in the first frame;

based on the processing of the reflected set of frames by the first trained model, determining a third probability of the subject exhibiting the predetermined behavioral action in a second frame of the reflected set of frames, the second frame corresponding to the first frame;

processing the reflected set of frames using the second trained model;

based on the processing of the reflected set of frames by the second trained model, determining a fourth probability of the subject exhibiting the predetermined behavioral action in the second frame; and using the first probability, the second probability, the third probability, and the fourth probability, identifying a first label for the first frame, the first label indicating that the subject exhibits the predetermined behavioral action.

13. The computer-implemented method of claim 12, further comprising:

determining a rotated set of frames by rotating the first set of frames;

processing the rotated set of frames using the first trained model;

based on the processing of the rotated set of frames by the first trained model, determining a third probability of the subject exhibiting the predetermined behavioral action in a second frame of the rotated set of frames, the second frame corresponding to the first frame;

processing the rotated set of frames using the second trained model;

based on the processing of the rotated set of frames by the second trained model, determining a fourth probability of the subject exhibiting the predetermined behavioral action in the second frame; and identifying the first label using the first probability, the second probability, the third probability and the fourth probability.

14. The computer-implemented method of claim 12, wherein the first trained model and the second trained model are neural network models, the first trained model is initialized using a first set of parameters, and the second trained model is initialized using a second set of parameters different than the first set of parameters.

15. The computer-implemented method of claim 12, further comprising:

processing the first set of frames using a third trained model configured to identify a likelihood of the subject exhibiting a predetermined behavioral action;

based on the processing of the first set of frames by the third trained model, determining a third probability of the subject exhibiting the predetermined behavioral action in the first frame;

processing the first set of frames using a fourth trained model configured to identify a likelihood of the subject exhibiting the predetermined behavioral action;

based on the processing of the first set of frames by the fourth trained model, determining a fourth probability of the subject exhibiting the predetermined behavioral action in the first frame; and identifying the first label using the first probability, the second probability, the third probability, and the fourth probability.

16. The computer-implemented method of claim 12, further comprising:

identifying a second set of frames from the video data;

processing the second set of frames using the first trained model;

based on the processing of the second set of frames by the first trained model, determining a third probability of the subject exhibiting the predetermined behavioral action in a third frame of the second set of frames;

processing the second set of frames using the second trained model;

based on the processing of the second set of frames by the second trained model, determining a fourth probability of the subject exhibiting the predetermined behavioral action in the third frame; and using the third probability and the fourth probability, identifying a second label for the third frame, the second label indicating that the subject exhibits the predetermined behavioral action.

17. The computer-implemented method of claim 16, further comprising:

using at least the first label and the second label, generating an ethogram representing the predetermined behavioral action of the subject during a time period.

18. The computer-implemented method of claim 12, further comprising prior to receiving the video data:

receiving training data including a first plurality of video frames and a second plurality of video frames, each of the first plurality of video frames associated with a positive label indicating that the subject is exhibiting the predetermined behavioral action, and each of the second plurality of video frames associated with a negative label indicating that the subject is exhibiting a behavioral action that is not the predetermined behavioral action;

processing the training data using a first set of model parameters and first classifier model data to determine the first trained model; and processing the training data using a second set of model parameters and second classifier model data to determine the second trained model.

* * * * *